United States Patent
Xu et al.

(10) Patent No.: US 8,575,097 B2
(45) Date of Patent: Nov. 5, 2013

(54) EXENDIN VARIANT AND CONJUGATE THEREOF

(75) Inventors: Michael M. Xu, Jiangsu (CN); Yongxiang Wang, Shanghai (CN); Yinghui Zhang, Jiangsu (CN); Xiaosu Luo, Jiangsu (CN); Nian Gong, Shanghai (CN); Lijie Zhang, Jiangsu (CN); Xiangjun Zhou, Jiangsu (CN)

(73) Assignee: Pegbio Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 13/265,809

(22) PCT Filed: Apr. 23, 2010

(86) PCT No.: PCT/CN2010/072094
§ 371 (c)(1),
(2), (4) Date: Oct. 21, 2011

(87) PCT Pub. No.: WO2010/121559
PCT Pub. Date: Oct. 28, 2010

(65) Prior Publication Data
US 2012/0196795 A1   Aug. 2, 2012

(30) Foreign Application Priority Data

Apr. 23, 2009  (CN) .......................... 2009 1 0135363

(51) Int. Cl.
*A61K 38/00* (2006.01)
*A61P 3/04* (2006.01)
*A61P 3/10* (2006.01)

(52) U.S. Cl.
USPC ............... 514/7.2; 514/4.8; 514/4.9; 514/6.8; 514/6.9; 514/7.3

(58) Field of Classification Search
None
See application file for complete search history.

(56) References Cited

U.S. PATENT DOCUMENTS

| | | |
|---|---|---|
| 477,967 A | 6/1892 | Stevenson |
| 478,017 A | 6/1892 | Oliver |
| 478,425 A | 7/1892 | Harris |
| 5,424,286 A | 6/1995 | Eng |
| 5,932,462 A | 8/1999 | Harris et al. |
| 6,455,639 B1 | 9/2002 | Yasukohchi et al. |
| 6,566,506 B2 | 5/2003 | Greenwald et al. |
| 6,858,576 B1 | 2/2005 | Young et al. |
| 6,864,350 B2 | 3/2005 | Harris |
| 6,872,700 B1 | 3/2005 | Young et al. |
| 6,902,744 B1 | 6/2005 | Kolterman et al. |
| 6,956,026 B2 | 10/2005 | Beeley et al. |
| 7,297,761 B2 | 11/2007 | Beeley et al. |

FOREIGN PATENT DOCUMENTS

| | | |
|---|---|---|
| AU | 775063 B2 | 11/2000 |
| CN | 1372570 | 10/2002 |
| CN | 101125207 | 2/2008 |
| EA | 009366 | 12/2007 |
| WO | WO0041546 A2 | 7/2000 |
| WO | WO0066629 | 11/2000 |
| WO | WO03040211 A2 | 5/2003 |
| WO | WO 2006/074600 | 7/2006 |
| WO | WO2006083301 A2 | 8/2006 |
| WO | WO 2007/019331 | 2/2007 |
| WO | 2008/058461 | 5/2008 |
| WO | WO 2008/058461 | 5/2008 |
| WO | WO 2008/076933 | 6/2008 |
| WO | WO 2009/153960 | 12/2009 |
| WO | WO 2011/052523 | 5/2011 |

OTHER PUBLICATIONS

Pascal Bailon, et al. PEG-Modified Biopharmaceuticals. Pharmaceuticals, Quality Horizons. Expert Opin. Drug Deliv. (2009) 6(1):1-16.
M.D. Turton, et al. "A Role for Glucagon-like Peptide-1 in the Central Regulation of Feeding", Letters to Nature vol. 379. Endocrine unit, Department of Medicine, Hammersmith Hospital, London. Jan. 4, 1996.
Reza Halse, et al. "Control of Glycogen Synthesis by Glucose, Glycogen, and Insulin in Cultured Human Muscle Cells". Original Articles. Diabetes, vol. 50, Apr. 2001.
Henryk Zulewski, et al. "Multipotential Nestin-Positive Stem Cells Isolated from Adult Pancreatic Islets Differentiate Ex Vivo into Pancreatic Endocrine, Exocrine, and Hepatic Phenotypes". Diabetes, vol. 50, pp. 525-529, Mar. 2001.
Mette Zander, et al. "Effect of 6-week course of glucagon-like peptide 1 on glycaemic control, insulin sensitivity, and β-cell function in type 2 diabetes: a parallel-group study". The Lancet, vol. 359, Mar. 2002.
John B. Buse, et al. "Effects of Exenatide (Exendin-4) on Glycemic Control Over 30 Weeks in Sulfonylurea-Treated Patients with Type 2 Diabetes". Diabetes Care, vol. 27 No. 11, Nov. 2004, pp. 2628-2635.
M.A. Nauck, et al. "Effects of Subcutaneous Glucagon-like Peptide 1 (GLP-! [7-36 amide]) in Patients with NIDDM". Diabetologia (1996) 39: pp. 1546-1553.
Jean-Pierre Raufman, et al. Exendin-3, a Novel Peptide from *Helderma horridum* Venom, Interacts with Vasoactive Intestinal Peptide Receptors and a Newly Described Receptor on Dispersed Acini from Guinea Pig Pancreas. The Journal of Biological Chemistry, vol. 266, No. 5, Feb. 15, 1991, pp. 2897-2902.

(Continued)

*Primary Examiner* — Gyan Chandra
(74) *Attorney, Agent, or Firm* — Workman Nydegger

(57) ABSTRACT

The invention provides a novel Exendin variant and the Exendin variant conjugate conjugating polymer thereon, the pharmaceutical composition comprising them and use of them for treating diseases such as reducing blood glucose, treating diabetes, especially Type II diabetes. The invention also provides the use of Exendin conjugate for lowering body weight.

15 Claims, 23 Drawing Sheets

(56) References Cited

OTHER PUBLICATIONS

Andreas Brandt, et al. GLP-1-induced Alterations in the Glucose-stimulated Insulin Secretory Dose-response Curve. Am J Physiol Endocrinol Metab 281:E242-E247, 2001. Downloaded from ajpendo.physiology.org on Nov. 7, 2011.

Rafael R. Schick, et al. Glucagon-like peptide 1-(7-36) amide acts at lateral and medial hypothalamic sites to suppress feeding in rats. Am J Physiol Regul Integr Comp Physiol 284:R1427-R1435, Nov. 7, 2002. Downloaded from ajpendo.physiology.org on Nov. 7, 2011.

Lotte Bjerre Knudsen. Glucagon-like Peptide-1: The Basis of a New Class of Treatment for Type 2 Diabetes. J. Med. Chem. 2004, 47, 4128-4134. Received Dec. 24, 2003.

Q. Wang, P.L. Brubaker. Glucagon-like peptide-1 treatment delays the onset of diabetes in 8 week-old db/db mice. Diabetologia (Apr. 2002) 45:1263-1273.

Maire E. Doyle and Josephine M. Egan. Glucagon-like Peptide-1. The Endocrine Society. Downloaded from rphr.endojournals.org by on Nov. 7, 2011.

Brian C. Cunningham, James A. Wells. High-Resolution Epitope Mapping of hGH-Receptor Interactions by Alanine-Scanning Multagenesis. *Science*, New Series, vol. 244, No. 4908 (Jun. 2, 1989), pp. 1081-1085.

Abraham M. de Vos, et al. Human Growth Hormone and Extracellular Domain of its Receptor: Crystal Structure of the Complex. *Science*, New Series, vol. 255, Issue 5042 (Jan. 17, 1992), 306-312.

John Eng, et al. Isolation and Characterization of Exendin-4, an Exendin-3 Analogue, from *Heloderma suspectum* Venom. The Journal of Biological Chemistry, vol. 267, No. 11, Apr. 15, 1992, pp. 7402-7405.

Philip J Larsen. Mechanisms behind GLP-1 induced weight loss. *The British Journal of Disease & Vascular Disease* Aug. 2008 (Suppl 2): S34-S41. Downloaded from dvd.sagepub.com at Shanghai Jiao Tong Univ on Nov. 7, 2011.

W. Creutzfeldt and R. Ebert. New developments in the Incretin Concept. Diabetologia (1985) 28: 565-573.

Susan Bonner-Weir & Gordon C Weir. New Sources of pancreatic β-cells. Nature Biotechnology, vol. 23, No. 7. Jul. 2005, pp. 857-861.

T. Vilsbøll, et al. No reactive hypoglycaemia in Type 2 diabetic patients after subcutaneous administration of GLP-1 and intravenous glucose. *Diabetic Medicine*, 18, 144-149 (2001), Accepted Oct. 18, 2000.

Mark A. Myers, et al. Pancreatic Islet Cell Cytoplasmic Antibody in Diabetes Is Represented by Antibodies to Islet Cell Antigen 512 and Glutamic Acid Decarboxylase. Diabetes, vol. 44, Nov. 1995, 1290-1295.

Cecil Tourrel, et al. Persistent Improvement of Type 2 Diabetes in the Goto-Kakizaki rat Model by Expansion of the β-cell Mass During the Prediabetic Period with Glucagon-Like Peptide-1 or Exendin-4. Diabetes, vol. 51, May 2002, pp. 1443-1452.

John Eng, et al. Puriciation and Structure of Exendin-3, a New Pancreatic Secretagogue Isolated from *Helderma horridum* Venom. The Journal of Biological Chemistry, vol. 265, No. 33, Nov. 25, 1990, pp. 20259-20262.

Maureen I. Harris, et al. Racial and Ethnic Differences in Glycemic Control of Adults With Type 2 Diabetes. *Diabetes Care*, vol. 22, No. 3, Mar. 1999, pp. 403-408.

Pascal Bailon, et al. Rational Design of a Potent, Long-Lasting Forn of Interferon: A 40 kDa Branched Polythylene Glycol-Conjugated Interferon α-2a for the Treatment of Hepatitis C. *Bioconjugate Chem.* 2001, vol. 12, No. 2, 195-202.

Frank Kolligs, et al. Reduction of the Incretin Effect in Rats by the Glucagon-Like Peptide 1 Receptor Antagonist Exendin (9-39) Amide. Diabetes, vol. 44, Jan. 1995.

Sharon Bowne, et al. Relationship Between Molecular Mass and Duration of Activity of Polythylene Glycol Conjugated Granulocyte Colony-stimulating Factor Mutein. Experimental Hematology vol. 27, pp. 425-432 (1999) Accepted Sep. 1998.

Diva D. De León, et al. Role of Endogenous Glucagon-Like Peptide-1 in Inslet Regeneration After Partial Pancreatectomy. Diabetes, vol. 52, Feb. 2003.

Shalin A. Modi, et al. Sustained Release Drug Delivery System: A Review. International Journal of Pharma. Research & Development. vol. 2, Issue 12, Feb. 2011, pp. 147-160.

Orville G. Kolterman, et al. Synthetic Exendin-4 (Exenatide) Significantly Reduces Postprandial and Fasting Plasma Glucose in Subjects with Type 2 Diabetes. The Journal of Clinical Endorcrine Society 88(7)pp. 3082-3089, Jul. 2003.

Francesco M. Veronese "Peptide and protein PEGylation: a review of problems and solutions" Department of Pharmaceutical Sciences, CNR, Center for Chemical Investigation of Drugs, University of Padova, Via F. Marzolo 5, 35131 Padova, Italy Received Mar. 8, 2000; accepted May 30, 2000. 13 pages.

Enzymatic activity and thermal stability of PEG-a-chymotrypsin conjugates Jose' A. Rodriguez-Martinez, Izarys Rivera-Rivera, Ricardo J. Sola, Kai Griebenow, Feb. 6, 2009 / Published online: Feb. 18, 2009, Springer Science+Business Media B.V. 2009, 5 pages.

"Use of Exenatide in Patients With Type 2 Diabetes" Robert Hood, MD; Virginia Valentine, CNS, BC-ADM, CDE; Susanna Mac, MD, PhD; and William H Polonsky, PhD, CDE, Diabetes Spectrum vol. 19, No. 3, 2006, 6 pages.

Russian Office Action issued in Russian application No. 2011147083, dated Feb. 4, 2013.

European Search Report for European Patent Application No. EP 10 76 6649 dated Oct. 26, 2012.

Russian Office Action for Russian Application No. 2011147083/10(070585) dated Oct. 18, 2012.

EXENDIN VARIANT AND CONJUGATE THEREOF

CROSS-REFERENCE TO RELATED APPLICATIONS

This Patent Application is a U.S. National Stage of International Application No. PCT/CN2010/072094, filed on Apr. 23, 2010, which claims priority to Chinese Application No. 200910135363.5, filed on Apr. 23, 2009, the disclosures of which are incorporated herein by reference in their entireties.

FIELD OF INVENTION

The present invention relates to novel Exendin variants, the conjugates thereof with polymers, and pharmaceutical composition containing them, as well as to the use of the Exendin variants, the conjugates, and the pharmaceutical compositions in reducing blood glucose, especially in treating diabetes (in particular Type II diabetes). The present invention also relates to the use of Exendin conjugates in reducing body weight.

BACKGROUND OF THE INVENTION

With social development, prolongation of life expectation and change of lifestyle, diabetes mellitus has been one of the leading healthcare problems around the world. Both in developed countries and developing countries, morbidity of diabetes mellitus is rapidly growing. In 2007, there are around 246 million diabetes patients in the world, and one diabetes patient dies every 10 seconds around the world. It is estimated that the population of diabetes patients in the world will reach 333 million till 2025. China has been a severe region for diabetes. In China, the population of diabetes patients is currently 40 million, which is the second largest number in the world (the first is India), with the morbidity of around 5%. Diabetes mellitus comprises two types: one is insulin-dependent diabetes mellitus (Type 1 diabetes) and the other is non-insulin-dependent diabetes mellitus (Type 2 diabetes). Among them, Type 2 diabetes contributes to more than 90% of diabetes. Type 2 diabetes is characterized by uncontrolled insulin secretion or function as well as dysfunction of β-cell, resulting in disorder of lipid, carbohydrate and protein metabolism. It may lead to chronic hyperglycemia and eventually induce complications occur in microvasculature, macrovasculature and various organs. At present, there are two classes of medication for controlling diabetes mellitus: 1) insulin-secretion promoters, such as sulfonylureas, meglitinides, and dipeptidyl peptidase inhibitors, GLP-1 analogs; and 2) non-insulin-secretion promoters, such as insulin, α-glucosidase inhibitors, biguanides, thiazolidinediones, and insulin analogs. Currently, most anti-diabetic medications commonly used in clinic is less efficient for Type 2 diabetes. They fail to stop progressive damage of pancreas β-cell, to reduce blood level of HbA1c, and to prevent complications of diabetes, such as heart disease and kidney failure. In addition, they have, to some extent, toxic side effects. Accordingly, there is a need to study new medication for treatment of Type 2 diabetes.

In 1985, an intestinal hormone, Glucagon-like peptide-1 (GLP-1), was discovered. GLP-1 is expressed by proglucagons gene after eating, and mainly secreted by L-cells in intestinal mucosa. GLP-1 stimulates pancreas islet β-cell to secret insulin (J Med Chem, 47, 4128-4134, 2004), and play an important role in stabilizing blood glucose level. Administering GLP-1 may control blood glucose at normal level in Type 2 diabetes patients (Diabetes Care, 15, 270-276, 1992; Lancet, 359, 824-830, 2002; Endoer. Rev, 16, 390-410, 1996; Diabetologia, 28, 565-573, 1985). GLP-1 has functions as follows: glucose-dependent action on pancreas islet β-cell so as to promote the transcription of insulin gene, and increase biosynthesis and secretion of insulin; stimulating the proliferation and differentiation of β-cell and inhibiting apoptosis of β-cell so as to increase the amount of pancreas islet β-cells; inhibiting secretion of glucagons; increasing sensitivity of insulin receptors in peripheral cells; decreasing HbA1c level; suppressing appetite and eating; delaying gastric emptying (Diabetic Med, 18, 144-149, 2001; Diabetes, 51, 1443-1452, 2002; Diabetologia, 45, 1263-1273, 2002; Diabetes, 50, 525-529, 2001; Diabetes, 50, 725, 2001; Diabetes, 52, 365-371, 2003; Recent Prog. Hormne Res. 56, 377-399, 2001; Disbetologia, 39, 1546-1553, 1996; Am. J. Physicl Endocrinol. Metab, 281, E242-247, 2001; U.S. Pat. Nos. 4,779,67, 4,780, 17, 4,784,25; Diabetes Care, 22, 403-408, 1999; J. Clin. Endocrinology and Metabolism, 88, 3082-3089, 2003; Diabetes, 44, 1295, 1995). However, GLP-1 is easily degraded by dipeptidyl peptidase (DPP IV) in the body, and has a half life of less than 2 minutes, and thus GLP-1 cannot be used as an effective anti-diabetic drug.

Exendin-4 is a polypeptide which is found in the saliva of the Gila monster, a poisonous lizard that lives in Arizona and New Mexico of the United States (J. Biol. Chem., 265, 20259-20262, 1990; J. Biol. Chem., 267, 7402-7405, 1992). Exendin-4 is highly homologous with GLP-1 (7-36) (53%). It is reported that Exendin-4 may bind to GLP-1 receptor and exhibits pharmacological agonistic effect similar to that of GLP-1, for example, increasing the synthesis of insulin, promoting insulin secretion in a glucose-dependent manner; stimulating proliferation and regeneration of β-cells and inhibiting apoptosis of β-cells so as to increase the amount of β-cells; inhibiting the secretion of glucagons; inhibiting generation of glycogen without inducing severe hypoglycemia; inhibiting gastrointestinal motility and secretion after eating; decreasing appetite and decreasing food uptake; protecting nerve cells (Nat. Biotech, 23, 857-861, 2005; J. Biol. Chem., 266, 2897-2902, 1991; J. Biol. Chem., 266, 21432-21437, 1992; Diabetes, 44, 16-19, 1995; Nature, 379, 69-72, 1996). The effect of Exendin-4 to promote the secretion of insulin and to inhibit the secretion of glucagon after eating is dependent on blood glucose, which is advantageous compared with currently used sulfonylureas, and in particular, Exendin-4 is less susceptible to induce hypoglycemia, and it greatly decreases the frequency of blood glucose monitoring and also lowers the body weight. A b.i.d. formulation of Exendin-4 (Exenatide, marketed as Byetta), co-developed by Amylin and Eli Lilly, is approved for market in U.S. and Europe (U.S. Pat. Nos. 5,424,286, 6,858,576, 6,872,700, 6,902,744, 6,956, 026, 7,297,761). As such, this type of medication has been widely used in the treatment of diabetes and obesity around the world.

Pharmaceutical polypeptides requires multiple injections daily, since these pharmaceuticals have short half life in the body and poor physical and chemical stability, and they are susceptible to the degradation by various proteases. Exenatide is used b.i.d as an s.c. injection, which brings to patients a heavy burden in body, psychology and economy, and thus compliance of patients is limited. Accordingly, current studies of anti-diabetic drugs focus on structurally modifying Exendin-4 and developing new dosage form, in order to prolong plasma half life of Exendin-4 and increase systemic drug exposure.

Polymer modification technique is a potent modification technique which was developed since 1970s, in which PEGylation is a typical technique. This technique is to chemically conjugate PEG to a pharmaceutical protein, in order to modify the surface of the protein. Upon PEG modification, molecular weight of proteins is increased and clearance rate in kidney is decreased. In addition, a conjugated PEG chain results in steric hindrance on the modified protein molecule, leading to reduction of protein hydrolysis by proteases in blood. Thus, it efficiently prolongs the residence of proteins in circulation, and leads to prolongation of plasma half life and systemic drug exposure, resulting in improved efficacy.

At present, PEGylation has progressed into its second generation, site specific PEGylation. Site specific PEGylation can be used to specifically modify certain amino acids in proteins, and thereby prevent random modification. As such, the structure of active center in proteins is less influenced and certain antigenic sites are selectively intervened, resulting in reducing disadvantages such as reduced biological activity and increased heterogeneity due to non-site-specific PEGylation.

Scientists have carried out some studies on polymer modification of Exendin-4. Young and Prickett (CN1372570A) proved that Exendin-4 is mainly metabolized by renal clearance. Thus they modified Exendin-4 using PEG with a molecular weight ranging from 500 to 20,000 Dalton (Da). Wenchao Bao, Hongjing Xu, Gang Yu, Yajun Zuo (CN101125207A) performed amino modification in Exendin-4 using PEG with a molecular weight ranging from 20 kDa to 50 kDa.

However, there are disadvantages in existing Exendin-4 or variants thereof and various modified forms, including high administration frequency, which brings to patients heavy physical, psychological and economical burden. Thus compliance of patients is limited, and these drugs cannot be widely used. Accordingly, there still need new Exendin-4 variants and the variants modified by polymer.

SUMMARY OF THE INVENTION

In an aspect, the present invention provides an Exendin variant having the activity of GLP-1 receptor agonist, in which one or more amino acid residues are substituted by cysteine compared with wild-type Exendin sequence. Optionally, one or more amino acids are further deleted, added and/or substituted in the Exendin variant, in which amino acids to be incorporated by addition or substitution may be natural or non-natural amino acids or amino acid analogs.

In an embodiment, the Exendin variant has an amino acid sequence in which one or more amino acid residues are substituted by cysteine and optionally other amino acid, compared with wild-type Exendin-4 Sequence
His-Gly-Glu-Gly-Thr-Phe-Thr-Ser-Asp-Leu-Ser-Lys-Gln-Met-Glu-Glu -Glu-Ala-Val-Arg-Leu-Phe-Ile-Glu-Trp-Leu-Lys-Asn-Gly-Gly-Pro-Ser-Ser -Gly-Ala-Pro-Pro-Pro-Ser (SEQ ID NO: 1), or Exendin-3 Sequence
His-Ser-Asp-Gly-Thr-Phe-Thr-Ser-Asp-Leu-Ser-Lys-Gln-Met-Glu-Glu -Glu-Ala-Val-Arg-Leu-Phe-Ile-Glu-Trp-Leu-Lys-Asn-Gly-Gly-Pro-Ser-Ser -Gly-Ala-Pro-Pro-Pro-Ser (SEQ ID NO: 2), or their similar sequence. The amino acid substitutions are each independently located at N-terminal, C-terminal and/or within internal portion of the wild-type amino acid sequence.

In a preferred embodiment, the Exendin variant has a cysteine substitution at least at C-terminal of the variant. Further preferably, the Exendin variant has a cysteine substitution at the last amino acid of C-terminal. Furthermore, the Exendin variant preferably has a cysteine substitution at least at one or more positions selected from the group consisting of the positions corresponding to Arg at position 20, Trp at position 25, Ala at position 35 and Ser at position 39 of Exendin-4 or Exendin-3.

In a further aspect, the present invention provides an Exendin variant conjugate, in which one or more natural or synthetic polymer moieties (preferably physiologically acceptable polymer, such as polyalkylene glycol, more particularly PEG) is conjugated to the Exendin variant. In an embodiment that multiple polymer moieties are comprised in the conjugate, each of the polymer moieties may be same or not. Preferably, the polymer moiety is conjugated to the Exendin variant through one or more cysteine. In an embodiment, the polymer moiety is conjugated to the Exendin variant through thioether bond.

It is known by the skilled person that, in a biomolecule conjugated with a polymer moiety, the conjugated biomolecule has biological activity which is reduced exponentially, as molecular weight of the conjugating moiety increases (for example starting from 4 kDa) (Bailon et al. Rational design of potent, long-lasting form of interferon: A 40 kDa branched polyethylene glycol-conjugated interferon α-2a for the treatment of hepatitis C. Bioconjugate Chem, 2001, 12:195-202; Bowen et al. Relationship between molecular weight and duration of activity of polyethylene glycol conjugated granulocyte colony-stimulating factor mutein. Experimental Hematology, 1999, 27:425-32; Bailon et al. PEG-modified biopharmaceuticals. Expert Opin Deliv., 2009, 6:1-16). It is also known by the skilled person that the biological half-life and/or plasma half-life as well as systematic drug explosure of the conjugate molecule prolong or increase gradually, as molecular weight of the conjugating moiety increases.

However, the inventors surprisingly found that, compared with unconjugated Exendin variant, the Exendin variant conjugate molecule of the present invention still retains most of GLP-1 receptor agonist activity, even though molecular weight of the polymer moiety increases up to 30 kDa. Even if molecular weight of the PEG moiety increases up to 40 kDa or more, the Exendin variant conjugate of the present invention still retains substantively activity of GLP-1 receptor agonist. In particular, when molecular weight of the polymer moiety increases from 5 kDa to 27 kDa, the GLP-1 receptor agonist activity of the Exendin variant conjugate is substantively the same, compared with unconjugated Exendin variant.

Thus, in a preferred embodiment, the present invention provides an Exendin variant conjugate with a prolonged biological half-life and/or plasma half-life and the substantial activity of GLP-1 receptor agonist.

In an embodiment, the polymer is polyalkylene glycol, and includes for example polyethylene glycol, polypropylene glycol inter cilia. The one or more polymer moieties may have any appropriate molecular weight, for example 2 kDa to 50 kDa, preferably 5 kDa to 30 kDa, more preferably 20 kDa to 30 kDa, such as 21 kDa, 22 kDa, 23 kDa, 24 kDa, 25 kDa, 26 kDa, 27 kDa, 28 kDa, 29 kDa, and 30 kDa as well as any value between the above molecular weights.

Optionally, the Exendin variant conjugate may also be conjugated with one or more of the above polymers which are identical or not, at one or more other amino acid residues. The one or more other amino acid residues may be each independently located at N-terminal, C-terminal and/or within internal portion of the Exendin variant.

In the present invention, the polymer for conjugation may be in any appropriate configuration, including for example single-arm, double-arm, multi-arm and/or branched, in which each of the arms or branches may be the same or not.

The present invention further provides a method for preparing the Exendin variant conjugate as above, comprising contacting the Exendin variant with the polymer, preferably the polymer is attached with a reactive group or activated when contacting, so as to conjugate the activated polymer to one or more cysteine residues of the Exendin variant. In an embodiment, cysteines in the Exendin variant is specifically modified by PEG with different length of polymer chain and polymer structure, through selecting specific activating group and appropriate pH. In a particular embodiment, the specific activating group is maleimide.

The present invention further provides a pharmaceutical composition, comprising the Exendin variant and/or the Exendin variant conjugate of the present invention, as well as optionally a pharmaceutically acceptable carrier.

The present invention further provides a method for treating diseases, comprising administrating an therapeutically effective amount of the Exendin variant and/or the Exendin variant conjugate and/or the pharmaceutical composition of the present invention to a subject in need thereof. Similarly, the present invention also provides use of the Exendin variant and/or the Exendin variant conjugate and/or the pharmaceutical composition of the present invention in manufacturing a medicament for treatment of diseases. The diseases may be selected from the group consisting of: postprandial dumping syndrome, postprandial hyperglycemia, glucose intolerance, disorders or diseases which can be relieved by inhibiting glucagon secretion, by regulating triglycerides level, and/or by reducing food intake, obesity, eating disorders, insulin resistance syndrome, diabetes, hyperglycemia, and hypoglycemia. Preferably, the disease is diabetes. More preferably, the disease is Type 1 diabetes or Type 2 diabetes, in particular Type 2 diabetes.

It is well known that Exendin reduces body weight of obesity patients and induce nausea and vomiting, in which the mechanism of action is associated with inhibition of feeding center and vomit activating center in center nervous system (Larsen. Mechanisms behind GLP-1 induced weight loss. Br J Diabetes Vasc Dis 2008; 8: S34-S41; Schick et al. Glucagon like peptide 1 (7-36)-amide acts at lateral and medial hypothalamic sites to suppress feeding in rats. Am J Physiol Regul Integr Comp Physiol 2003; 284:R1427-35). The conjugate of Exendin or variant thereof cannot pass across blood-brain barrier due to increased molecular weight, and thus reduce vomiting induced by Exendin. Accordingly, before the initiation of the present invention, the inventors have ever expected the conjugate of Exendin or variant thereof would also have reduced effects in reducing food intake and body weight mediated by central nervous system. However, the inventors unexpectedly found that the conjugate of Exendin or variant thereof significantly enhanced effects in reducing body weight and food intake, although wild-type Exendin and unconjugated Exendin variant both reduce body weight and food intake.

Thus, in another aspect, the present invention provides a method of reducing body weight by administering a conjugate of Exendin or variant thereof and/or a pharmaceutical composition comprising the same. In addition, the present invention also provides uses of the conjugate of Exendin or variant thereof and/or the pharmaceutical composition comprising the same in manufacturing a medicament for reducing body weight. In an embodiment, the conjugate of Exendin or variant thereof is the conjugate of Exendin variant of the present invention as described above.

DESCRIPTION OF THE PREFERRED EMBODIMENTS

Definition

Figure 1:
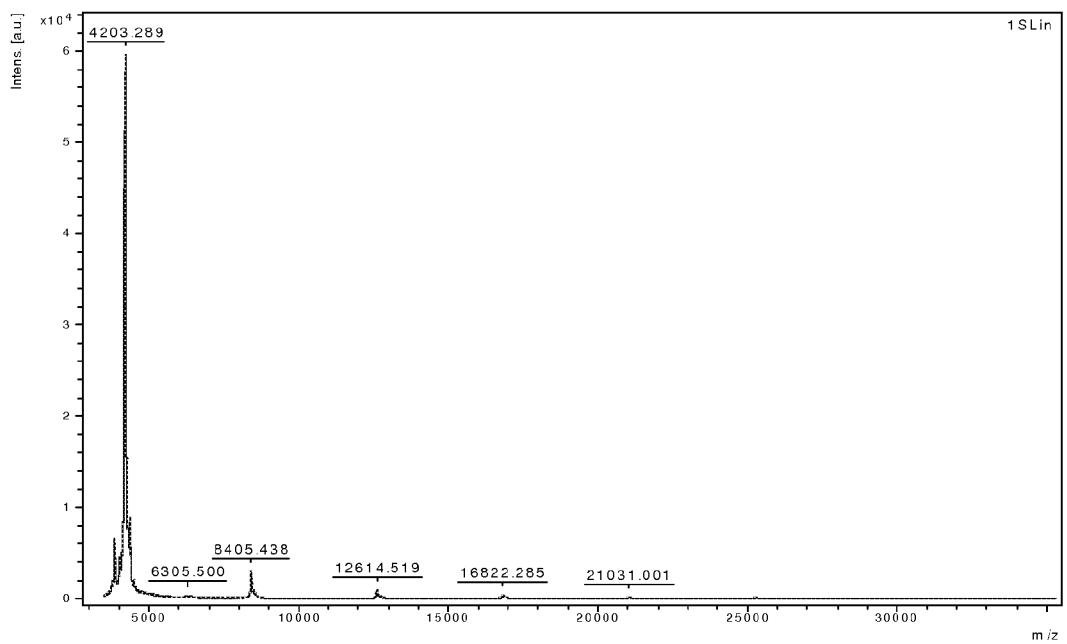
FIG. 1 shows mass spectrum of PB-105 obtained in Example 1.

As used herein, the term "amino acid" includes natural amino acid, non-natural amino acid, and amino acid analog, as well as all D- and L-stereoisomers thereof. Non-natural amino acid includes but not limited to azetidine carboxylic acid, 2-aminoadipic acid, 3-aminoadipic acid, β-alanine, alanine, 2-aminobutyric acid, 4-aminobutyric acid, 6-aminocaproic acid, 2-aminoheptanoic acid, 2-aminoisobutyric acid, 3-aminoisobutyric acid, 2-aminoheptanedioic acid, tert-butyl glycine, 2,4-aminoisobutyric acid, 2,2'-diamino-heptanedioic acid, 2,3-diaminopropionic acid, N-ethyl glycine, N-ethyl asparagine, homoproline, hydroxylysine, allo-hydroxy-lysine, 3-hydroxyproline, 4-hydroxyproline, isodemosine, allo-isoleucine, N-methyl alanine, N-methyl glycine, N-methyl isoleucine, N-methyl-amyl glycine, N-methyl valine, alanine naphthalene, norvaline, norleucine, ornithine, glycine amyl, 2-piperidine acid and thioproline. Amino acid analog includes natural amino acid and non-natural amino acid in which carboxy group at C-terminal, amino group at N-terminal or side-chain group is reversibly or irreversibly chemically blocked, or chemically modified to another functional group, such as methionine sulfoxide, methionine sulfone, S-(carboxymethyl)-cysteine, S-(carboxymethyl)-cysteine sulfoxide and S-(carboxymethyl)-cysteine sulfoxide.

As used herein, the term "polypeptide" or "protein" interchangeably means a string of at least two amino acid residues linked each other by covalent bond (such as peptide bond), which may be recombinate polypeptide, natural polypeptide or synthetic polypeptide.

As used herein, the term "cysteine substitution" means replacing one or more other amino acid residues in a natural polypeptide (such as Exendin-4) by cysteine residue by means of genetic engineering or artificially chemical synthesis.

As used herein, the term "polypeptide variant", "variant" or "analog" means a polypeptide in which the amino acid sequence is different due to one or more substitutions, deletions, insertions, fusions, truncations or any combination thereof. The polypeptide variant may be fully functional or lack one or more functional activity. The fully functional variant may contain change such as merely conserved change or at non-essential residue or in non-essential region. The functional variant may comprise substitution of similar amino acid, resulting in no change or insignificantly functional change. The important amino acid for functions may be identified by known methods in the art, such as site specific mutagenesis or glycine scanning mutagenesis (Cunningham, B. and Wells, J., Science, 244: 1081-1085, 1989). The key position for the activity of polypeptides may be determined, for example by structural analysis such as crystallization, NMR or photoaffinity labeling (Smith, L. et al., J. Mol. Biol., 224: 899-904, 1992; de Vos, A. et al., Science, 255: 306-312, 1992). The term "thiol variant" means polypeptide variants in which a thiol is present in the amino acid sequence by substitution, insertion, fusion or any combination thereof.

As used herein, the term "conjugate" means a product formed by covalent or non-covalent linkage of a polypeptide or a polypeptide variant and the modification group of the present invention. The modification group includes but not limits to the examples as above.

As used herein, the term "a modified polypeptide" or "a modified polypeptide variant" means a polypeptide or a polypeptide variant in which one or more amino acid is chemically modified, wherein the modification is covalent or non-covalent modification of various groups, including but not limit to phosphorylation, glycosylation, methylation, PEGylation, biotinylation, SUMOylation, acetylation, and the same.

As used herein, the term "alkyl" means substituted or non-substituted straight-chain or branched alkyl, such as C1-C30 alkyl, C1-C20 alkyl, C2-C15 alkyl or C3-C10 alkyl, in which optionally substituted by one or more substituent independently selected from the group consisting of such as halogen, amino, nitro group and the same.

As used herein, the term "cycloalkyl" means substituted or non-substituted C3-C8 cycloalkyl, in which optionally substituted by one or more substituent independently selected from the group consisting of such as C1-C10 alkyl, C2-C10 alkenyl, C2-C10 alkynyl, halogen, amino, and nitro group.

As used herein, the term "alkenyl" means substituted or non-substituted straight-chain or branched alkenyl having one or more carbon-carbon double bond, in which such as 2-20, 3-15, 4-10 carbon atoms may be present, and optionally substituted by one or more substituent independently selected from the group consisting of such as halogen, amino, and nitro group.

As used herein, the term "aryl" means C6-C10 aryl, optionally substituted by one or more substituent independently selected from the group consisting of such as C1-C10 alkyl, C2-C10 alkenyl, C2-C10 alkynyl, halogen, amino, and nitro group.

As used herein, the term "linker" means an organic group, which links PEG to the Exendin. In the present invention, the linker may be alkyl, ether, amide, ester, thiol and the like, and the linker may comprise for example up to 30 carbon atoms, for example 1-25, 2-20, 3-15 or 3-10 carbon atoms.

In general, as used herein, the term "polyethylene glycol" has the meaning which is usually understood by the skilled person, includes both polyethylene glycol per se and its derivatives with a terminal modification, unless otherwise specified.

In addition, for polymer such as polyethylene glycol, there are varieties of methods for determining the molecular weight. Average molecular weight (in particular number average molecular weight or weight average molecular weight) is generally used to represent the molecular weight of a polymer, since a polymer is formed by molecules with different degrees of polymerization in a range of distribution. Number average molecular weight and weight average molecular weight tend to be equal for polymers with a narrow range of distribution, although they may be different to a certain extent when the degree of polymerization in polymers largely differs. For polymers such as polyethylene glycol mentioned herein, the molecular weight may be either number average molecular weight or weight average molecular weight when mentioned.

Exendin Variants

In one aspect, the present invention relates to an Exendin variant with activity of GLP-1 receptor agonist, in which one or more (for example 1, 2, 3, 4, 5 or more) amino acid residues are substituted by cysteine compared with wild-type Exendin sequence. The cysteine substitution is each independently located at N-terminal, C-terminal and/or in the internal portion of the Exendin variant sequence. In some embodiments, the Exendin variant has cysteine substitution at least at 1, 2, 3, or 4 amino acid residues of C-terminal thereof. Preferably, the Exendin variant has a cysteine substitution at the last amino acid of C-terminal. In some other embodiments, preferably, the Exendin variant has a cysteine substitution at 1, 2, 3, 4, or more amino acid residues of C-terminal, N-terminal and/or in the internal portion of the Exendin variant.

The wild-type Exendin sequence or similar sequence described in the present invention may be any known sequence in the art, including various variants or analogs or agonist sequences thereof. With respect to the teachings of Exendin, please see for example Eng J. et al., J. Biol. Chem., 265: 20259-62, 1990; Eng J. et al., J. Biol. Chem., 267: 7402-05, 1992; WO00/66629 and WO00/41546, each of which is incorporated herein entirely by reference.

The Exendin variant may also optionally have one or more (such as 1, 2, 3, 4, 5, or more) further amino acid modifications, including for example amino acid substitution, deletion, insertion and/or addition. Similarly, the further amino acid modification may be independently located at N-terminal, C-terminal and/or within the internal portion of the Exendin sequence. The amino acid substituted, inserted and/or added may be any natural amino acid, non-natural amino acid or amino acid analog, or D- or L-stereoisomer. In some embodiments, the further amino acid modification is conserved amino acid substitution, for example substitution between Ala/Gly, Ser/Thr, Glu/Asp, Gln/Asn, Ala/Val/Ile/Leu, Arg/Lys, Phe/Tyr, etc. For conserved amino acid substitution, lots of teachings are present in the prior art, for example see WO/2006/083301, which is incorporated herein entirely by reference.

In the present invention, the wild-type Exendin may be Exendin-3 or Exendin-4. Thus, in some embodiments, the present invention relates to such Exendin variants, in which one or more (such as 1, 2, 3, 4, 5, or more) amino acid residues are substituted by cysteine, compared with His-Gly-Glu-Gly-Thr-Phe-Thr-Ser-Asp-Lu-Ser-Lys-Gln-Met-Glu-Glu -Glu-Ala-Val-Arg-Leu-Phe-Ile-Glu-Trp-Leu-Lys-Asn-Gly-Gly-Pro-Ser-Ser -Gly-Ala-Pro-Pro-Pro-Ser (SEQ ID NO: 1; Exendin-4) or His-Ser-Asp-Gly-Thr-Phe-Thr-Ser-Asp-Leu-Ser-Lys-Gln-Met-Glu-Glu -Glu-Ala-Val-Arg-Leu-Phe-Ile-Glu-Trp-Leu-Lys-Asn-Gly-Gly-Pro-Ser-Ser -Gly-Ala-Pro-Pro-Pro-Ser (SEQ ID NO: 2; Exendin-3) or similar sequence. Preferably, the Exendin variant has a cysteine substitution at least at one or more positions selected from the group consisting of the positions corresponding to Arg (arginine) at position 20, Trp (tryptophan) at position 25, Ala (alanine) at position 35 and Ser (serine) at position 39 of SEQ ID NO: 1 or SEQ ID NO: 2.

In a preferred embodiment, the Exendin variant has a amino acid sequence selected from the group consisting of:

```
                                          (SEQ ID NO: 3)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Cys;
```

-continued (SEQ ID NO: 4)
His-Gly-Glu-Gly-Thr-Phe-Thr-Ser-Asp-Leu-Ser-Lys-

Gln-Met-Glu-Glu-Ala-Val-Arg-Leu-Phe-Ile-Glu-

Trp-Leu-Lys-Asn-Gly-Gly-Pro-Ser-Ser-Gly-Cys-Pro-

Pro-Pro-Ser;

(SEQ ID NO: 5)
His-Gly-Glu-Gly-Thr-Phe-Thr-Ser-Asp-Leu-Ser-Lys-

Gln-Met-Glu-Glu-Ala-Val-Arg-Leu-Phe-Ile-Glu-

Trp-Leu-Lys-Asn-Gly-Cys-Pro-Ser-Ser-Gly-Ala-Pro-

Pro-Pro-Ser;

(SEQ ID NO: 6)
His-Gly-Glu-Gly-Thr-Phe-Thr-Ser-Asp-Leu-Ser-Lys-

Gln-Met-Glu-Glu-Ala-Val-Arg-Leu-Phe-Ile-Glu-

Cys-Leu-Lys-Asn-Gly-Gly-Pro-Ser-Ser-Gly-Ala-Pro-

Pro-Pro-Ser;

(SEQ ID NO: 7)
His-Gly-Glu-Gly-Thr-Phe-Thr-Ser-Asp-Leu-Ser-Lys-

Gln-Met-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Cys-Tyr;
or (SEQ ID NO: 8)
His-dAla-Glu-Gly-Thr-Phe-Thr-Ser-Asp-Leu-Ser-Lys-

Gln-Met-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Cys.

As described above, the Exendin variant of the present invention may also optionally have one or more (such as 1, 2, 3, 4, 5, or more) further amino acid modifications, including for example amino acid substitution, deletion, insertion and/or addition. The further amino acid modification may be independently located at N-terminal, C-terminal and/or within internal portion of the Exendin sequence. The amino acid substituted, inserted and/or added may be any natural amino acid, non-natural amino acid or amino acid analog, or D- or L-stereoisomer. In some embodiments, the further amino acid modification is conserved amino acid substitution, for example substitution between Ala/Gly, Ser/Thr, Glu/Asp, Gln/Asn, Ala/Val/Ile/Leu, Arg/Lys, Phe/Tyr, etc.

The Exendin variant may be obtained by a number of methods known in the art, including such as recombinant preparation methods, chemical synthesis, etc.

In an embodiment, the Exendin variant is synthesized by solid phase peptide synthesis chemistry, and then purified in lab-scale, such as by single purification step on reverse phase HPLC column or other appropriate chromatography methods.

In another embodiment, the Exendin variant is produced by recombinant method, including for example expression in appropriate prokaryotic or eukaryotic cells, and then the Exendin variant according to the present invention is isolated by routine techniques. For example, the nucleic acid sequence encoding the peptide is firstly synthesized by chemical synthesis method, and the sequence is cloned into a proper expression vector for expression under the control of proper promoter. Alternatively, the nucleic acid sequence encoding the Exendin variant may be obtained from wild-type Exendin by mutagenesis such as PCR mutagenesis, and then the sequence is cloned into a proper expression vector for expression under the control of proper promoter. These techniques are well in the scope of abilities for the skilled person, and many teachings are present in the art.

The proper eukaryotic host cells include mammal cells, for example CHO, COS, HEK 293, BHK, SK-Hep and HepG2. The cells are preferably grown in the condition which is suitable for expression of the Exendin variant according to the present invention. With respect to the reagents and conditions for producing or isolating the Exendin variant according to the present invention, there is no particular limitation, and any known or commercial available system can be employed. In a preferable embodiment, the Exendin variant is obtained by the method which has been described in the art.

Many expression vectors may be used to prepare the Exendin and/or the variant thereof, which may be selected from the group consisting of eukaryotic and prokaryotic expression vectors. The prokaryotic expression vectors may include for example plasmids such as pRSET, pET and pBAD, etc., in which useful promoters include for example lac, trc, trp, recA or araBAD etc. The eukaryotic expression vectors include (i) vectors used for expression in yeasts, such as pAO, pPIC, pYES, pMET, in which promoters such as AOX1, GAP, GAL1, AUG1, etc. may be used; (ii) vectors used for expression in insect cells such as pMT, pAc[delta], pIB, pMIB, pBAC, etc., in which promoters such as PH, p10, MT, Ac5, Op1E2, gp64, polh, etc. may be used; and (iii) vectors used for expression in mammal cells such as pSVL, pCMV, pRc/RSV, pcDNA3, pBPV, etc., and vectors derived from virus systems, such as vaccinia virus, adeno-associated virus, herpes virus, retroviruses, etc., in which promoters such as CMV, SV40, EF-1, UbC, RSV, ADV, BPV and β-actin may be used. In a preferred embodiment, the Exendin variant is expressed in the system of prokaryotic or eukaryotic cells, and the encoding sequences after codon optimization are used. In a preferred embodiment, the sequence for expressing the Exendin variant comprises leading peptide and/or signal peptide, in order to facilitate secretion of the Exendin variant from cells to extracellular followed by isolation and purification. In another preferred embodiment, the sequence for expressing the Exendin variant comprises no leading peptide and/or signal peptide. The Exendin variant is not secreted to extracellular region, and isolated and purified by cell lysis.

Exendin Variant Conjugates

The Exendin variant may be conjugated with one or more polymer moieties, forming a conjugate of Exendin variant. As used herein, the "polymer" is preferably physiologically acceptable, including polymers which is soluble in aqueous solution or suspension and have no negative effect such as side effect on mammals after applying the polymer-Exendin conjugate in a pharmaceutically effective amount. The polymers which can be used in the present invention have no particular limitation. Preferably, the polymers always have 2 to around 3000 repeated unit. The polymer moieties may be selected from natural or synthetic polymers, for example, including but not limited to for example polysaccharides, polyalkylene glycol, for example polyethylene glycol (PEG), polypropylene glycol (PPG), polyethylene oxide (PEO), copolymer of ethylene glycol and propylene glycol, polyvinyl alcohol, or any combination thereof. In a preferred embodiment, one or more PEG moieties are used for modification by conjugation in the conjugate of Exendin variant of the present invention.

In the present invention, the polymer is not limited to particular structure, and may be linear (such as alkoxy PEG or bifunctional PEG), branched or multi-armed (forked PEG or PEG linked to polyols core), dendritic or have degradable bond. In addition, the internal structure of polymer may be organized in any number of different patterns, which may be selected from the group consisting of homopolymers, alternating copolymers, random copolymers, block copolymers, alternating terpolymers, random terpolymers and block trimer. The polymer may further includes poly(alkylene oxide) polymers, poly-maleic acid, and poly (D, L-alanine).

In some embodiments, the polymer is polyethylene glycol (PEG) or derivatives thereof, such as methoxy polyethylene glycol (mPEG). As used herein, unless otherwise specified, polyethylene glycol (PEG) includes those with a hydroxyl terminal group and those with other terminal group. Said other terminal group includes but not limited to alkoxy, cycloalkoxy, cycloalkyloxy, alkenyl, aryloxy or arylalkyloxy. Such PEG molecules are all known in the art, and commonly used in modification of polypeptides. PEG side-chain may be linear, branched, forked or multi-armed. Different polyethylene glycol may have different length of polymerized chain and polymer structure.

The molecular weight of PEG used in the present invention is not particularly limited, which may be in the range of 0.1 to 200 kDa, such as 1 to 150 kDa, 2 to 100 kDa, 3 to 80 kDa or 4 to 50 kDa, may also be 5 to 40 kDa. A particularly useful PEG has the molecular weight in the range of 5 to 30 kDa. Some other useful PEG molecules comprise those disclosed in for example WO 03/040211, U.S. Pat. Nos. 6,566,506, 6,864,350 and 6,455,639. Particularly, the PEG has a general formula HO—$CH_2CH_2O$—$(CH_2CH_2O)_n$—$CH_2CH_2$—OH, in which n is in the range of about 5 to 4000. As described above, PEG used in the present invention includes PEG with other terminal groups, such as methoxy PEG, branched PEG, and forked PEG. Appropriate branched PEG may be prepared as described in U.S. Pat. No. 5,932,462, which is incorporated herein by reference in entirety. The branched PEG represents PEG which is branched at the site near terminal of polymer chain, and the main chain of branched PEG may be linear or branched.

As known by the skilled person, in biological active molecule conjugated with polymer moieties, the biological activity of the conjugated molecule decreases with increase of molecular weight of the polymer moieties (Bailon et al. Rational design of potent, long-lasting form of interferon: A 40 kDa branched polyethylene glycol-conjugated interferon α-2a for the treatment of hepatitis C. Bioconjugate Chem 2001; 12:195-202; Bowen et al. Relationship between molecular weight and duration of activity of polyethylene glycol conjugated granulocyte colony-stimulating factor mutein. Experimental Hematology 1999; 27:425-32; Bailon et al. PEG-modified biopharmaceuticals. Expert Opin Deliv. 2009; 6:1-16). As also known by the skilled person, the biological half-life and/or plasma half-life increases with increase of molecular weight of the polymer moieties.

However, it is surprisingly found that, in the present invention, the Exendin variant conjugate of the present invention still retains most of GLP-1 receptor agonist activity (such as in vivo activity) compared with un-conjugated Exendin variant, even if the molecular weight of polymer moieties (such as PEG) increases up to 30 kDa. Even if the molecular weight of PEG increases up to 40 kDa or more, the Exendin variant conjugate of the present invention still retains substantive GLP-1 receptor agonist activity (such as in vivo activity). Especially, when the molecular weight of PEG increases from 5 kDa to 27 kDa, GLP-1 receptor agonist activity of the Exendin variant conjugates remains substantially the same with that of un-conjugated Exendin variants.

In order to provide stable therapeutic effect in a long period and reduce dosing frequency for improving compliance of patients, it is desirable to prolong the biological half-life of the Exendin variant conjugate as much as possible while substantive activity of GLP-1 receptor agonist is retained. Accordingly, in an embodiment, the present invention provides an Exendin variant conjugate with prolonged biological half-life and substantive activity of GLP-1 receptor agonist.

In a specific embodiment, the molecular weight of the one or more polymer moieties (such as PEG) in the conjugate of Exendin variant is 2 kDa to 50 kDa, preferably 3 kDa to 40 kDa, more preferably 4 kDa to 35 kDa, further preferably 5 kDa to 30 kDa, such as 5 kDa, 10 kDa, 15 kDa, 20 kDa, 30 kDa and 40 kDa, as well as any value between any molecular weight value as above. It is noted that the molecular weight of polymer moieties conjugated to a conjugate of Exendin variant is calculated as overall molecular weight of all conjugated polymer moieties in the conjugate, if the conjugate comprises more than one conjugated polymer moieties, unless otherwise specified.

In a preferred embodiment, the molecular weight of the one or more polymer moieties (such as PEG) in the conjugate of Exendin variant is 20 kDa to 30 kDa, preferably 21 kDa to 29 kDa, more preferably 23 kDa to 27 kDa, for example 20 kDa, 21 kDa, 22 kDa, 23 kDa, 24 kDa, 25 kDa, 26 kDa, 27 kDa, 28 kDa, 29 kDa, 30 kDa, as well as any value between any molecular weight value as above.

The polymer used in the present invention is known in the prior art, which can be obtained by various means, including for example commercial means, such as CarboMer, Inc., J. T. Baker, The Dow Chemical Company, etc., alternatively prepared by known methods in the art, such as those described in EP1245608. The present invention is not limited to polymers prepared by any specific methods.

In the conjugate according to the present invention, the at least one polymer can be coupled with Exendin through amino group, carboxy group, hydroxyl group and/or thiol group, etc. in the Exendin. Such groups are often located at α-amino, α-carboxy and side-chain of amino acid residue such as lysine, aspartate, glutamate, cysteine, etc.

In some embodiments, one or more polymer molecules are coupled with an Exendin variant through thiol of cysteine in the Exendin variant. Modification by polymer such as polyethylene glycol on thiol of cysteine residue in proteins may increase the selectivity of modification, since there are a number of reagents which is specifically reactive with thiol and useful thiol in proteins is much less than free amino such as lysine residue.

Accordingly, in a preferred embodiment, the one or more polymer moieties may be conjugated on a cysteine residue of Exendin variant, more preferably conjugated on a cysteine residue of Exendin variant by thioether.

Preferably, the Exendin variant has one or more cysteine substitution at positions corresponding to position 20, position 25, position 35 and/or position 39 of wild-type exendin-3 or exendin-4, and the Exendin variant is linked to polymer such as polyethylene glycol through thiol group. More preferably, the Exendin variant has a cysteine substitution at positions corresponding to position 35 and/or position 39 of wild-type exendin-3 or exendin-4. Most preferably, the Exendin variant has a cysteine substitution at positions corresponding to position 39 of wild-type exendin-3 or exendin-4.

In a specific embodiment, the polymer moiety is conjugated with cysteine residue in the Exendin variant according to the present invention through thiol ether bond. For example, with respect to polyethylene glycol molecule with a maleimide activating group, a thiol ether bond may be formed between alkenyl of maleimide and thiol of cysteine, so as to conjugate one or more polyethylene glycol moieties to cysteine residue of the Exendin variant according to the present invention. In some other embodiments, PEGylation of cysteine residues may be carried out by such as PEG-vinyl sulfone, PEG-iodoacetamide or PEG-pyridine disulfide. A number of methods for conjugating polymer moieties such as PEG to polypeptides are present in the prior art, and all these methods can be used in the present invention.

As used herein, "PEGylated Exendin", "PEG modified Exendin" or "Exendin variant-PEG conjugate" comprises Exendin variant conjugated with one or more PEG. As used herein, "PEGylation" or "PEG modification" comprises conjugating one or more PEG moieties with Exendin. An appropriate PEGylation method is disclosed in for example U.S. Pat. Nos. 5,122,614 and 5,539,063, in which all the disclosed PEGylation methods are incorporated herein by reference in entirety.

In some embodiments, the conjugate has a structure of formula I as below:

$$\text{RPEG}-\text{X}-\underset{\underset{Y}{|}}{\text{CH}}-\text{Z-Exendin} \quad (I)$$

in which, Exendin represents the Exendin variant according to the present invention, Y is H or RPEG-X-, and each X and Z independently are linker, PEG represents $-(OCH_2CH_2)_n-$, n is a positive integer, R represents terminal group of PEG, preferably each R is independently selected from the group consisting of hydrogen, alkyl, cycloalkyl, cycloalkylalkyl, alkenyl, aryl or arylalkyl.

In some specific embodiments, the alkyl may be C1-C6 alkyl, preferably C1-C4 alkyl, such as methyl, ethyl, N-propyl, isopropyl, butyl, isobutyl and tert-butyl; the cycloalkyl may be C3-C7 cycloalkyl, such as cyclopropyl, cyclobutyl, cyclopentyl, cyclohexyl and cycloheptyl; the cycloalkylalkyl may be cycloalkyl C1-C4 alkyl, such as cycloalkylmethyl and cycloalkylethyl, including cyclohexylmethyl and cyclohexylethyl, etc., the aryl may be phenyl, methylphenyl and naphthyl, etc., the arylalkyl may be phenylmethyl, phenylethyl and naphthylmethyl, naphthylethyl, etc. PEG molecules with various terminal groups are known in the art, and these and other PEG molecules may be selected as desired. PEG molecules with required terminal group may be synthesized by known methods in the art as required.

In some embodiments, each "RPEG-" in formula I as described independently has a structure as below:

$$CH_3(CH_2)_k-(OCH_2CH_2)_n-, \quad (CH_3)_2CH-(OCH_2CH_2)_n-,$$

$$(CH_3)_3C-(OCH_2CH_2)_n-,$$

cyclohexyl-$CH_2-(OCH_2CH_2)_n-$, cyclohexyl-$(OCH_2CH_2)_n-$, phenyl-$CH_2-(OCH_2CH_2)_n-$ or phenyl-$(OCH_2CH_2)_n-$, in which, k and n are both integers, k=0, 1, 2, 3, 4, 5 or 6; n=40, 41, . . . , 45, 46, 47, 48, . . . , 1200.

In some other preferred embodiments, each "RPEG-" in formula (I) independently has a structure as below:

$$CH_3(CH_2)_k-(OCH_2CH_2)_n-, \quad (CH_3)_2CH-(OCH_2CH_2)_n-,$$

$$(CH_3)_3C-(OCH_2CH_2)_n-,$$

cyclohexyl-$CH_2-(OCH_2CH_2)_n-$, cyclohexyl-$(OCH_2CH_2)_n-$ or phenyl-$CH_2-(OCH_2CH_2)_n-$, in which, k and n are both integers, k=0, 1, 2 or 3; n=40, 41, . . . , 45, 46, 47, 48, . . . , 1200.

In some embodiments, each "—X—" in formula (I) independently has a structure as below:

$$-O-(CH_2)_p-\overset{O}{\underset{\|}{C}}-NH-(CH_2)_m- \quad \text{or} \quad -O-(CH_2)_m-,$$

in which, p and m are both integers, p=0, 1, 2, 3, 4, 5, 6, 7, 8, 9, 10, 11 or 12; m=0, 1, 2, 3, 4, 5, 6, 7, 8, 9, 10, 11 or 12.

In some other embodiments, each "—X—" in formula (I) independently has a structure as below:

$$-O-(CH_2)_p-\overset{O}{\underset{\|}{C}}-NH-(CH_2)_m- \quad \text{or} \quad -O-(CH_2)_m-,$$

in which, p and m are both integers, p=0, 1, 2, 3, 4 or 5; m=0, 1, 2, 3 or 4.

In some other embodiments, each "—Z-Exendin" in formula (I) independently has a structure as below:

maleimide-Exendin, $-NH-CH(COOH)-CH_2-C(O)-$Exendin or $-NH-C(O)-CH_2-CH(COOH)-$Exendin.

Preferably, "—Z-Exendin" in formula (I) has a structure as below:

—CH$_2$O—(CH$_2$)$_j$—N(succinimide)—Exendin,

—CONH—(CH$_2$)$_w$—N(succinimide)—Exendin,

—CH$_2$O—(CH$_2$)$_j$—NHCO—(CH$_2$)$_q$—N(succinimide)—Exendin,

—CONH—(CH$_2$)$_w$—NHCO—(CH$_2$)$_q$—N(succinimide)—Exendin,

—CH$_2$O—CO—(NH)$_i$—C$_6$H$_4$—N(succinimide)—Exendin,

—CH$_2$O—(CH$_2$)$_j$—NHCO—(NH)$_i$—C$_6$H$_4$—N(succinimide)—Exendin,

—CONH—(CH$_2$)$_w$—NHCO—(NH)$_i$—C$_6$H$_4$—N(succinimide)—Exendin,

—CH$_2$O—(CH$_2$)$_j$—NH—CH(COOH-CH$_2$-)—CO—Exendin,

—CH$_2$O—(CH$_2$)$_j$—NH—CO—CH$_2$—CH(COOH)—Exendin,

—CONH—(CH$_2$)$_w$—NH—CH(COOH-CH$_2$-)—CO—Exendin, or

—CONH—(CH$_2$)$_w$—NH—CO—CH$_2$—CH(COOH)—Exendin, in which, i, j, q, w are integers, i=0 or 1; j=1, 2, 3, 4, 5 or 6; q=1, 2, 3, 4, 5 or 6; w=1, 2, 3, 4, 5 or 6.

The conjugates of Exendin variant according to the present invention may be synthesized by any suitable method. A number of methods for conjugating polymer to proteins or peptides are known in the prior art, including incubating polymers (preferably activated polymers) with the Exendin variant according to the present invention. In an embodiment, the polymer is polyethylene glycol, which may be activated and conjugated to the Exendin variant by for example cyano bromide method, carbonyldiimidazole method, N-hydroxysuccinimide method, cyanuric chloride urea method, etc. Alternatively, PEG may be specifically conjugated to thiol of cysteine residue in the Exendin variant by PEG-vinyl sulfone, PEG-iodoacetamide or PEG-pyridine disulfide.

In some specific embodiments, the activated PEG may be incubated with the Exendin variant according to the present invention under the conditions below: pH 5.0-7.0, molar ratio of PEG to peptides is 1-10, 0.5-12 hr of reaction period, the temperature of reaction is 0-50° C., for example 2-40° C. or 4-37° C.

After the conjugation reaction, the conjugate may be isolated by suitable methods. The suitable methods include for example ultrafiltration, dialysis or chromatography, etc., which are all in the scope of abilities for the skilled person.

Pharmaceutical Composition

The Exendin variant and/or conjugate of the Exendin variant according to the present invention may have many uses, including for example reducing blood glucose. Thus, the present invention further provides a pharmaceutical composition for reducing blood glucose, comprising therapeutically effective amount of the Exendin variant and/or conjugate of the Exendin variant according to the present invention, as well as optionally a pharmaceutically acceptable carrier. Preferably, the pharmaceutical composition may be useful for treating diabetes, more preferably for treating Type 1 and/or Type 2 diabetes, in particular, preferably for treating Type 2 diabetes.

The therapeutically effective amount of the Exendin variant and/or conjugate of the Exendin variant according to the present invention is depended on administrating route, subject type and physical characteristics of specific mammal under consideration. These factors and the relationship between these factors and the determined amount are well known by the skilled person. The amount and the administrating route may be adjusted so as to achieve the optimal effect, resulting in delivery of peptides to the subject. However, it is depended on the known factors such as body weight, diet, concurrently administrated drug and other factors, which are well known by the skilled person in the field of medicine.

The pharmaceutical composition may be administrated in the combined treatment, i.e. the pharmaceutical composition is applied in combination with one or more other medications, in which they are applied together or in turn. In other embodiments, said other medications may be administrated before, during or after the administration of one or more the Exendin variant and/or conjugate of the Exendin variant according to the present invention or other pharmaceutical composition. Said other medication which is useful in the present invention comprise for example medication for reducing blood glucose, such as insulin, insulin analogues, dextrin agonists and cholecystokinin, and/or other compounds or composition which is used for treating diseases. Preferably, such combined dosing may achieve a combined or even synergistic effect.

As used herein, "pharmaceutically acceptable carrier" or "physiologically acceptable carrier" may be exchangeably used, including one or more of any and all physiologically compatible salts, solvents, dispensing medium, coating, antibacterial agents and antifungal agents, isotonic and absorption delaying agents, etc. In some embodiments, the carrier is suitable for intravenous, intramuscular, subcutaneous, spinal or epidermis dosing (such as by injection or infusion). Depending on the dosing routes, the therapeutic agent may be coated by certain material, in order to protect the therapeutic agent from acids and other natural condition which may inactivate the therapeutic agent.

When administrating, the pharmaceutical formulation according to the present invention is administrated in the pharmaceutical composition in a pharmaceutically acceptable amount. The term "pharmaceutically acceptable" intends to mean non-toxic substances which do not disturb the biological activity of active components. The formulation always contains salts, buffers, preservatives, compatible carrier and optionally other therapeutical agents, such as complementary immunity enhancers, including adjuvants, chemokines and cytokines. When used in the medication, the salt should be pharmaceutically acceptable, but non-pharmaceutically acceptable salt may be readily used for preparing pharmaceutically acceptable salt, thus they are not excluded from the scope of the present invention.

If required, the Exendin variant or the conjugate of the Exendin variant according to the present invention may be combined with a pharmaceutically acceptable carrier. As used herein, the term "pharmaceutically acceptable carrier" means one or more compatible solid or liquid fillers, diluents or packaging substances, which are suitable for applying to mammals such as human. The term "carrier" represents organic or inorganic, natural or synthetic components, which are combined with active components in order to facilitate application. The components of the pharmaceutical composition may be also mixed in the form in which the interaction significantly disrupting required efficacy of the medication is absent.

Preferably, the pharmaceutical composition according to the present invention may comprise buffer system, and preferably, the buffer system is acetate buffer solution with a pH of about 3.0 to about 6.0, or phosphate buffer solution with a pH of about 5.0 to about 9.0. In some specific embodiments, the suitable buffer comprises acetate, citrate, borate, phosphate.

Optionally, the pharmaceutical composition may also comprise a suitable preservative, such as benzalkonium chloride; chloride tert-butyl alcohol; parabens and thimerosal.

The pharmaceutical composition may be conveniently in the form of unit dose, and may be prepared by any well known method in the field of pharmaceutics. All the method comprises a step of combining the active agent with a carrier, and the carrier comprises one or more auxiliary components. Generally, the active agent and the liquid carrier, finely divided solid carrier or both are closely combined to prepare the composition, and if required, subsequently the product is shaped.

The pharmaceutical composition which is suitable for parenteral administration may be aseptic aqueous or non-aqueous formulation comprising one or more Exendin variant or conjugate of the Exendin variant. In some embodiments, the formulation is isotonic compared with the blood of subjects. A suitable dispension agent or wetting agent and suspension agent may be used for preparing the formulation according to known methods. The aseptic formulation for injection may also be aseptic solution or suspension for injection in non-toxic parenterally acceptable diluent or solvent, for example solution in 1,3-butanediol. Acceptable carriers and solvents which are useful comprise water, Ringer's solution and isotonic sodium chloride solution. In addition, aseptic non-volatile oil is routinely used as solvent or suspension medium. As such, any mild non-volatile oil may be used, comprising synthetic monoglyceride or diglyceride. In addition, fatty acid such as oleic acid may be used in formulation for injection. The formulation of carriers suitable for oral, subcutaneous, intravenous, intramuscular, etc. may be found in Remington's Pharmaceutical Sciences, Mack Publishing Co., Easton, Pa.

The Exendin variant or the conjugate of the Exendin variant according to the present invention may be prepared together with the carrier such as controlled release formulation including implants, transdermal patch and microcapsule delivering system, which protects the Exendin variant or the conjugate of the Exendin variant from rapid degrading. Biologically degradable, biologically compatible polymers, such as ethylene vinyl acetate, poly anhydrides, polyglycolic acid, collagen, polyorthoesters and poly lactic acid may be useful. A number of methods for preparing such formulation are known in the art, see for example Sustained and Controlled Release Drug Delivery Systems, J. R. Robinson, ed., Marcel Dekker, Inc., New York, 1978, etc.

The pharmaceutical composition according to the present invention may be administrated by any conventional route, including injection or infusion over time. For example, the administration may be carried out through oral, intravenous, intraperitoneal, intramuscular, intracavity, intra-tumor, or transdermal.

The pharmaceutical composition according to the present invention is administrated in an effective amount. "an effective amount" is the amount of any Exendin variant or conjugate of the Exendin variant provided herein, which produce desirable response (for example reducing the level of blood glucose in the subject) separately or together with other therapeutical agent. This may comprise merely temporarily delaying the development of diabetes, and alternatively, in some embodiments, this may comprise permanently terminating the development of diabetes.

Such amount certainly depends on the specific disease to be treated, the severity of diseases, personal parameters of patients (including age, physiological condition, height and weight), duration of treatment, properties of the concurrently ongoing treatment (if any), the specific administration routes and similar factors within the knowledge for health care professionals. These factors are well known for the skilled person, and readily informed through conventional experiments. Generally, the maximum dose for each component or combination thereof is preferably used, and that is, the highest safe dose determined according to reasonable medical reason. However, the skilled person may understand that patients may request lower dose or allowable dose based on medical, psychological or substantially any other reasons.

The pharmaceutical composition used in the previous methods is preferably aseptic, and comprises an effective amount of Exendin variant or conjugate of the Exendin variant in a weight unit or volume unit suitable for administrating to patients, which is separate or combined with another formulation, in order to produce required response, such as reducing the blood glucose.

The dose of Exendin variant or conjugate of the Exendin variant administrated to subjects may be selected according to different parameters, in particular administration route which is used and the condition of the subject. Other factors comprise required period of treatment. If the response in the subject is not sufficient at the applied original dose, higher dose may be applied to a range allowed by the tolerance degree of the patient (or achieve effectively higher dose through a different delivery route which is more local).

In some embodiments, the pharmaceutical composition comprises 0.20 mg/ml~5 mg/ml Exendin variant and/or comprises 4 mg/ml~40 mg/ml conjugate of the Exendin variant, preferably 0.20 mg/ml~5 mg/ml Exendin variant and/or comprises 4 mg/ml~40 mg/ml conjugate of the Exendin variant, more preferably 0.5 mg/ml~2 mg/ml Exendin variant and/or comprises 10 mg/ml~20 mg/ml conjugate of the Exendin variant. In general, the range of dose of the Exendin variant or the conjugate of the Exendin variant according to the present invention may be about 10 μg/kg body weight of a patient to about 100,000 μg/kg body weight of a patient. In some embodiments, the range of dose may be about 0.1 mg/kg to about 20 mg/kg. In other embodiments, the range of dose may be about 0.1 mg/kg to 5 mg/kg, 0.1 mg/kg to 10 mg/kg, or 0.1 mg/kg to 15 mg/kg. In other embodiments, the range of dose may be about 1 mg/kg to 5 mg/kg, 5 mg/kg to 10 mg/kg, 10 mg/kg to 15 mg/kg, or 15 mg/kg to 20 mg/kg. In other embodiments, the dose may be about 0.1 mg/kg, 0.5 mg/kg, 1 mg/kg, 2 mg/kg, 3 mg/kg, 5 mg/kg, 7 mg/kg, 10 mg/kg, 12 mg/kg, 15 mg/kg, 17 mg/kg, 20 mg/kg, 25 mg/kg or 30 mg/kg. In another embodiment, the dose may be about 1 mg/kg, 3 mg/kg, 5 mg/kg or 6 mg/kg. Based on the composition, the dose may be continuously delivered (for example by continuous pump), or intermittently delivered in a cycle. In some embodiments, the dose of the Exendin variant or the conjugate of the Exendin variant according to the present invention may be 0.1 to 20 mg/kg or any value therein, when administered intravenously. The desirable interval between multiple dosing of the particular composition may be determined by the skilled person without undue experimentation. Other protocols for dosing of compositions provided herein are known by the skilled person, in which dose, dosing schedule, administration site, administration route, etc. may be different from those described above. In a embodiment, the dose is administered via intravenous route. In another embodiment, the protocol of administration is bolus intravenous dosing.

A kit comprising the Exendin variant or the conjugate of the Exendin variant (for example in a pharmaceutical composition) and instructions is also in the scope of the present invention. The kit may further comprise at least one other reagent, for example one or more other medication for reducing blood glucose. In another embodiment, the kit may comprise a base, which is compacted in order to tightly accommodate one or more container means or a series of container means (such as test tube, tube, flask, bottle, syringe, etc.). The components of the kit may be packed in aqueous medium or be in lyophilized form.

The composition as provided herein may be in lyophilized form or provided in aqueous medium.

Preferably, the subject is vertebrate. More preferably, the subject is mammal. Most preferably, the subject is human. However, the subject may be other animal, such as home animal (for example dog, cat, etc.), domestic animal (for example cattle, sheep, pig, horse, etc.) or experiment animal (for example monkey, rat, mouse, rabbit, guinea pig, etc.).

The Exendin variant and/or the conjugate of the Exendin variant according to the present invention may be applied separately. However, it is preferably applied as a pharmaceutical composition, which always comprises suitably pharmaceutical excipient, diluent or carrier selected depending on intended administration route. They may be applied to patients/subjects in need thereof by any suitable means. The precise dose will depend on various factors, including the precise properties of the Exendin variant and the conjugate of the Exendin variant.

Some suitable administration routes comprise (but not limit to) oral, rectal, nasal, local (comprising buccal and sublingual), subcutaneous, virginal or perennial (comprising subcutaneous, intramuscular, intravenous, intradermis, intrathecal and epidural) administration.

In some embodiments, the pharmaceutical composition according to the present invention comprises an isotonic agent and/or preservative, preferably the isotonic agent is one or more of sucrose, mannitol, sodium chloride and glycerol, and the preservative is selected from the group consisting of m-cresol, benzyl alcohol, methyl p-hydroxybenzoateparabens, ethyl p-hydroxybenzoate, propyl p-hydroxybenzoate and butyl p-hydroxybenzoate. The skilled person in the art is able to prepare suitable solution of the Exendin variant or the conjugate of the Exendin variant according to the present invention, by employing for example isotonic excipient such as physiological saline, Ringer's solution or lactate Ringer's solution, etc. As required, a stabling agent, buffering agent, antioxidant and/or other additive may be added. The pharmaceutical composition for oral administration may be in the form of tablet, capsule, powder or oral liquid, etc. The tablet may comprise solid carrier, such as gelatin or an adjuvant. The liquid pharmaceutical composition always comprises liquid carrier, such as water, petroleum, animal oil or plant oil, mineral oil or synthetic oil. It may also comprise physiological saline, solution of glucose or other carbohydrate, or diols, such as ethylene glycol, propylene glycol or polyethylene glycol. In some embodiments, the pharmaceutical composition is in the form of liquid formulation and/or lyophilized formulation. Preferably the lyophilized formulation comprises lyophilization protectant. More preferably, the lyophilization protectant is selected from the group consisting of sucrose, lactose, mannitol, trehalose, and other carbohydrates.

The Exendin variant and/or the conjugate of the Exendin variant are preferably administrated to subjects in a "therapeutically effective amount" or "effective amount". The composition is preferably administrated to subjects in a "therapeutically effective amount", and the therapeutically effective amount or effective amount is sufficient to exhibit profits to the subjects. The actual amount of administration, and the rate and process of administration will depend on the own condition and severity of subjects to be treated. Prescription for treatment (such as determining the dose, etc.) is determined by the medical professionals, in view of diseases to be treated, personal condition of patients, delivering site, administration method, and other factors known by physicians.

In some embodiments, the range of dose for the Exendin variant and/or the conjugate of the Exendin variant may be 30 mg/kg body weight/day to 0.00001 mg/kg body weight/day, or 3 mg/kg/day to 0.0001 mg/kg/day, or 0.3 mg/kg/day to 0.01 mg/kg/day.

The present invention further provides a method for treating disease, comprising administrating a therapeutically effective amount of the Exendin variant and/or the conjugate of the Exendin variant to subjects in need thereof. In some embodiments, the disease is selected from the group consisting of: postprandial dumping syndrome, postprandial hyperglycemia, impaired glucose tolerance, obesity, eating disorders, insulin resistance syndrome, diabetes and hyperglycemia. In a preferred embodiment, the disease is Type 2 diabetes.

As well known, the Exendin may reduce body weight of obesity patients and induce nausea and vomiting, of which the mechanism is associated with inhibition of feeding center in center nervous system and activation of vomiting center (Larsen. Mechanisms behind GLP-1 induced weight loss. Br J Diabetes Vasc Dis 2008; 8: S34-S41; Schick et al. Glucagonlike peptide 1 (7-36)-amide acts at lateral and medial hypothalamic sites to suppress feeding in rats. Am J Physiol Regul Integr Comp Physiol 2003; 284: R1427-35). The conjugates of Exendin or the variants thereof cannot pass blood-brain barrier due to increased molecular weight, and thus reduce vomiting induced by the Exendin. Accordingly, the applicant expected the conjugates of Exendin or the variants thereof would also reduce the effects of the Exendin in reducing eating and body weight mediated by central nervous system, before the start of the present invention. However, the applicant surprisingly found that the conjugates of Exendin or the variants thereof significantly enhance the effects of reducing body weight and eating, although wild-type Exendin and un-conjugated Exendin variants both reduce body weight and eating.

Thus, in another aspect, the present invention provides a method of reducing body weight by using the conjugates of Exendin or the variants thereof and/or pharmaceutical composition comprising the same. In addition, the present invention also provides uses of the conjugates of Exendin or the variants thereof and/or pharmaceutical composition comprising the same in manufacturing a medicament for reducing body weight. In an embodiment, the conjugates of Exendin or the variants thereof is the conjugate of Exendin variant according to the present invention, as described above.

The present invention will be illustrated by the examples as below, but should not be interpreted as further limitation in any way. All references cited in the present application (including reference documents, granted patents, published patent application and co-pending patent application) are explicitly incorporated herein by reference in entirety. The reagents and materials used in the examples as below are commercial available products which are at least analytical pure or comparable level.

EXAMPLE

Serial number and brief description for Exendins, Exendin variants and conjugates thereof used in the examples are provided in the table below, in order to facilitate understanding the technical solutions in the following examples.
Serial Brief Description
No.
PB-101 wild-type Exendin-4, also called Exenatide
PB-102 Exendin-4, Cys substituted at position 35
PB-103 Exendin-4, Cys substituted at position 30
PB-104 Exendin-4, Cys substituted at position 25
PB-105 Exendin-4, Cys substituted at position 39
PB-106 PB-105, conjugated with PEG20000
PB-106b PB-105, conjugated with PEG20000, double-armed PEGb
PB-106c PB-105, conjugated with PEG20000, double-armed PEGc
PB-106d PB-105, conjugated with PEG20000, double-armed PEGd
PB-106e PB-105, conjugated with PEG20000, double-armed PEGe
PB-107 PB-105, conjugated with PEG30000
PB-108 PB-105, conjugated with PEG40000
PB-109 PB-105, conjugated with PEG20000×2, double-armed PEG
PB-109b PB-105, conjugated with PEG20000×2, double-armed PEGb
PB-109c PB-105, conjugated with PEG20000×2, double-armed PEGc
PB-109d PB-105, conjugated with PEG20000×2, double-armed PEGd
PB-110 PB-105, conjugated with PEG5000
PB-110b PB-105, conjugated with PEG5000b
PB-110c PB-105, conjugated with PEG5000c
PB-111 PB-105, Tyr added at C-terminal
PB-112 PB-111, conjugated with PEG20000
PB-113 PB-105, Gly at position 2 is substituted by dAla
PB-114 PB-113, conjugated with PEG40000
PB-119 PB-105, conjugated with PEG23000
PB-120 PB-105, conjugated with PEG27000

Example 1

Solid Phase Synthesis of Exendin-4 and Variants Thereof

Polypeptides synthesis is a conventional technique in the filed of biochemistry and pharmaceutics. Various types of polypeptides synthesizer are commercial available from a number of commercial organizations (such as GE Health-Care, Applied Biosystems Inc.), and many commercial organizations (such as Sangon Biotech (Shanghai) Co., Ltd., Shanghai Biocolor BioScience & Technolgy Company) provide services for custom polypeptide synthesis. For example, polypeptides with specified sequence can be synthesized by a polypeptide synthesizer using the following procedure.

The Exendin-4 and the variants thereof with a thiol were synthesized by Fmoc amino group protection strategy using "Fmoc-Rinker Amide MBHA resin" type solid support. The first step: Fmoc protected amino acid in N,N-methylformamide (DMF) solvent was reacted for 1-5 hr using HBTU/DIPEA as condensing agent, and completeness of condensation reaction was monitored using ninhydrin method. The second step: reaction was carried out in DMF using 10-30% piperidine as de-protecting agent for 10-30 min, and completeness of deprotection of amino acid protection groups was monitored using ninhydrin method. The third step: the first and second steps were repeated using respective amino acid according to target polypeptide sequence, until the last amino acid in the sequence was coupled. The fourth step: the reaction was carried out using TFA as cleavage agent for 1-5 hr, in order to cleavage the polypeptides from the solid support and deprotect at the same time. The fifth step: the polypeptide solution after being cleaved was precipitated using ethyl ether and filtrated. The filtrate was collected. Then C18 type chromatography solemn was used for elution with 0.1% TFA/acetonitrile-water as mobile phase, and fractions were collected, lyophilized to obtain the product. The six step: the purity of the product was identified using HPLC method, and the structure of the product was determined by amino acid sequence analysis and mass spectrometry.

The applicant requested Chengdu Kaijie Biomedical science company to synthesize the polypeptides with sequences as below according to the above method:

PB-101: wild-type Exendin-4 with a amino acid sequence as below:

(SEQ ID NO: 1)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser;

PB-102: Exendin-4 variant with a amino acid sequence as below, in which position 35 at C-terminal is Cys:

(SEQ ID NO: 3)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Cys-Pro-

Pro-Pro-Ser;

PB-105: Exendin-4 variant with a amino acid sequence as below, in which position 39 at C-terminal is Cys:

(SEQ ID NO: 4)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Cys;

PB-103: Exendin-4 variant with a amino acid sequence as below, in which position 30 at C-terminal is Cys:

(SEQ ID NO: 5)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Cys-Pro-Ser-Ser-Gly-Ala-Pro-

Pro-Pro-Ser;

PB-104: Exendin-4 variant with a amino acid sequence as below, in which position 25 at C-terminal is Cys:

(SEQ ID NO: 6)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Cys-Leu-Lys-Asn-Gly-Gly-Pro-Ser-Ser-Gly-Ala-Pro-

Pro-Pro-Ser;

PB-111: Exendin-4 variant with a amino acid sequence as below, in which position 39 at C-terminal is substituted by Cys and linked with Tyr:

(SEQ ID NO: 7)
His-Gly-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Cys-Tyr;

and

PB-113: Exendin-4 variant with a amino acid sequence as below, in which Gly at position 2 of N-terminal is substituted by dAla and position 39 at C-terminal is substituted by Cys:

(SEQ ID NO: 8)
His-dAla-Glu-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Cys.

As an example, FIG. 1 provides the analysis results of mass spectrometry for PB-105, M+1 peak (mass weight+1) of PB-105 is 4203.3 Da determined by MALDI-TOF MS, which is corresponded with the theoretical mass weight (4202.8).

Example 2a

Preparation and Analysis of PB-110
(PEG5000-PB-105)

Figure 2:
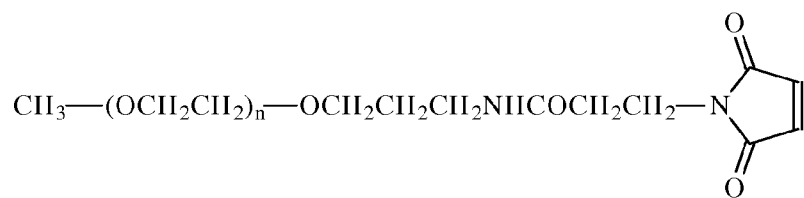
FIG. 2 shows a molecular structure of PEG.

2.0 mg of PB-105 was dissolved in 1 ml of 20 mM sodium phosphate buffer (pH 6.5), and 5 mg PEG5000 (supplied by PegBio Co., Ltd. (Suzhou), 5000 represents that the molecular weight of PEG is 5 kDa, and the molecular structure is shown in FIG. 2) was weighed according to a molar ratio of PEG to peptide being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml of 0.5M cysteine solution), and finally kept at −20° C. for further purification.

The sample was 5-fold diluted in 50 mM sodium acetate buffer (pH 4.5), and loaded onto SP ion exchange chromatographic column (XK16/20 column, macroCap SP packing, GE Inc.) balanced by 5-fold column volume of 50 mM sodium acetate buffer (pH 4.5). After loading, the column was balanced by 2-fold column volume of 50 mM sodium acetate buffer (pH 4.5), and the buffer was then linearly increased to 100% buffer B (50 mM sodium acetate buffer (pH 4.5) containing 1 M NaCl) in 20-fold column volumes. The elution peak was collected in AKTA Purifier. As determined, about 1 mg of the peptide was obtained.

Figure 3:
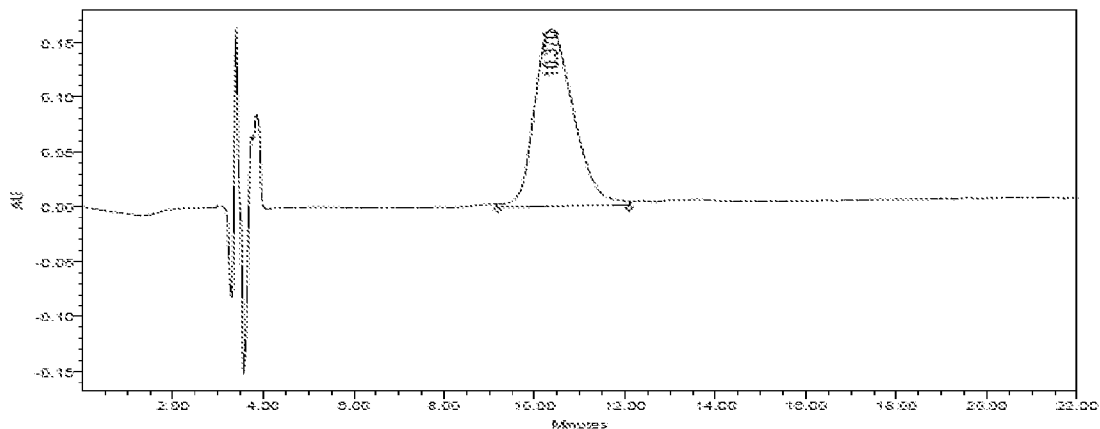
FIG. 3 shows purity analysis result of PB-110 (PEG5000-PB-105) obtained in Example 2 upon HPLC analysis.

As analyzed in an analytic HPLC (Agilent 1200) equipped with C4 reverse-phase analytical column with a pore size of 300 A (Jupiter C4 300 A 4.6*250 mm) and 0.1% TFA aqueous solution/0.1% TFA acetonitrile solution with a gradient from 61/39 to 54/46 (10 min). The sample was analyzed by analytical HPLC (Agilent1200), and the retention time was 10.4 min, the purity was 100% (see FIG. 3). GPC analysis was employed (SHIMADZU LC-20AD, SB-802 HQ/SB-803 HQ/SB-804 HQ three column tandem), under the condition of 0.1 M sodium nitrate solution, elution was carried out in a rate of 1.0 ml/min, and the purity was 97%.

Example 2b

Preparation and Analysis of PB-110b
(PEG5000b-PB-105)

Figure 4:
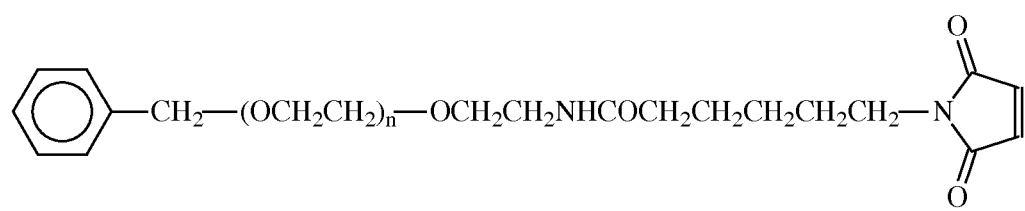
FIG. 4 shows the molecular structure of PEG5000b.

2.0 mg of PB-105 was dissolved in 1 ml of 20 mM sodium phosphate buffer (pH 6.5), and 5 mg of PEG5000b (supplied by PegBio Co., Ltd. (Suzhou), and the molecular structure is shown in FIG. 4) was weighed according to a molar ratio of PEG to peptides being 2:1 and added to the above solution. The solution was appropriately shaked in order to dissolve PEG and form a homogeneous mixture with the peptide. Other steps were the same with that in example 2a. Finally, GPC analysis was employed (SHIMADZU LC-20AD, SB-802 HQ/SB-803 HQ/SB-804 HQ three tandem columns, under the condition of 0.1 M sodium nitrate solution, elution was carried out in a rate of 1.0 ml/min), and the purity was determined as 96.7%.

Example 2c

Preparation and Analysis of PB-110c
(PEG5000c-PB-102)

Figure 5:
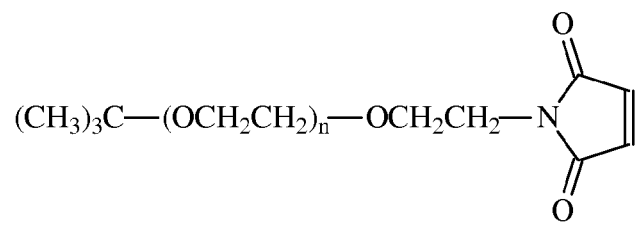
FIG. 5 shows the molecular structure of PEG5000c.

2.0 mg of PB-105 was dissolved in 1 ml of 20 mM sodium phosphate buffer (pH 6.5), and 5 mg of PEG5000c (supplied by PegBio Co., Ltd. (Suzhou), and the molecular structure is shown in FIG. 5) was weighed according to a molar ratio of PEG to peptides being 2:1 and added to the above solution. The solution was appropriately shaked in order to dissolve PEG and form a homogeneous mixture with the peptide. Other steps were the same as those in example 2a. Finally, GPC analysis was employed (SHIMADZU LC-20AD, SB-802 HQ/SB-803 HQ/SB-804 HQ three tandem columns, under the condition of 0.1 M sodium nitrate solution, elution was carried out in a rate of 1.0 ml/min), and the purity was determined as 97.8%.

Example 3a

Preparation and Analysis of PB-106
(PEG20000-PB-105)

2.0 mg of PB-105 was dissolved in 1 ml of 20 mM sodium phosphate buffer (pH 6.5), and 5 mg of PEG20000 (supplied by PegBio Co., Ltd. (Suzhou), 20000 represents 20 kDa of PEG molecular weight and the molecular structure is shown in FIG. 2) was weighed according to a molar ratio of PEG to peptides being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml of 0.5M cysteine solution), and finally kept at −20° C. for purification.

The sample was 5-fold diluted in 50 mM sodium acetate buffer (pH 4.5), and loaded onto SP ion exchange chromatographic column (XK16/20 column, macroCap SP packing, GE Inc.) balanced by 5-fold column volumes of 50 mM sodium acetate buffer (pH 4.5). After loading, the column was balanced by 2-fold column volumes of 50 mM sodium acetate buffer (pH 4.5), and the buffer was then linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 6:
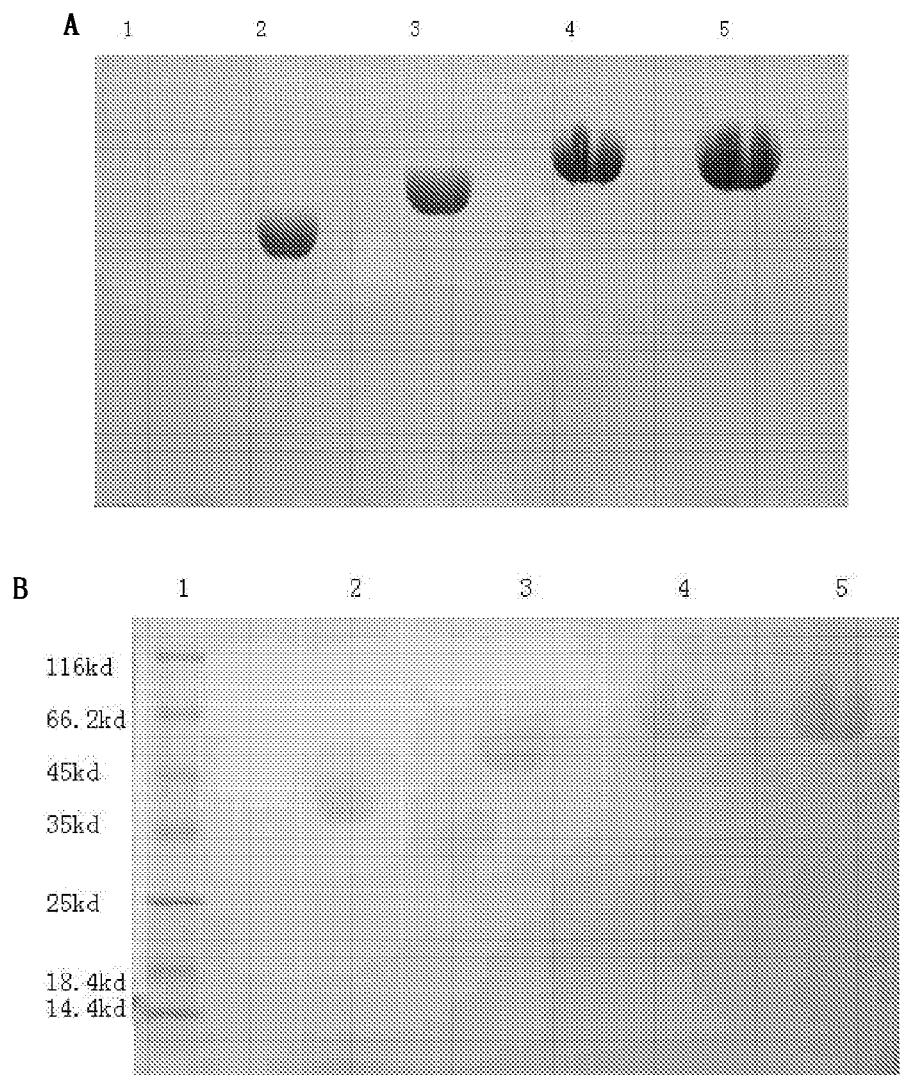
FIG. 6 shows (A) Iodine staining image and (B) Coomassie brilliant blue staining image of PEGylated PB-105 conjugate, with respective lanes: 1. molecular weight standard, 2. PB-106 (PEG20000-PB-105), 3. PB-107 (PEG30000-PB-105), 4. PB-108 (PEG40000-PB-105) and 5. PB-109 (PEG20000*2-PB-105).
Figure 7:
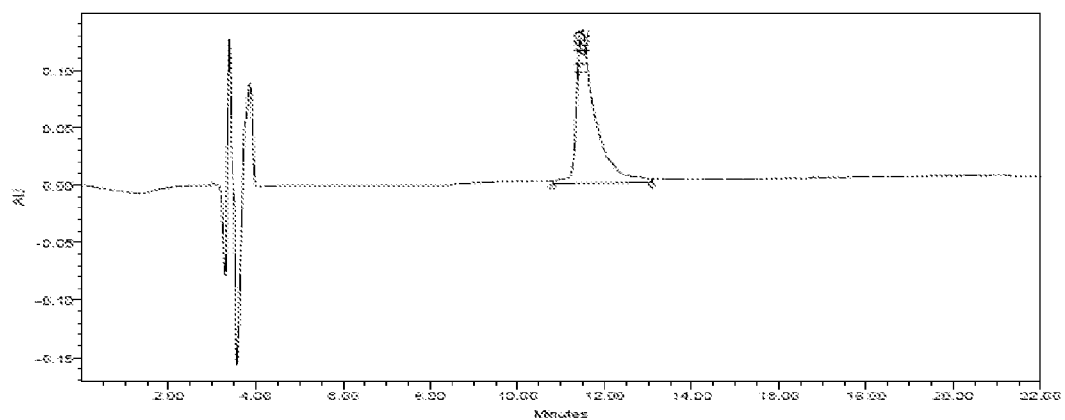
FIG. 7 shows purity analysis result of PB-106 (PEG20000-PB-105) obtained in Example 3 upon HPLC analysis.

The collected solution was detected by SDS-PAGE gel electrophoresis, and stained by Coomassie Brilliant Blue and iodo-staining (please see FIGS. 6A and 6B). The elution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC (Agilent1200), and the retention time was 11.5 min, the purity was determined as 100% (see FIG. 7). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.9%.

Example 3b

Preparation and Analysis of PB-106b
(PEG20000b-PB-105)

Figure 8:
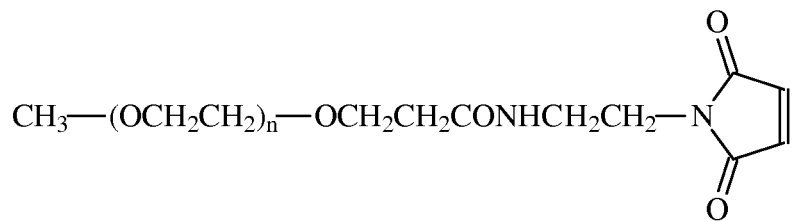
FIG. 8 shows the molecular structure of PEG20000b.

1.0 mg of PB-105 was dissolved in 1 ml of 20 mM sodium phosphate buffer (pH 6.5), and 2.5 mg of PEG20000b (supplied by PegBio Co., Ltd. (Suzhou), 20000 represents 20 kDa of PEG molecular weight and the molecular structure is shown in FIG. 8) was weighed according to a molar ratio of PEG to peptides being 2:1 and added to the above solution. The solution was appropriately shaked in order to dissolve PEG and form a homogeneous mixture with the peptide. The other steps were the same with that of Example 3a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.2%.

Example 3c

Preparation and Analysis of PB-106c
(PEG20000c-PB-105)

Figure 9:
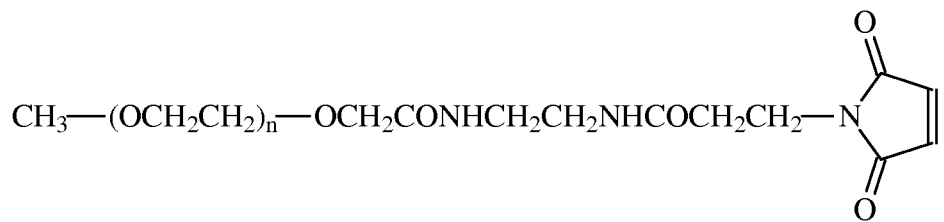
FIG. 9 shows the molecular structure of PEG20000c.

2.0 mg of PB-105 was dissolved in 1 ml of 20 mM sodium phosphate buffer (pH 6.5), and 20 mg of PEG20000c (supplied by PegBio Co., Ltd. (Suzhou), 20000 represents 20 kDa of PEG molecular weight and the molecular structure is shown in FIG. 9) was weighed according to a molar ratio of PEG to peptides being 2:1 and added to the above solution. The solution was appropriately shaked in order to dissolve PEG and form a homogeneous mixture with the peptide. The other steps were the same with that of Example 3a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 97.2%.

Example 3d

Preparation and Analysis of PB-106d
(PEG20000d-PB-105)

Figure 10:
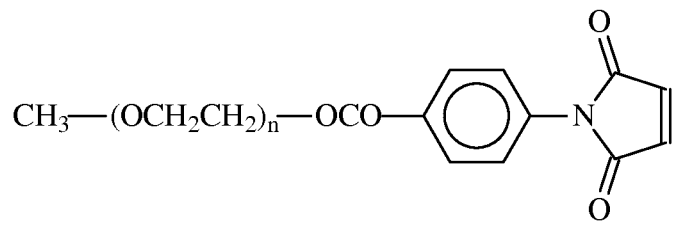
FIG. 10 shows the molecular structure of PEG20000d.

2.0 mg PB-105 was dissolved in 1 ml 20 mM phosphate buffer (pH 6.5), and 20 mg PEG20000c (supplied by PegBio Co., Ltd. (Suzhou), 20000 represents 20 kDa of PEG molecular weight and the molecular structure is shown in FIG. 10) was weighed according to a molar ratio of PEG to peptides being 2:1 and added to the above solution. The solution was appropriately shaked in order to dissolve PEG and form a homogeneous mixture with the peptide. The other steps were the same with that of Example 3a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 97.5%.

Example 3e

Preparation and Analysis of PB-106e
(PEG20000e-PB-105)

Figure 11:
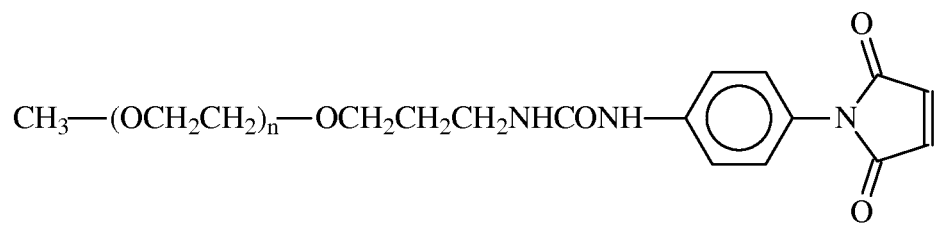
FIG. 11 shows the molecular structure of PEG20000e.

2.0 mg PB-105 was dissolved in 1 ml 20 mM phosphate buffer (pH 6.5), and 20 mg PEG20000e (supplied by PegBio Co., Ltd. (Suzhou), 20000 represents 20 kDa of PEG molecular weight and the molecular structure is shown in FIG. 11) was weighed according to a molar ratio of PEG to peptides being 2:1 and added to the above solution. The solution was appropriately shaked in order to dissolve PEG and form a homogeneous mixture with the peptide. The other steps were the same with that of Example 3a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 95.8%.

Example 3f

Preparation and Analysis of
PB-112(PEG20000-PB-111)

2.0 mg PB-111 was dissolved in 1 ml 20 mM phosphate buffer (pH 6.5), and 19 mg PEG20000 (supplied by PegBio Co., Ltd. (Suzhou), 20000 represents 20 kDa of PEG molecular weight and the molecular structure is shown in FIG. 2) was weighed according to a molar ratio of PEG to peptides being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 12:
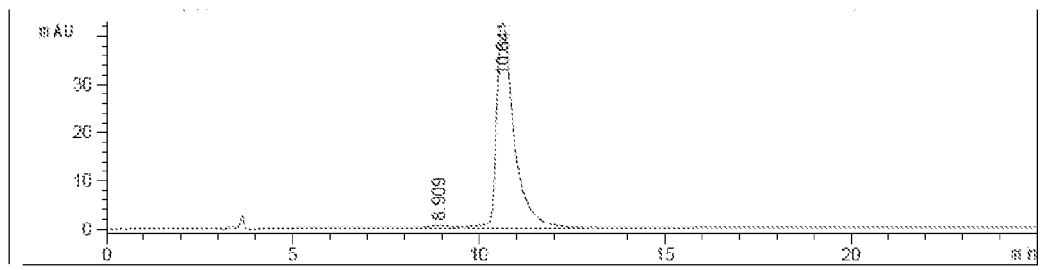
FIG. 12 shows purity analysis result of PB-112 (PEG20000-PB-111) obtained in Example 3 upon HPLC analysis.

The collected solution was eluted by C4 reverse-phase analytical column with a pore size of 300 Å (Jupiter C4 300 Å 4.6*250 mm) using 0.1% TFA aqueous solution/0.1% TFA acetonitrile solution with a gradient from 61/39 to 54/46 (10 min). The sample was analyzed by analytical HPLC, and the retention time was 10.6 min, the purity was determined as 98.5% (see FIG. 12). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.7%.

Example 4

Preparation and Analysis of PB-107
(PEG30000-PB-105)

2.0 mg PB-105 was dissolved in 1 ml 20 mM phosphate buffer (pH 6.5), and 30 mg PEG30000 (supplied by PegBio Co., Ltd. (Suzhou), 30000 represents 30 kDa of PEG molecular weight and the molecular structure is shown in FIG. 2) was weighed according to a molar ratio of PEG to peptides being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 13:
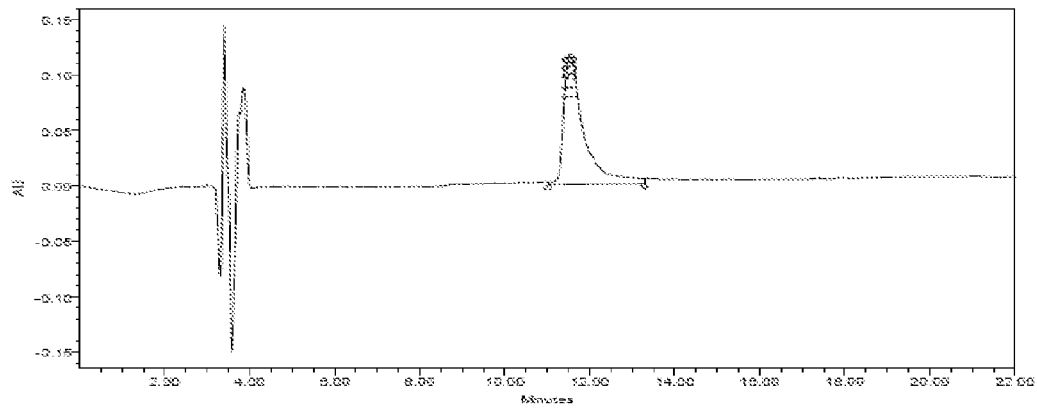
FIG. 13 shows purity analysis result of PB-107 (PEG30000-PB-105) obtained in Example 4 upon HPLC analysis.

The collected solution was detected by SDS-PAGE gel electrophoresis, and stained by Coomassie Brilliant Blue and iodo-staining (please see FIGS. 6A and 6B). The elution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC, and the retention time was 11.5 min, the purity was determined as 97.3% (see FIG. 13). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.7%.

Example 5a

Preparation and Analysis of PB-108
(PEG40000-PB-105)

2.0 mg PB-105 was dissolved in 1 ml 20 mM phosphate buffer (pH 6.5), and 40 mg PEG40000 (supplied by PegBio Co., Ltd. (Suzhou), 40000 represents 40 kDa of PEG molecular weight and the molecular structure is shown in FIG. 2) was weighed according to a molar ratio of PEG to peptides being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 14:
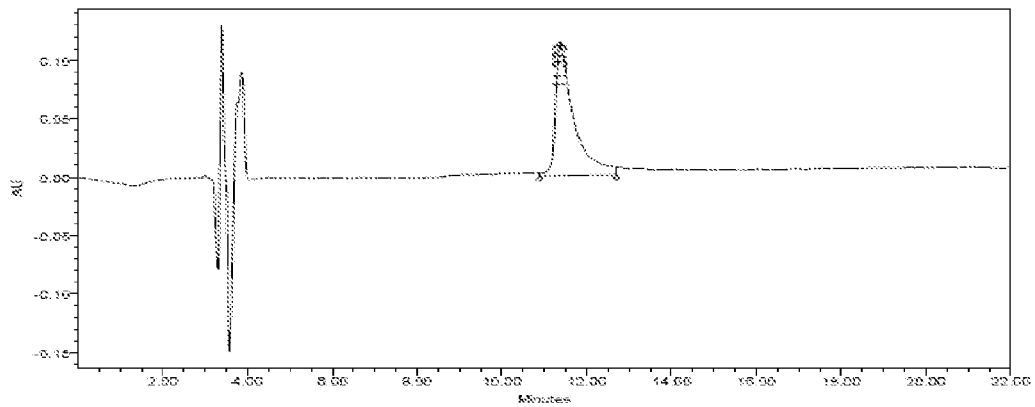
FIG. 14 shows purity analysis result of PB-108 (PEG40000-PB-105) obtained in Example 5 upon HPLC analysis.

The collected solution was detected by SDS-PAGE gel electrophoresis, and stained by Coomassie Brilliant Blue and iodo-staining (please see FIGS. 6A and 6B). The elution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC (Agilent 1200), and the retention time was 11.4 min, the purity was determined as 100% (see FIG. 14). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 97.2%.

Example 5b

Preparation and Analysis of PB-114(PEG40000-PB-113)

2.0 mg PB-113 was dissolved in 1 ml 20 mM phosphate buffer (pH 6.5), and 40 mg PEG40000 (supplied by PegBio Co., Ltd. (Suzhou), 40000 represents 40 kDa of PEG molecular weight and the molecular structure is shown in FIG. 2) was weighed according to a molar ratio of PEG to peptides being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 15:
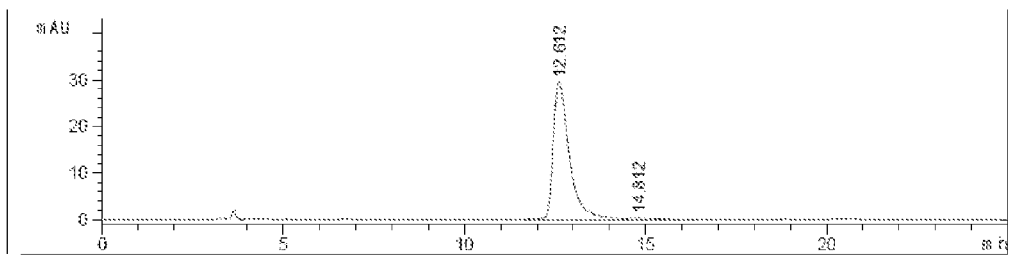
FIG. 15 shows purity analysis result of PB-114 (PEG40000-PB-113) obtained in Example 5 upon HPLC analysis.

The elution of collected solution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC, and the retention time was 12.6 min, the purity was determined as 97.9% (see FIG. 15). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.4%.

Example 6a

Preparation and Analysis of PB-109(PEG20000×2 (Double-Arm PEG)-PB-105)

Figure 16:
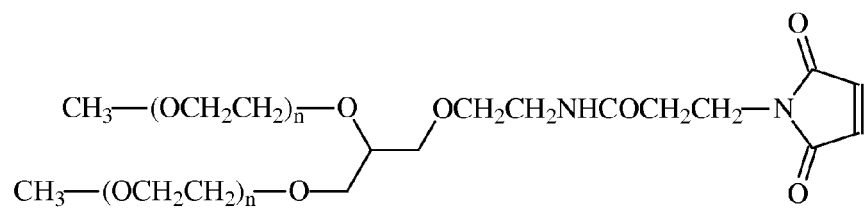
FIG. 16 shows the molecular structure of PEG20000×2.

2.0 mg PB-105 was dissolved in 1 ml 20 mM phosphate buffer (pH 6.5), and 40 mg PEG20000×2 (supplied by PegBio Co., Ltd. (Suzhou), 20000 represents 20 kDa of molecular weight of one arm in PEG and the molecular structure is shown in FIG. 16) was weighed according to a molar ratio of PEG to peptides being 2:1 and added to the above solution. The solution was appropriately shaked in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 17:
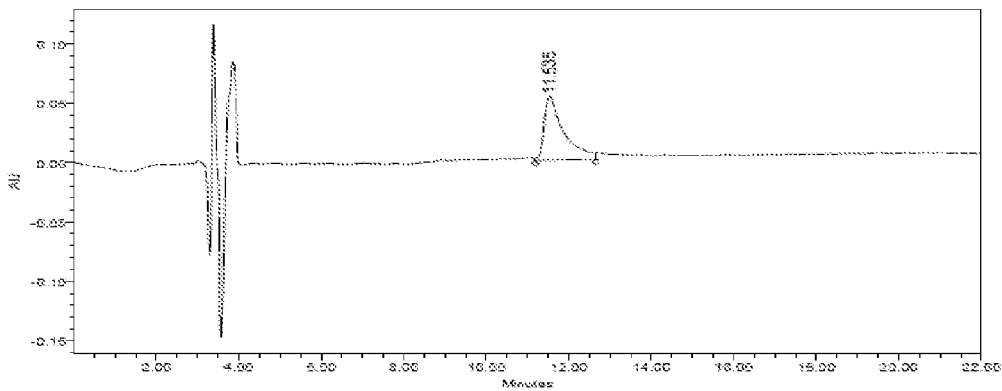
FIG. 17 shows purity analysis result of PB-109 (PEG20000*2-PB-105) obtained in Example 6 upon HPLC analysis.

The collected solution was detected by SDS-PAGE gel electrophoresis, and stained by Coomassie brilliant blue and iodo-staining (please see FIGS. 6A and 6B). The elution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC (Agilent 1200), and the retention time was 11.5 min, the purity was determined as 100% (see FIG. 17). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 99.3%.

Example 6b

Preparation and Analysis of PB-109b(PEG20000×2 (Double-Arm PEG)b-PB-105)

Figure 18:
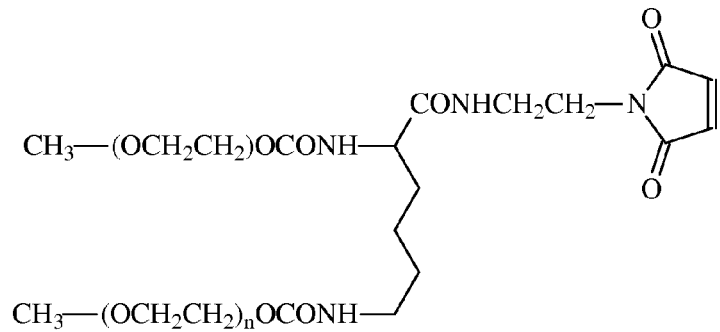
FIG. 18 shows the molecular structure of PEG20000×2b.

2.0 mg PB-105 was dissolved in 1 ml 20 mM phosphate buffer (pH 6.5), and 40 mg PEG20000×2b (supplied by PegBio Co., Ltd. (Suzhou), 20000×2 represents 20×2 kDa of molecular weight of PEG and the molecular structure is shown in FIG. 18) was weighed according to a molar ratio of PEG to peptides being 2:1 and added to the above solution. The solution was appropriately shaked in order to dissolve PEG and form a homogeneous mixture with the peptide. The other steps were the same with that in Example 6a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 99.2%.

Example 6c

Preparation and Analysis of PB-109c(PEG20000×2 (Double-Arm PEG)c-PB-105)

Figure 19:
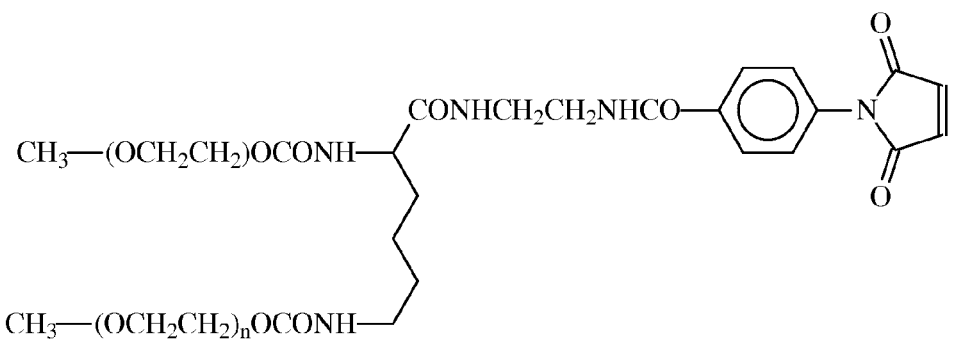
FIG. 19 shows the molecular structure of PEG20000×2c.

2.0 mg PB-105 was dissolved in 1 ml 20 mM phosphate buffer (pH 6.5), and 40 mg PEG20000×2c (supplied by PegBio Co., Ltd. (Suzhou), 20000×2 represents 20×2 kDa of molecular weight of PEG and the molecular structure is shown in FIG. 19) was weighed according to a molar ratio of PEG to peptides being 2:1 and added to the above solution. The solution was appropriately shaked in order to dissolve PEG and form a homogeneous mixture with the peptide. The other steps were the same with that in Example 6a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.8%.

Example 6d

Preparation and Analysis of PB-109d(PEG20000×2 (Double Armed PEG)d-PB-105)

Figure 20:
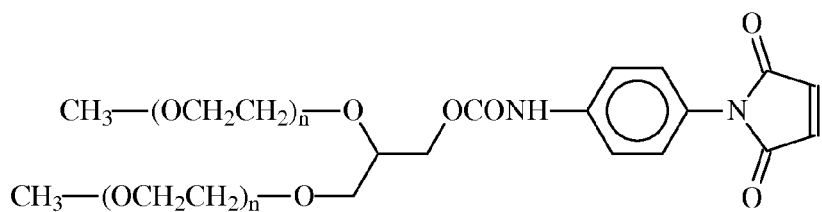
FIG. 20 shows the molecular structure of PEG20000×2d.

2.0 mg PB-105 was dissolved in 1 ml 20 mM phosphate buffer (pH 6.5), and 40 mg PEG20000×2d (supplied by PegBio Co., Ltd. (Suzhou), 20000×2 represents 20×2 kDa of molecular weight of PEG and the molecular structure is shown in FIG. 20) was weighed according to a molar ratio of PEG to peptides being 2:1 and added to the above solution. The solution was appropriately shaken in order to dissolve PEG and form a homogeneous mixture with the peptide. The other steps were the same with that in Example 6a. Finally, GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 99.2%.

Example 7

Preparation and Analysis of PB-119(PEG23000-PB-105)

2.0 mg PB-105 was dissolved in 1 ml 20 mM phosphate buffer (pH 6.5), and 22 mg PEG23000 (supplied by PegBio Co., Ltd. (Suzhou), 23000 represents 23 kDa of molecular weight of one arm in PEG and the molecular structure is shown in FIG. 2) was weighed according to a molar ratio of PEG to peptides being 2:1 and added to the above solution. The solution was appropriately shaken in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. About 1 mg polypeptides were obtained as determined.

Figure 21:
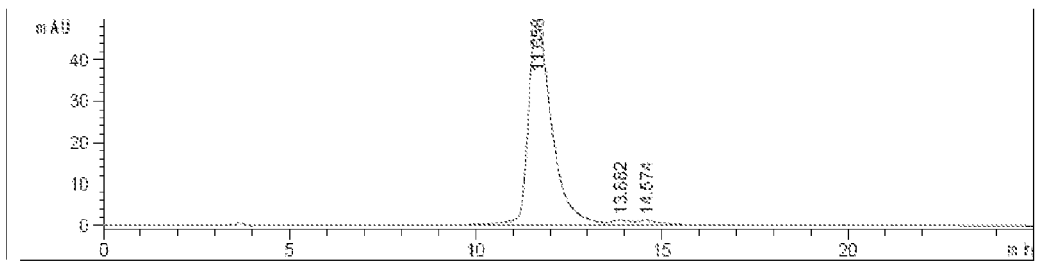
FIG. 21 shows purity analysis result of PB-119 (PEG23000-PB-105) obtained in Example 7 upon HPLC analysis.

The elution of collected solution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC (Agilent 1200), and the retention time was 11.6 min, the purity was determined as 96.0% (see FIG. 21). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 97.1%.

Example 8

Preparation and Analysis of PB-120(PEG27000-PB-105)

2.0 mg PB-105 was dissolved in 1 ml 20 mM phosphate buffer (pH 6.5), and 24 mg PEG27000 (supplied by PegBio Co., Ltd. (Suzhou), 27000 represents 27 kDa of molecular weight of one arm in PEG and the molecular structure is shown in FIG. 2) was weighed according to a molar ratio of PEG to peptides being 2:1 and added to the above solution. The solution was appropriately shaken in order to dissolve PEG and form a homogeneous mixture with the peptide. The reaction was carried out for 1 hour at 20° C. and stopped by excess cysteine solution (0.1 ml 0.5M cysteine solution), and finally kept at −20° C. for purification.

The sample was 5-fold diluted using 50 mM sodium acetate buffer (pH 4.5), and applied to SP ion exchange chromatographic column (GE, XK16/20 column, macroCap SP packing) balanced by 5-fold column volumes of 50 mM sodium acetate buffer (pH 4.5). After loading, the column was balanced by 2-fold column volumes of 50 mM sodium acetate buffer (pH 4.5), and linearly increased to 100% Buffer B (50 mM sodium acetate buffer (pH 4.5) containing 1 M NaCl) in 20-fold column volume. The elution peak was collected in AKTA Purifier. As determined, about 1 mg of the peptide was obtained.

Figure 22:
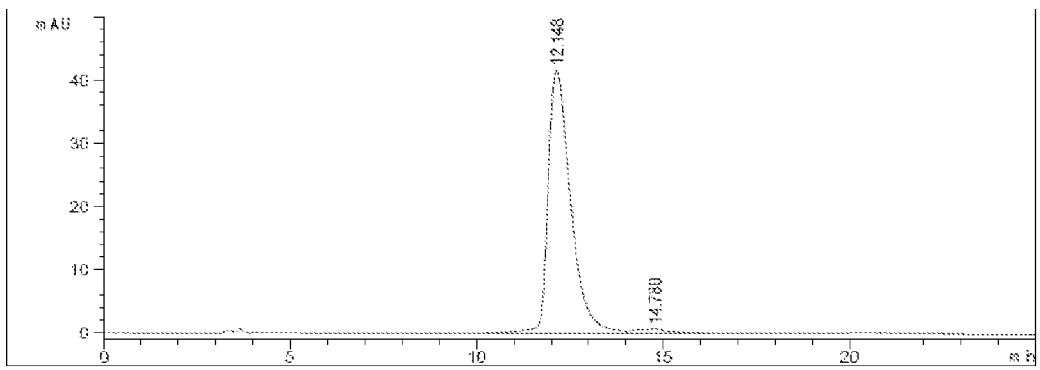
FIG. 22 shows purity analysis result of PB-120 (PEG27000-PB-105) obtained in Example 8 upon HPLC analysis.

The elution of collected solution was carried out using C4 reverse-phase analytical column with a pore size of 300 Å (Jupiter C4 300 Å 4.6*250 mm) and 0.1% TFA aqueous solution/0.1% TFA acetonitrile solution with a gradient from 61/39 to 54/46 (10 min). The sample was analyzed by analytical HPLC (Agilent 1200), and the retention time was 12.1 min, the purity was determined as 97.7% (see FIG. 22). GPC analysis was employed (SHIMADZU LC-20AD, SB-802 HQ/SB-803 HQ/SB-804 HQ three tandem columns), under the condition of 0.1 M sodium nitrate solution, elution was carried out in a rate of 1.0 ml/min, and the purity was determined as 98.4%.

Example 9

Stability Test for PB-105 Polyethylene Glycol Conjugates

Figure 23:
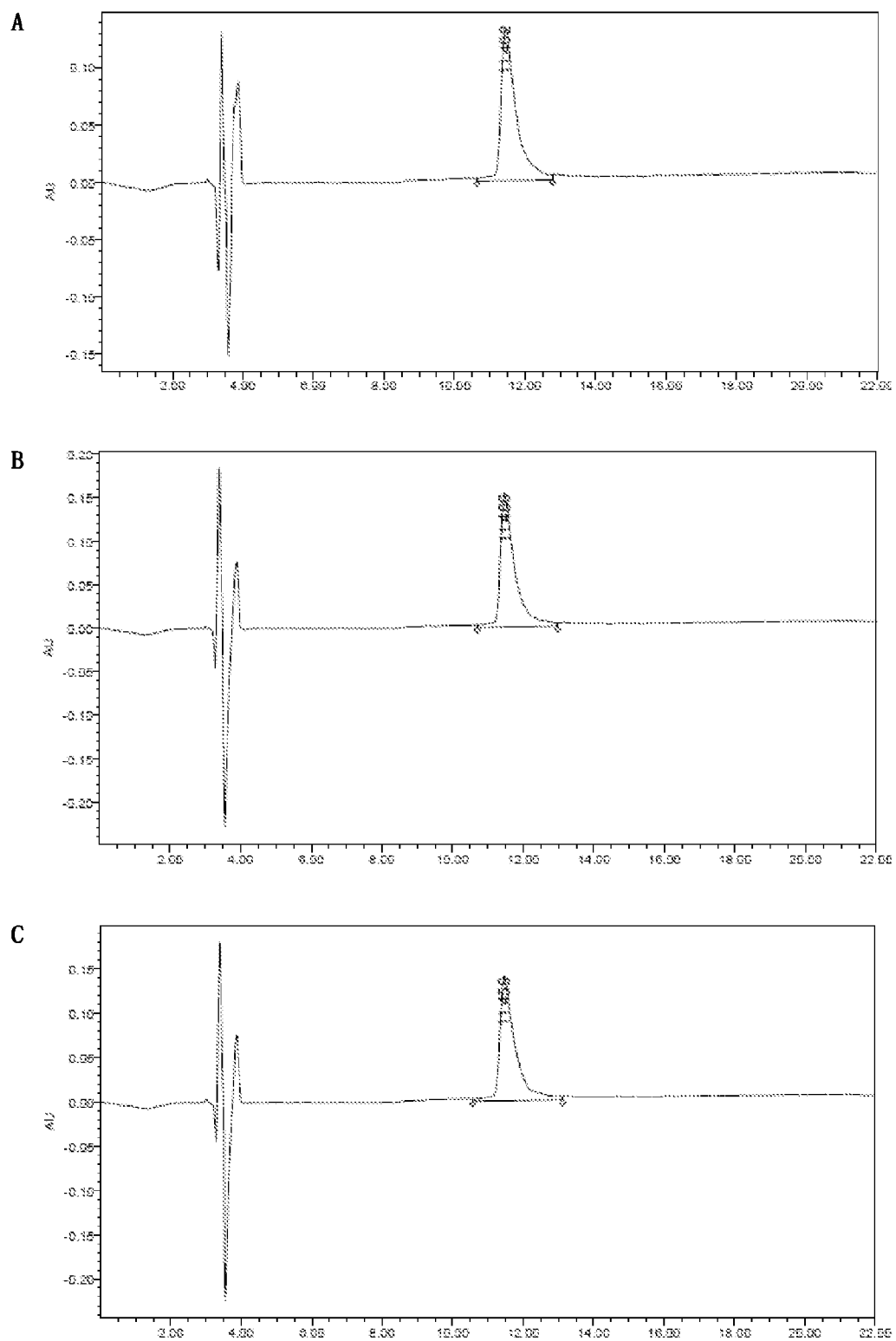
FIG. 23A shows HPLC analysis result of PB-106 (PEG20000-PB-105) stored at pH4.5, −20° C. for 60 days.
FIG. 23B shows HPLC analysis result of PB-106 (PEG20000-PB-105) stored at pH7.0, 4° C. for 60 days.
FIG. 23C shows HPLC analysis result of PB-106 (PEG20000-PB-105) stored at pH7.0, −20° C. for 60 days.

PB-110 (PEG5000-PB-105), PB-106 (PEG20000-PB-105), PB-107 (PEG30000-PB-105), PB-108 (PEG40000-PB-105) and PB-109 (PEG20000*2-PB-105) were respectively placed in sodium acetate buffer (pH 4.5) and phosphate buffer (pH 7.0) at 4° C. and −20° C., and evaluated for stability. Samples were taken for HPLC analysis at day 7, 15, 30, 60. The results for day 60 showed that the samples were stable at pH 4.5 and −20° C. (FIG. 23A), and at pH 7.0 and 4° C. or −20° C. (FIGS. 23B, 23C).

Example 10

In Vitro Effect of Pb-101 and Pb-105 on Intracellular cAMP Activity

PC12 cells were digested, seeded in 24-well plate at a density of $10^5$ cell/ml, and incubated for 48 hr (to 60-70% confluency). The culture medium was abandoned and washed twice using phosphate buffer (PBS). 1 ml PBS containing 1% BSA was added. Exendin-4 variant PB-101 and PB-105 ($10^{-11}$, $10^{-10}$, $10^{-9}$, $10^{-8}$, $10^{-7}$, and $10^{-6}$ M) with cysteine at position 39 of C-terminal were incubated with 3-isobutyl-1-methylxanthine (IBMX, final concentration of 100 μM) for 30 min. The incubation medium was abandoned. 500 μl HCl (0.1 M) was added to stop degradation of cAMP by the enzyme. The cells were collected and lysed by sonication. The protein content in cells was determined by BCA. The standard curve was plotted by setting a serials of groups of standards with different concentrations using cAMP enzyme-linked immuno kit (U.S. RD System corporation) instruction. Absorbances were determined at 450 nm in ELISA reader (U.S. Thermo Fisher Scientific Corporation) after reaction. The cAMP concentration was read in standard curve using such absorbance. Then, cAMP concentration in samples was calculated. Dose-response relationship for effect of PB-101 and PB-105 on increasing intracellular cAMP was calculated using Graphpad Prizm software.

Figure 24:
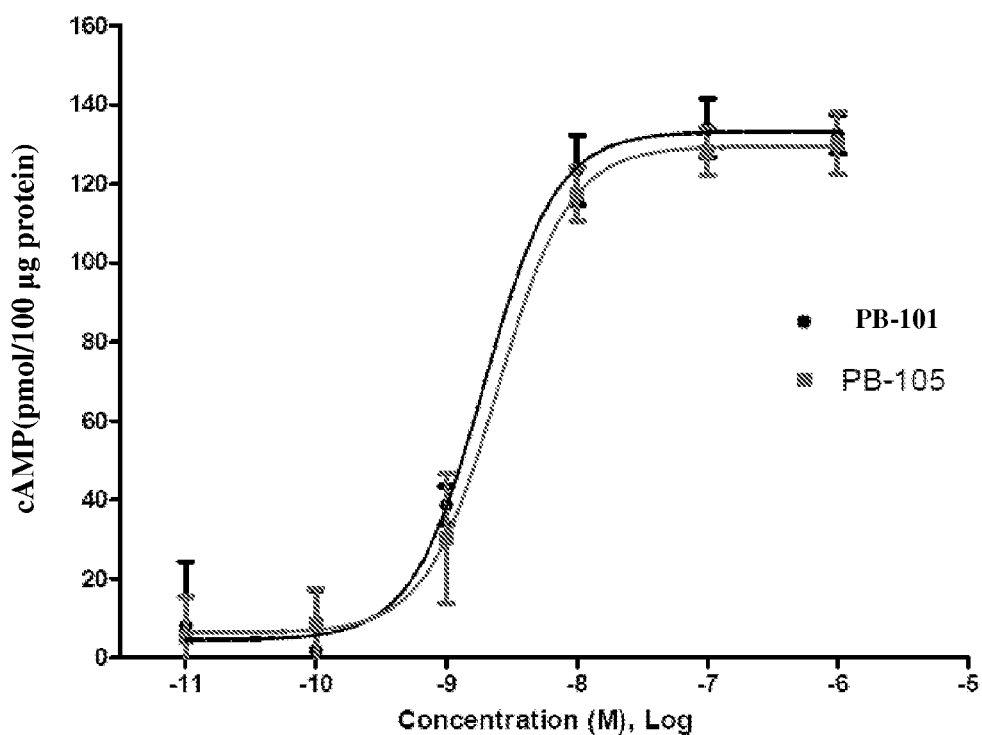
FIG. 24 shows dose-response relationship of effects of PB-101 and PB-105 on intracellular cAMP of PC12 cells.

The experimental results are shown in FIG. 24. PB-101 increased cAMP content in PC12 cells in a manner of dose-dependence, the maximum of increased cAMP ($E_{max}$) was 133.2±7.2 pmol/100 µg (protein), and $EC_{50}$ was $1.9 \times 10^{-9}$ M. PB-105 had a similar in vitro effect on cAMP in PC12 cells compared with PB-101. The maximum of increased cAMP ($E_{max}$) for PC-105 was 129.4±6.8 pmol/100 µg (protein) (PB-105 vs PB-101, P>0.05); $EC_{50}$ was $2.5 \times 10^{-9}$ M. The further analysis showed that Log $EC_{50}$ for PB-101 and PB-105 were respectively −8.71±0.15 and −8.61±0.15 (PB-105 vs PB-101, P>0.05). It indicated that the biological activity of PB-101 was not altered by introduction of cysteine (thiol) at position 39 of C-terminal.

Example 11

In Vitro Effect of Pb-105 and PEGylated Conjugates Thereof on Intracellular cAMP Activity PC12 cells were digested, seeded in 24-well plate at a density of $10^5$ cell/ml, and incubated for 48 hr (to 60-70% confluency). The culture medium was abandoned and washed twice using phosphate buffer (PBS). 1 ml PBS containing 1% BSA was added. PB-105, PB-105 PEGylated (PEG5000) conjugate (PB-110), PB-105 PEGylated (PEG20000) conjugate (PB-106), PB-105 PEGylated (PEG30000) conjugate (PB-107), PB-105 PEGylated (PEG40000) conjugate (PB-108) and PB-105 PEGylated (PEG20000×2, double-arm) conjugate (PB-109) ($10^{-11}$, $10^{-10}$, $10^{-9}$, $10^{-8}$, $10^{-6}$, and $10^{-5}$ M) were incubated with 3-isobutyl-1-methylxanthine (IBMX, final concentration of 100 µM) for 30 min. The incubation medium was abandoned. 500 µl HCl (0.1 M) was added to stop degradation of cAMP by the enzyme. The cells were collected and lysed by sonication. The protein content in cells was determined by BCA. The standard curve was plotted by setting a serials of groups of standards with different concentrations using cAMP enzyme-linked immuno kit (U.S. RD System corporation) instruction. Absorbances were determined at 450 nm in ELISA reader (U.S. Thermo Fisher Scientific Corporation) after reaction. The cAMP concentration was read in standard curve using such absorbance. Then, cAMP concentration in samples was calculated. Dose-response relationship for effect of PB-106, PB-107, PB-108, PB-109 and PB-110 on increasing intracellular cAMP was calculated using Graphpad Prizm software.

Figure 25:
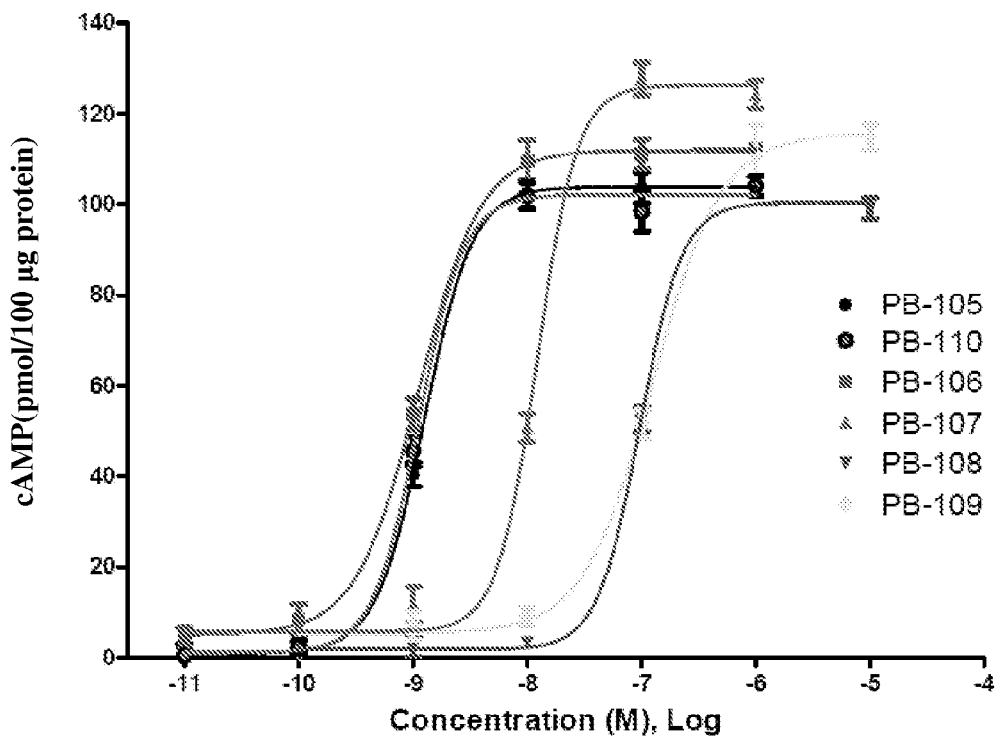
FIG. 25 shows effects of PB-105 and PEGylated conjugate thereof on intracellular cAMP activity in vitro.
Figure 26:
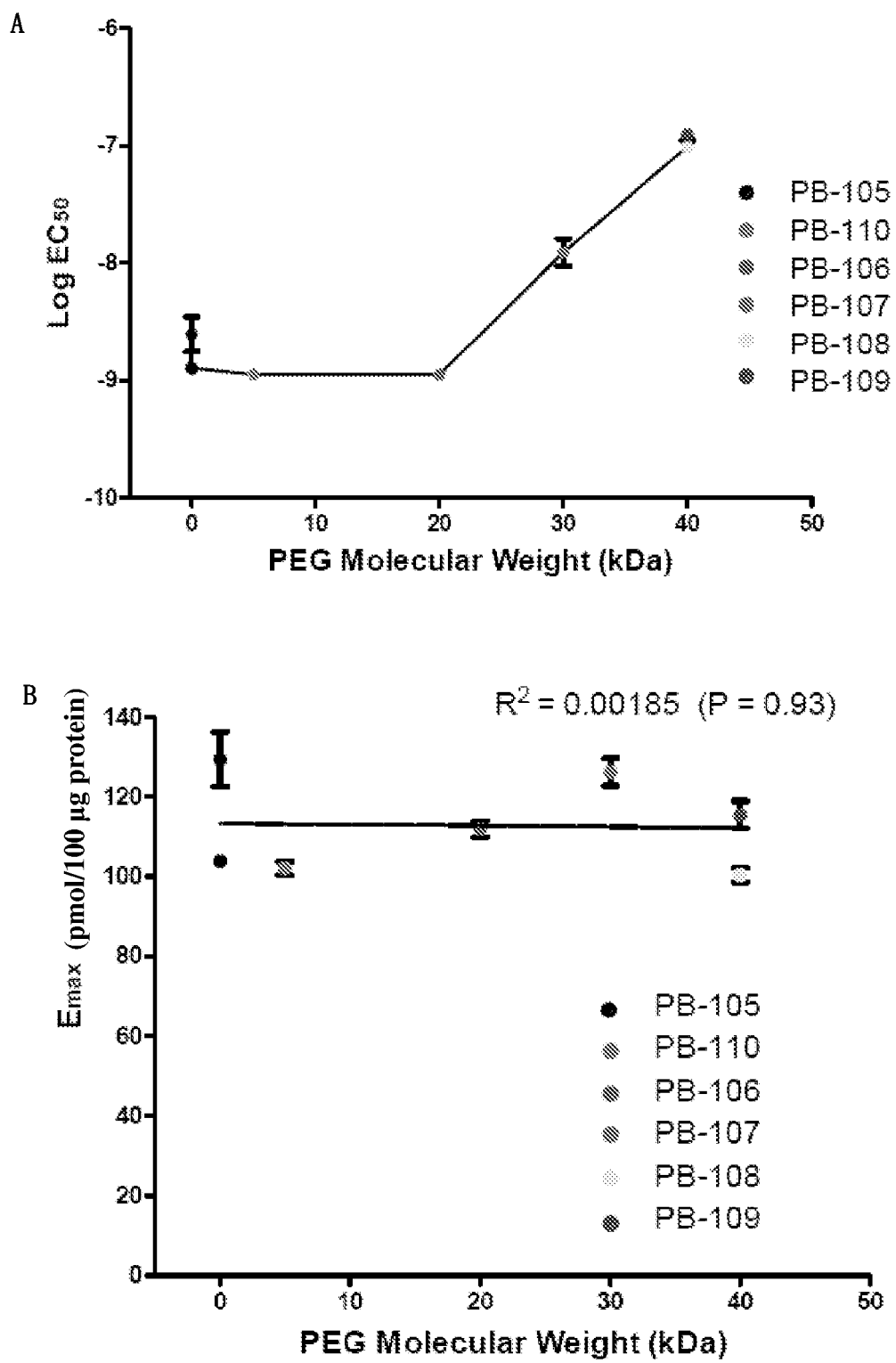
FIG. 26A shows relationship between MW of PEG in PEGylated conjugate and pharmacological activity in vitro (Log $EC_{50}$).
FIG. 26B shows relationship between MW of PEG in PEGylated conjugate and maximum pharmacological activity ($E_{max}$).

The experimental results indicated that PB-105 increased cAMP content in PC12 cells in a manner of dose-dependence, the maximum of increased cAMP ($E_{max}$) was 103.9±1.5 pmol/100 µg (protein), and $EC_{50}$ was $1.3 \times 10^{-9}$ M. PEGylation modification made the dose-response relationship curve move right in parallel in a manner of molecular mass-independence (5-40 kDa), and reduce the biological activity of PB-105 (FIG. 25). The $EC_{50}$ of PB-110, PB-106, PB-107, PB-108 and PB-109 were respectively $1.1 \times 10^{-9}$, $1.1 \times 10^{-9}$, $1.2 \times 10^{-8}$, $9.7 \times 10^{-8}$ and $1.3 \times 10^{-7}$ M. The PEGylation modification of 5 kDa (PB-110) and 20 kDa (PB-106) had nearly no effect on the activity of PB-105 (the activity was respectively 115% of that of PB-105), and 30 kDa (PB-107) and 40 kDa (including linear and double-arm, PB-108 and PB-109) PEGylation modification respectively reduced the activity of PB-105 by about 90% and 99%. The correlations between molecular weight of PEG in PEGylated conjugate and activities of these drugs (Log $EC_{50}$) are shown in FIG. 26A (including $EC_{50}$ of PB-105 in FIG. 24).

Example 12

In Vitro Effect of Pb-105 and PEGylated Conjugates Thereof on Intracellular cAMP Activity PC12 cells were digested, seeded in 24-well plate at a density of $10^5$ cell/ml, and incubated for 48 hr (to 60-70% confluency). The culture medium was abandoned and washed twice using phosphate buffer (PBS). 1 ml PBS containing 1% BSA was added. PB-105, PB-105 PEGylated (PEG23000) conjugate (PB-119) and PB-105 PEGylated (PEG27000) conjugate (PB-120 ($10^{-11}$, $10^{-10}$, $10^{-9}$, $3 \times 10^{-9}$, $10^{-8}$ and $10^{-7}$ M) were incubated with 3-isobutyl-1-methylxanthine (IBMX, final concentration of 100 µM) for 30 min. The incubation medium was abandoned. 500 µl HCl (0.1 M) was added to stop degradation of cAMP by the enzyme. The cells were collected and lysed by sonication. The protein content in cells was determined by BCA. The standard curve was plotted by setting a serials of groups of standards with different concentrations using cAMP enzyme-linked immuno kit (U.S. RD System corporation) instruction. Absorbances were determined at 450 nm in ELISA reader (U.S. Thermo Fisher Scientific Corporation) after reaction. The cAMP concentration was read in standard curve using such absorbance. Then, cAMP concentration in samples was calculated. Dose-response relationship for effect of PB-105, PB-119, and PB-120 on increasing intracellular cAMP was calculated using Graphpad Prizm software.

Figure 27:
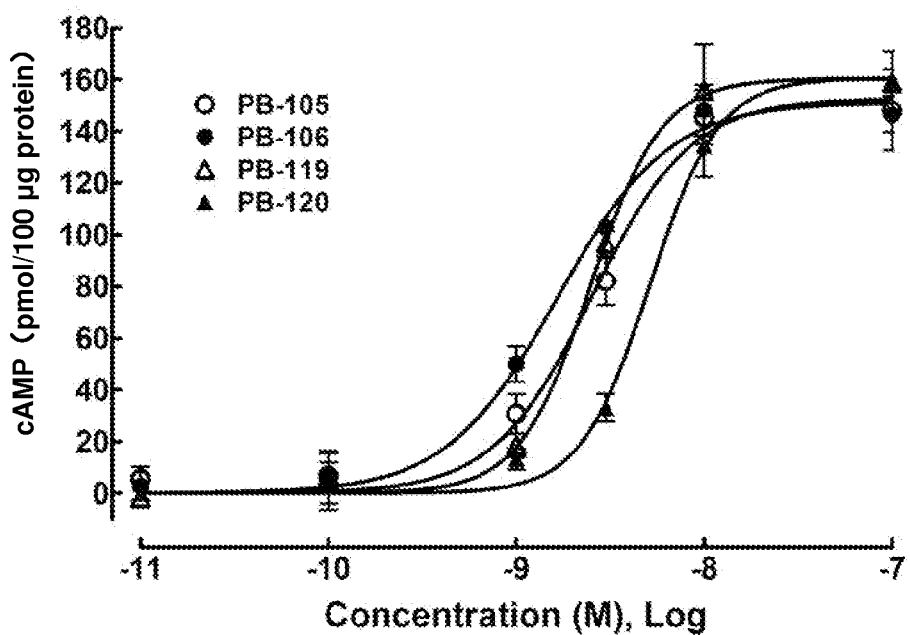
FIG. 27 shows effect of PB-105 and PEGylated conjugate thereof on intracellular cAMP activity in vitro.

The experimental results indicated that PB-105 increased cAMP content in PC12 cells in a manner of dose-dependence, and $EC_{50}$ was $2.7 \times 10^{-9}$ M. PB-106 (PEG20000) and PB-119 (PEG23000) had no effect on activity of PB-105 to cAMP, and PB-120 (PEG27000) made dose-response curve move right in parallel and reduce the biological activity of PB-105 to cAMP by about 50% (FIG. 27). The $EC_{50}$ of PB-106, PB-119 and PB-120 were respectively $1.5 \times 10^{-9}$, $2.5 \times 10^{-9}$ and $5.4 \text{xx} 10^{-9}$ M.

It is generally believed that the biological activity of conjugated biomolecule will exponentially reduce with increase of molecular weight of conjugated group (such as from 4 kDa) (Bailon et al. Rational design of potent, long-lasting form of interferon: A 40 kDa branched polyethylene glycol-conjugated interferon α-2a for the treatment of hepatitis C. Bioconjugate Chem 2001; 12:195-202; Bowen et al. Relationship between molecular weight and duration of activity of polyethylene glycol conjugated granulocyte colony-stimulating factor mutein. Experimental Hematology 1999; 27: 425-32; Bailon et al. PEG-modified biopharmaceuticals. Expert Opin Deliv. 2009; 6: 1-16). However, the applicant surprisingly found that, in FIGS. 25 and 27, the relationship between the molecular weight of conjugated polymer group and the activity of the conjugate of Exendin variant to in vitro stimulate cAMP does not completely accord to this expectation. At least for the conjugate of Exendin variant conjugated by PEG with a molecular weight of up to 23 kDa, PEGylation modification has no effect on action of the conjugate of Exendin variant to in vitro stimulate cells to produce cAMP (and when the molecular weight of PEG being up to 27 kDa, there is merely mild effect). In contrast, PEGylation modification has no effect on the maximum effect of PB-105 to stimulate the cAMP production ($E_{max}$). The $E_{max}$ of PB-110, PB-106, PB-107, PB-108 and PB-109 are respectively 102.1±1.8, 111.9±2.1, 126.2±3.4, 100.4±1.7 and 115.5±3.5 pmol/100 µg protein. The molecular weight of PEG in PEGylated conjugates has no correlation with $E_{max}$ of these drugs (see FIG. 26B) (including the $E_{max}$ of PB-105 in FIG. 24).

The inventor carried out the following analysis based on the surprising result. As medium containing serum in which a plenty of proteinase was present was not used as reaction system in this example and no proteinase was added in the solution of reaction, the enzymatic degradation of the Exendin variant and the conjugates thereof were significantly lower than in vivo. In other words, in the case of in vivo test with a longer action time, the degree of reduction for biological activity of the conjugates of the Exendin variant according to the present invention is less than unconjugated wild-type Exendin or Exendin variant, even the biological activity of the conjugates of the Exendin variant according to the present invention is higher. In another aspect, polymer moiety which is more than 23 kDa can be used to conjugate Exendin variant without significantly affecting in vivo biological activity. Although the present invention is not limited by this theory, the prediction is proved in the following examples.

Example 13

Time-Response Experiment of Hypoglycemic Effect for PB-101 and PB-105

Figure 28:
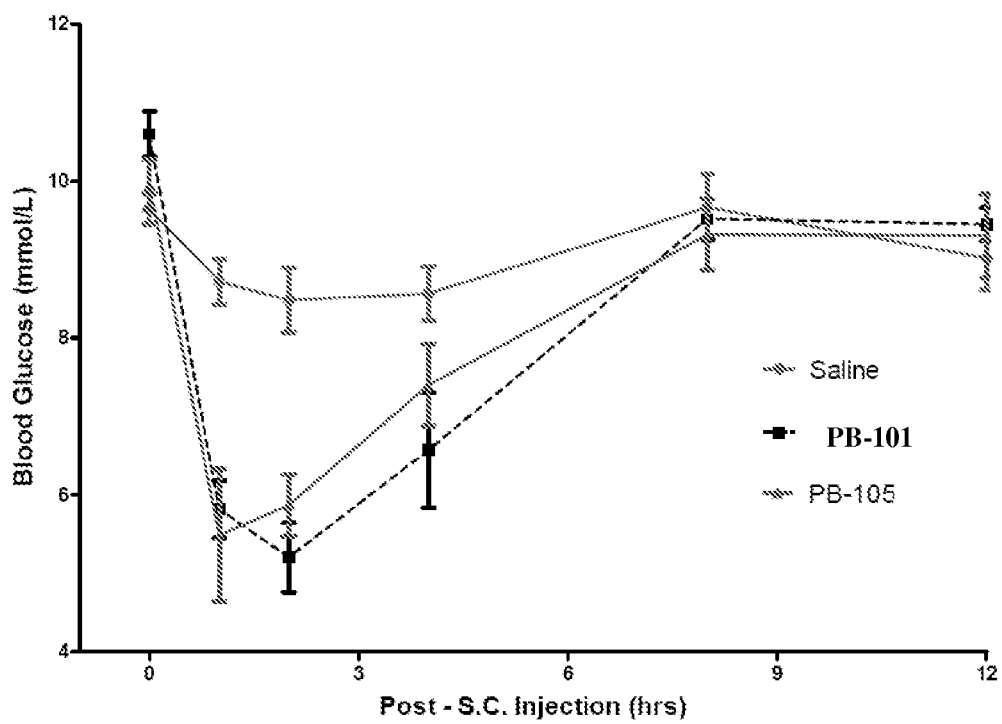
FIG. 28 shows time-response relationship of blood-glucose-reducing effect of PB-101 and PB-105.

Male Kunming mice (body weight was 27-32 g) were provided. The mice did not fast for food or water prior to the experiment. They were randomly distributed into three groups with six mice in each group. Equal volume of saline (10 ml/kg), PB-101 (10 µg/kg) and Exendin variant PB-105 (10 µg/kg) with a cysteine at position 39 of C-terminal were subcutaneously injected in bolus. At 0, 1, 2, 4, 8, 12 hr after injection, blood sampling in tail tip was carried out. Blood glucose was determined using One Touch blood glucose meter and testing strips accompanied (U.S. Johnson & Johnson). The time-response curve for hypoglycemic effect was plotted by using blood glucose value at different time points for y axis and using time points for x axis, so as to calculate biological half-life of hypoglycemic effects for PB-101 and PB-105. The result is shown in FIG. 28. The half-life of Exendin-4 variant substituted by cysteine and Exendin-4 are respectively 4.7±0.2 hrs and 4.4±0.2 hrs (PB-105 vs PB-101, P>0.05). It indicates that Exendin-4 variant substituted by cysteine at position 39 of C-terminal and Exendin-4 have comparable half-life.

Example 14

Dose-Response Experiment of Hypoglycemic Effect for PB-101 and PB-105

Figure 29:
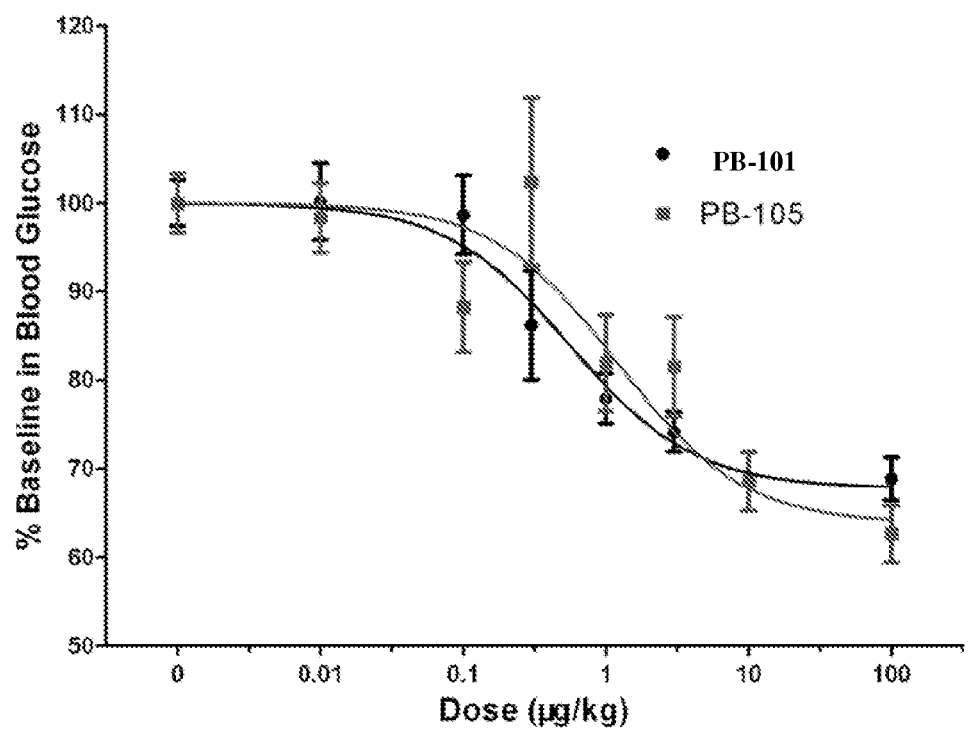
FIG. 29 shows dose-response relationship of blood-glucose-reducing effect of PB-101 and PB-105.

Male Kunming mice (body weight was 23-27 g) were provided. The mice fasted food 3 hrs but not for water prior to the experiment. They were randomly distributed into three groups with six mice in each group. Equal volume of saline (10 ml/kg), PB-101 (0.01, 0.1, 0.3, 1, 3, 10, 100 µg/kg) and Exendin variant PB-105 (0.01, 0.1, 0.3, 1, 3, 10, 100 µg/kg) with a cysteine at position 39 of C-terminal were subcutaneously injected in bolus. At 1 hr after injection, blood sampling in tail tip was carried out. Blood glucose was determined using OneTouch blood glucose meter and testing strips accompanied (U.S. Johnson & Johnson). The dose-response curve for hypoglycemic effect was plotted by using blood glucose value for y axis and using dose for x axis (FIG. 29). In turn, dose-response relationship parameter for PB-101 and PB-105 ($E_{max}$ and $ED_{50}$) was calculated using Graphpad Prizm software. The result indicated that the maximum hypoglycemic efficiency for polus injection of PB-101 and PB-105 were respectively 32.2% and 36.1%, $ED_{50}$ value were respectively 0.6 and 1.2 µg/kg. The further analysis indicated that Log $ED_{50}$ of PB-101 and PB-105 were respectively −0.25±0.17 and 0.08±0.20 (PB-105 vs PB-101, P>0.05). The experimental results indicated that Exendin-4 variant PB-105 with a cysteine at position 39 of C-terminal has no significantly difference with Exendin-4 in the term of hypoglycemic effect.

Example 15

Dose-Response Experiment of Hypoglycemic Effect for PB-101 and the Variant Thereof (PB-102)

Figure 30:
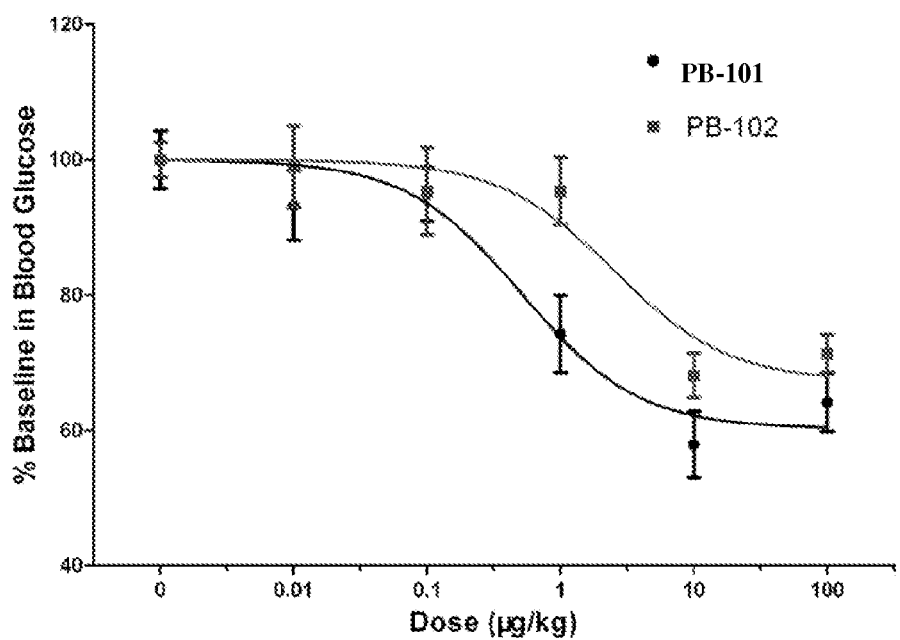
FIG. 30 shows dose-response relationship of blood-glucose-reducing effect of PB-101 and its variant PB-102.

Male Kunming mice (body weight was 22-26 g) were provided. The mice fasted for food 3 hrs but not for water prior to the experiment. They were randomly distributed into 18 groups with six mice in each group. Equal volume of saline (10 ml/kg), PB-101 (0.01, 0.1, 1, 10, 100 µg/kg) and Exendin variant PB-102 (0.01, 0.1, 1, 10, 100 µg/kg) with a cysteine at position 35 of C-terminal were subcutaneously injected in bolus. At 1 hr after injection, blood sampling in tail tip was carried out. Blood glucose was determined using OneTouch blood glucose meter and testing strips accompanied (U.S. Johnson & Johnson). The dose-response curve for hypoglycemic effect was plotted by using blood glucose value for y axis and using dose for x axis (FIG. 30). In turn, dose-response relationship parameter for PB-101 and PB-102 ($E_{Max}$ and $ED_{50}$) was calculated using Graphpad Prizm software. The result indicated that the maximum hypoglycemic efficiency for polus injection of PB-101 and PB-102 were respectively 39.8% and 32.8%, $ED_{50}$ value were respectively 0.5 and 2.5 µg/kg. The further analysis indicated that Log $ED_{50}$ of PB-101 and PB-105 were respectively −0.2867±0.2272 and 0.4015±0.2946 (PB-102 vs PB-101, P>0.05). The experimental results indicated that Exendin-4 variant PB-102 with a cysteine at position 35 of C-terminal has no significantly difference with Exendin-4 in the term of hypoglycemic effect.

Example 16

Figure 31:
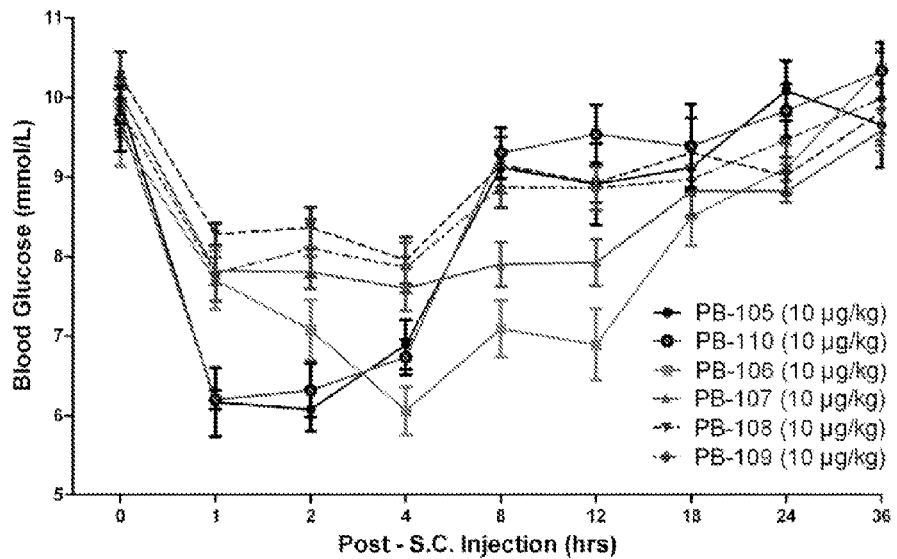
FIG. 31 shows time-response relationship of blood-glucose-reducing effect of PB-105 and the PEGylated conjugate thereof.
Figure 32:
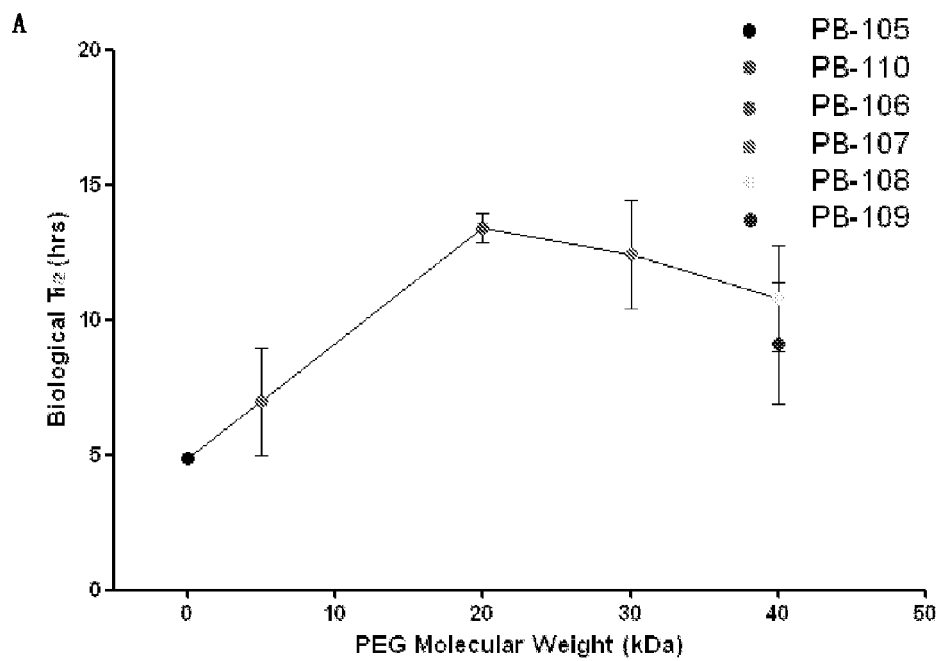
FIG. 32A shows relationship between molecular weight of PEG in PEGylated Exendin variant and biological half-life ($T_{1/2}$).
FIG. 32B shows relationship between molecular weight of PEG in PEGylated Exendin variant and maximum glucose-reducing effect (% pre-dosing blood glucose concentration).
FIG. 32C shows relationship between MW of PEG in PEGylated Exendin variant and Area Above Curve (AAC) of glucose-reducing curve.
Figure 32:
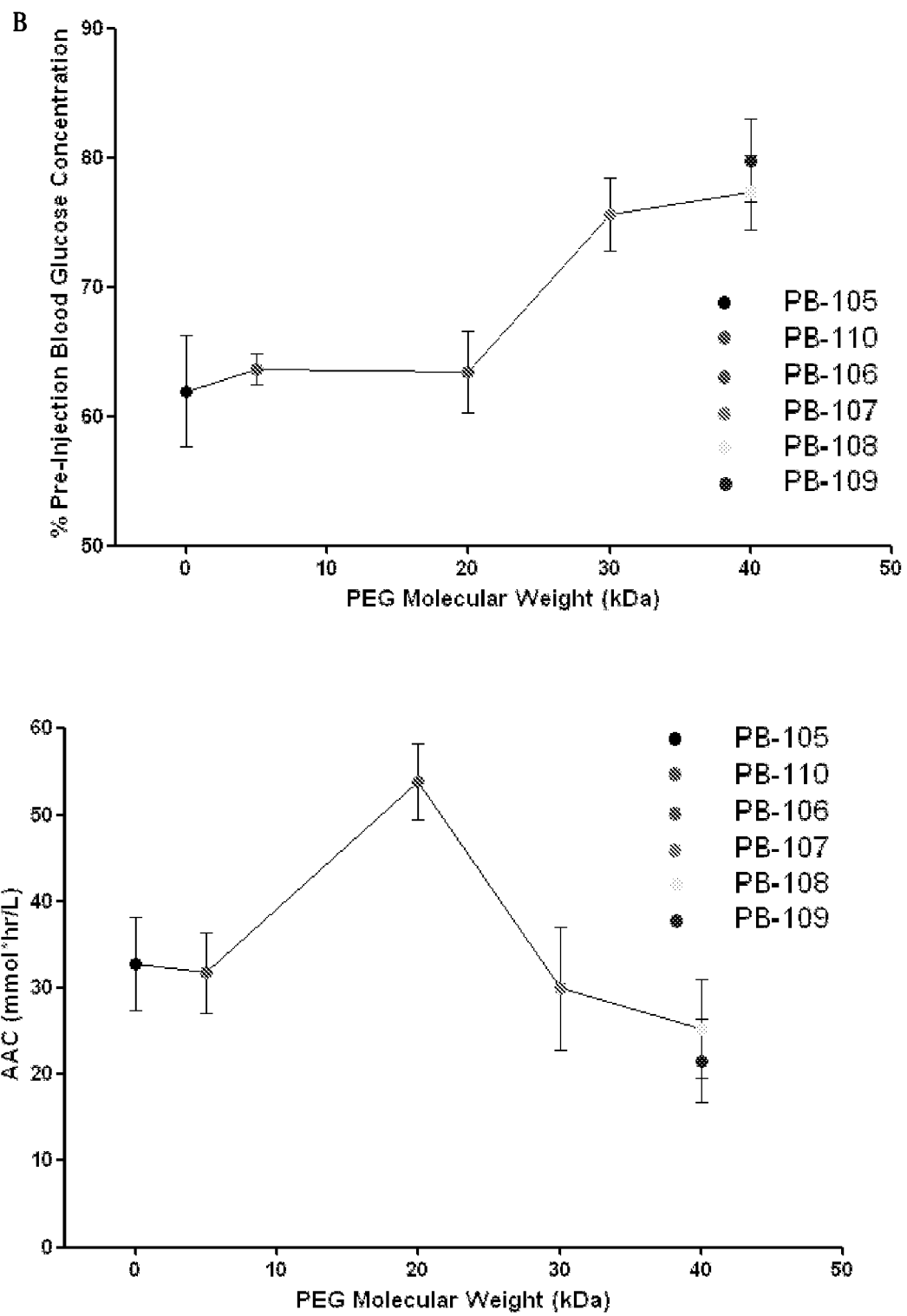

Time-Response Relationship Experiment for Hypoglycemic Effect of Equal Amounts of Pb-105 and PEGylated Conjugates Male Kunming mice (body weight was 22-26 g) were provided. The mice did not fast for food or water prior to the experiment. They were randomly distributed into six groups with twelve mice in each group. Equal volume of PB-105 (10 µg/kg), PB-105 PEGylated (PEG5000) conjugate PB-110 (10 µg/kg), PB-105 PEGylated (PEG20000) conjugate PB-106 (10 µg/kg), PB-105 PEGylated (PEG30000) conjugate PB-107 (10 µg/kg), PB-105 PEGylated (PEG40000) conjugate PB-108 (10 µg/kg) and PB-105 PEGylated (PEG20000×2, double-arm) conjugate PB-109 (10 µg/kg) were subcutaneously injected in bolus. At 0, 1, 2, 4, 8, 12, 18, 24, 36 hr after injection, blood sampling in tail tip was carried out. Blood glucose was determined using OneTouch blood glucose meter and testing strips accompanied (U.S. Johnson & Johnson). The time-response curve for hypoglycemic effect was plotted by using blood glucose value at different time points for y axis and using time points for x axis (FIG. 31), so as to calculate biological half-life and maximum hypoglycemic effect of hypoglycemic effects for PB-105 and PEGylated conjugates thereof, as well as area above curve of hypoglycemic effect (Table 1). It can be seen from Table 1, every conjugate of Exendin variant in this experiment has similar or even significantly higher (PB-106) accumulated hypoglycemic effect (see Area Above Curve), and these conjugates of Exendin variant have significantly longer biological half-life, compared with unconjugated PB-105. The analysis for PEG molecular weight vs. biological half-life, maximum hypoglycemic effect and Area Above Curve of hypoglycemic effect indicates that PB-105 PEGylated conjugates PB-106, PB-107, PB-108 and PB-109 all significantly prolong the period of hypoglycemic effect of PB-105 (half-life $t_{1/2}$). However, when PEG molecular weight being in the range of 5-20 kDa, the prolongation of biological half-life is proportional to molecular weight, and when being larger than 20 kDa, the period of hypoglycemic effect (biological half-life remains the same (FIG. 32A). PEGylated conjugates have the same maximum hypoglycemic effect when PEG molecular weight being in the range of 5-20 kDa, but when being larger than 20 kDa, the maximum hypoglycemic effect decreases with the increase of PEG molecular weight (FIG. 32B). In the term of Area Above Curve of hypoglycemic effect, merely PB-106 (PEG20 kDa) has significantly higher accumulated hypoglycemic effect than PB-105, and other conjugates have similar or a little less effect (FIG. 32C). As known from above, site-specific PEGylation modification (PB-110 and PB-106) does not significantly affect the maximum hypoglycemic effect of conjugates of Exendin variant (respectively, 96% of PB-105), at least when PEG molecular weight being up to 20 kDa. PEGylation modification significantly reduces the maximum hypoglycemic effect when PEG molecular weight being 30 kDa or even more (PB-107, PB-108 and PB-109), although these conjugates still have comparable accumulated hypoglycemic effect and significantly longer biological half-life. This result indicates that conjugated moiety with a higher molecular weight may be useful to conjugate Exendin variants. As such, significantly longer biological half-life and more gentle and stable level of blood glucose are obtained, so as to prevent the level of blood glucose decreasing too low in short period and fluctuating in a wide range. This finding is consistent with the result in in vitro cAMP experiment as described above (see FIG. 26).

TABLE 1

Biological half-life, maximum hypoglycemic effect and Area Above Curve for lowering blood glucose (AAC) for PB-105 and PEGylated conjugates thereof (12 mice in each group)

| Exendin conjugates | $T_{1/2}$ (hrs) | Maximum hypoglycemic effect (% value prior to dosing) | Area Above Curve for blood glucose (AAC, mmol*h/L) |
|---|---|---|---|
| PB-105 | 4.9 ± 0.1 | 38.0 ± 4.3 | 32.8 ± 5.4 |
| PB-110 | 7.0 ± 2.0 | 36.3 ± 1.2 | 31.8 ± 4.6 |
| PB-106 | 13.4 ± 0.5* | 36.5 ± 3.2 | 53.9 ± 4.3* |
| PB-107 | 12.5 ± 2.0* | 24.3 ± 2.8* | 30.0 ± 7.2 |
| PB-108 | 10.8 ± 2.0* | 22.6 ± 2.9* | 25.3 ± 5.7 |
| PB-109 | 9.2 ± 2.2* | 20.2 ± 3.2* | 21.6 ± 4.8 |

*P < 0.05 (vs PB-105)

Example 17

Time-Response Relationship Experiment for Hypoglycemic Effect of Equivalent Amounts of Pb-105 and PEGylated (PEG30000) Conjugate Thereof (PB-107)

Figure 33:
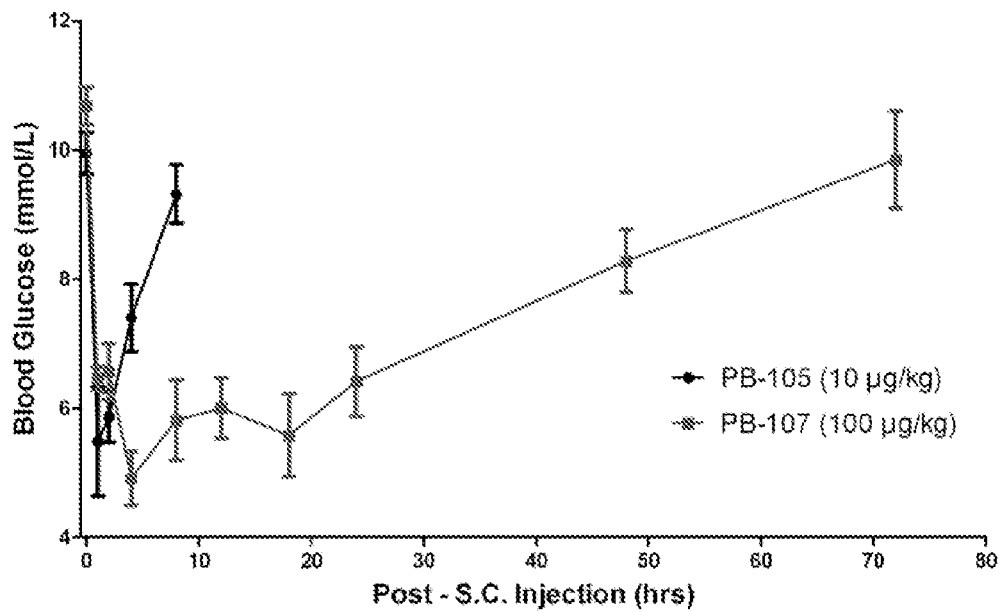
FIG. 33 shows time-response relationship of equivalent blood-glucose-reducing effect of PB-105 and its PEGylated (PEG30000) conjugate PB-107.

Since PEG30000 (PB-107) in vitro reduced the biological activity of PB-105 by about 90% (FIG. 25), and in vivo reduced the biological activity of PB-105 by about 50% (FIG. 31), the dose of PB-107 was increased in order to study the biological half-life of PB-107 under the condition of being equivalent to PB-105. Male Kunming mice (body weight was 22-25 g) were provided. The mice did not fast for food or water prior to the experiment. They were randomly distributed into two groups with six mice in each group. PB-105 (10 μg/kg) and PB-105 PEGylated (PEG30000) conjugate PB-107 (100 μg/kg, this dose produces about 100% hypoglycemic effect of 10 μg/kg PB-105) were subcutaneously injected in bolus. At 0, 1, 2, 4, 8, 12, 18, 24, 36, 48, 72 hr after injection, blood sampling in tail tip was carried out. Blood glucose was determined using OneTouch blood glucose meter and testing strips accompanied (U.S. Johnson & Johnson). The time-response curve for hypoglycemic effect for was plotted by using blood glucose value at different time points for y axis and using time points for x axis, so as to calculate biological half-life PB-105 (10 μg/kg) and PB-107 (100 μg/kg). The results are shown in FIG. 33, the biological half-life of PB-105 (10 μg/kg) and PB-107 (100 μg/kg) are respectively 4.5±0.4 hrs and 44.6±4.5 hrs (P>0.05, PB-107 vs PB-105). The study for time-response relationship of equivalent dose indicates that PEGylation (PEG30000) (PB-107) prolongs the period of hypoglymeric effect of PB-105 by ten-fold.

Example 18

Dose-Response Experiment of Hypoglycemic Effect for PB-105 and PEGylated (PEG20000) Conjugates Thereof (PB-106)

Figure 34:
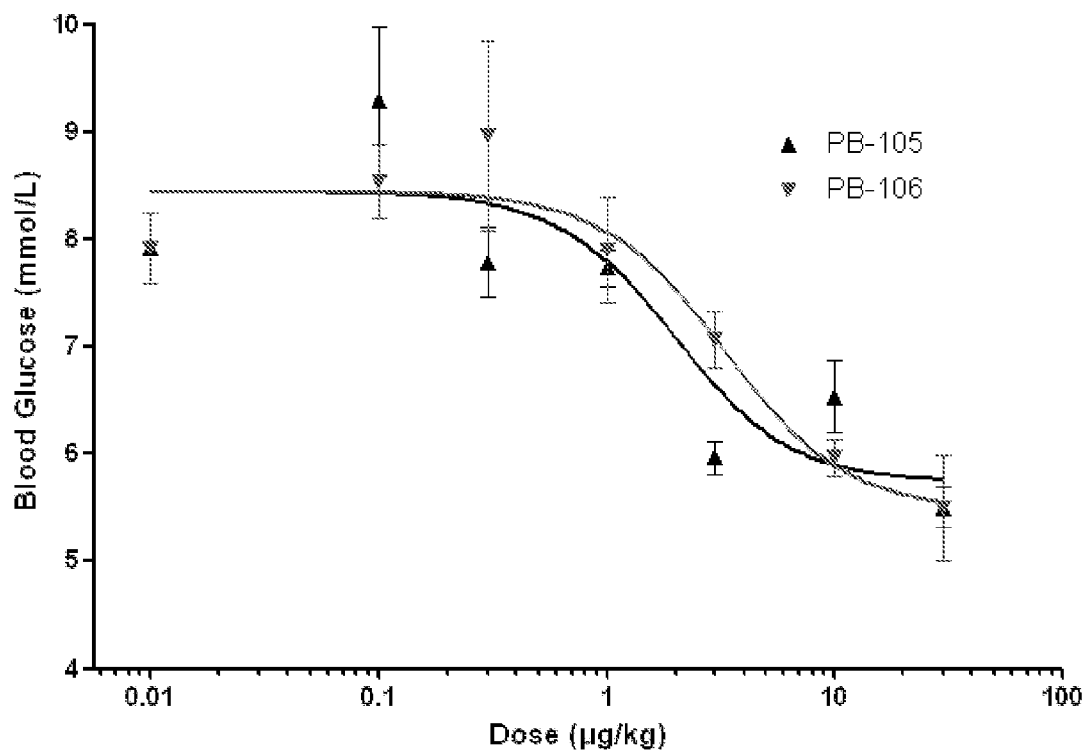
FIG. 34 shows dose-response relationship of blood-glucose-reducing effect of PB-105 and its PEGylated (PEG20000) conjugate PB-106.

Male Kunming mice (body weight was 20-24 g) were provided. The mice fasted for food 3 hrs but not for water prior to the experiment. They were randomly distributed into 13 groups with six mice in each group. Equal volume of saline (10 ml/kg), PB-105 (0.1, 0.3, 1, 3, 10, 30 μg/kg) and equal dose of PEGylated (PEG20000) conjugate PB-106 (0.1, 0.3, 1, 3, 10, 30 μg/kg) were subcutaneously injected in bolus. At 1 hr after injection for PB-105 group (time point for peak of blood glucose reducing, see FIGS. 28 and 31), at 4 hr after injection for PB-106 group (time point for peak of blood glucose reducing, see FIG. 31), blood sampling in tail tip was carried out. Blood glucose was determined using OneTouch blood glucose meter and testing strips accompanied (U.S. Johnson & Johnson). The dose-response curve for hypoglycemic effect was plotted by using blood glucose value for y axis and using dose for x axis (FIG. 34). In turn, dose-response relationship parameter for PB-105 and PB-106 ($E_{min}$, $E_{max}$ and $ED_{50}$) was calculated using Graphpad Prizm software. $E_{min}$ for polus injection of PB-105 and PB-106 were respectively 8.3±0.2 and 8.4±0.3 mmol/L; and $E_{max}$ were respectively 6.0±0.3 and 5.5±0.6 mmol/L (the maximum hypoglycemic efficiency were respectively 27.8% and 34.5%). The $ED_{50}$ of PB-105 and PB-106 were respectively 1.2 and 3.3 μg/kg. The further analysis indicated that Log $ED_{50}$ of PB-105 and PB-106 were respectively 0.07±1.2 and 0.5±0.2(PB-106 vs. PB-105, P>0.05). The experimental result indicated that PEGylated (PEG20000) conjugates of PB-105 (PB-106) had no significantly difference with PB-105 in the term of hypoglycemic effect (including $E_{max}$ and $ED_{50}$).

Example 19

Figure 35:
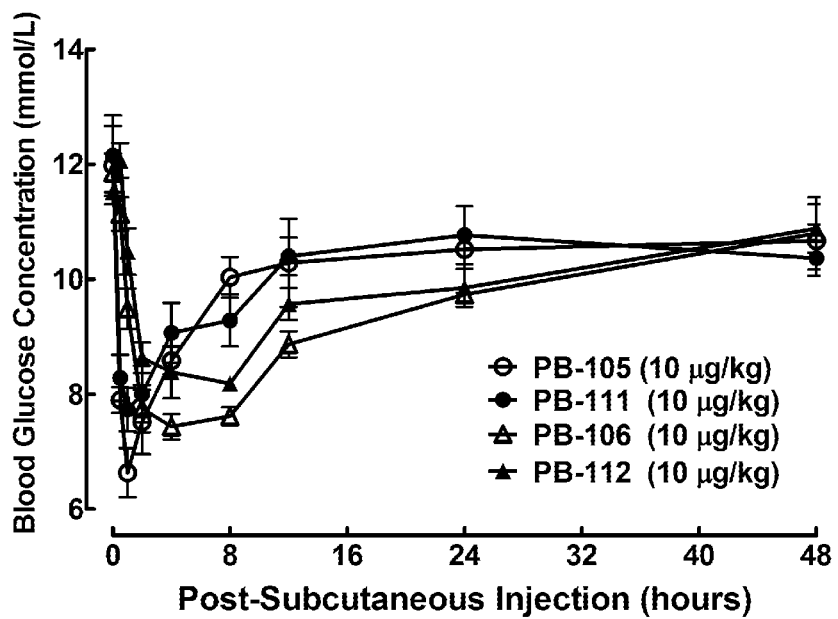
FIG. 35 shows time-response relationship of equivalent blood-glucose-reducing effect of PB-105, PB-111 and PEGylated conjugates thereof. The experimental data is shown as means±SEM.

Time-Response Relationship Experiment for Hypoglycemic Effect of Pb-105, Pb-111 and PEGylated Conjugates (Pb-106 and PB-112) in Normal Mice Male Kunming mice (body weight was 24-30 g) were provided. The mice did not fast for food or water prior to the experiment. They were randomly distributed into four groups with six mice in each group. PB-105 (10 μg/kg), PEGylated (PEG20000) conjugate of PB-105 (PB-106) (10 μg/kg), PB-111 (10 μg/kg) and PEGylated (PEG20000) conjugate of PB-111 (PB-112) (10 μg/kg) were subcutaneously injected in bolus. PB-111 was PB-105 derivative in which cysteine at position 39 of C-terminal linked to tyrosine. At 0, 0.5, 1, 2, 4, 8, 12, 24, 48 hr after injection, blood sampling in tail tip was carried out. Blood glucose was determined using OneTouch blood glucose meter and testing strips accompanied (U.S. Johnson & Johnson). The time-response curve for hypoglycemic effect for was plotted by using blood glucose value at different time points for y axis and using time points for x axis, so as to calculate biological half-life and maximum hypoglycemic effect of PB-105, PB-111 and PEGylated conjugates thereof. The results are shown in FIG. 35, PB-105, PB-106, PB-111 and PB-112 reduced random blood glucose in mice in a manner of time-dependence. The biological half-lifes of PB-105 and PB-111 are respectively 4.6 hrs and 6.0 hrs, and the maximum of hypoglycemic effect are respectively 44.7% and 36.4%. The biological half-lifes of PB-106 and PB-112 are respectively 19.6 hrs and 21.7 hrs, and the maximum of hypoglycemic effect are respectively 37.3% and 34.9%. The results indicated that tyrosine added at position 39 of C-terminal had no effect on the activity of hypoglycemic effect and biological half-life of PB-105 and PEGylated conjugate thereof (PB-106).

Example 20

Time-Response Relationship Experiment for Hypoglycemic Effect of Pb-101 and the Variants Pb-105, Pb-111 and PB-113 as Well as PEGylated Conjugates PB-106, PB-112 and PB-114 in STZ Diabetes Mice The mice were fasted for 14 hrs before diabetes was induced. Blood sample was taken via tail tip bleeding in order to determine the blank value of blood glucose. Then, newly prepared STZ (streptozotocin) (120 mg/10 ml/kg, newly prepared, dissolved in 0.1 M nitrate solution, pH 4.5) was bolus injected subcutaneously. The blood glucose was determined after 3 days. The mice whose random blood glucose being above 16.7 mmol/L were regarded as mice in which diabetes was successfully induced. The mice did not fast for food or water prior to the experiment. They were distributed into 7 groups with 4-6 mice in each group. The blood glucose at 0 hr was determined via tail vein bleeding. And equal volume of PB-101 (10 μg/10 ml/kg), PB-105 (10 μg/kg), PB-106 (10 μg/kg), PB-111 (10 μg/kg), PB-112 (10 μg/kg), PB-113 (10 μg/kg) and PB-114 (10 μg/kg) were subcutaneously injected in bolus. PB-111 was PB-105 derivative in which cysteine at position 39 of C-terminal linked to tyrosine, PB-113 was PB-105 derivative in which glycine at position 2 of N-terminal was substituted by D-alanine, and PB-114 was PEGylated (PEG40000) conjugate of PB-113. At 0, 0.5, 1, 2, 4, 8, 12, 24, 48 hr after injection, blood sampling was carried out and blood glucose was determined. The time-response curve for hypoglycemic effect for PB-101, PB-105, PB-106, PB-111, PB-112, PB-113 and PB-114 was plotted by using blood glucose value at different time points for y axis and using time points for x axis. The curve was plotted using GraphPad Prism 5 Demo software (Prism v5, Graphpad Software, Inc., San Diego, Calif.), and the biological half-life ($t_{1/2}$) of PB-101, PB-105, PB-106, PB-111, PB-112, PB-113 and PB-114 were calculated and compared using mathematical statistics methods.

Figure 36:
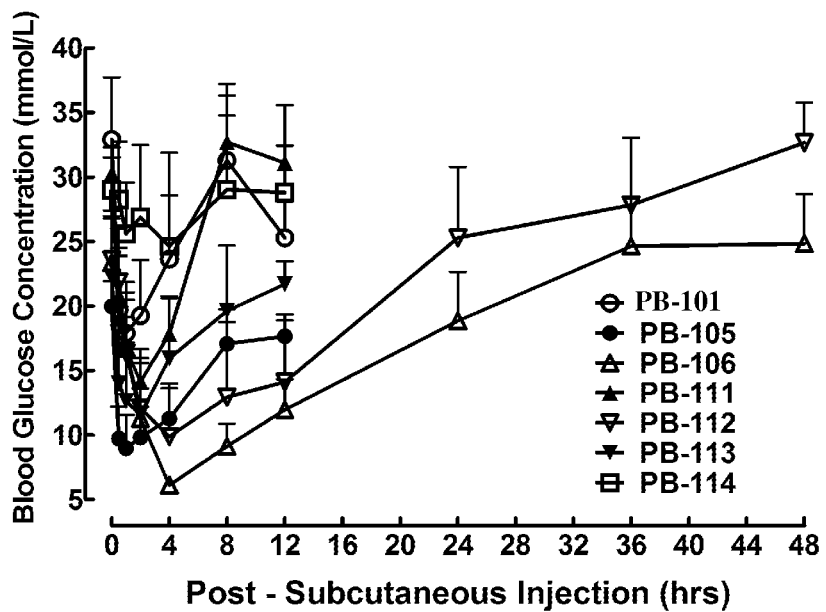
FIG. 36 shows time-response relationship of blood-glucose-reducing effect of PB-101, its variant PB-105, PB-111 and PB-113 as well as the PEGylated conjugate PB-106, PB-112 and PB-114. The experimental data is shown as means±SEM.

As shown in FIG. 36, polus injection of PB-101, PB-105, PB-106, PB-111, PB-112, PB-113 and PB-114 reduced random blood glucose in STZ-induced diabetes mice in a manner of time-dependence. The maximum efficiencies were respectively 47.5%, 57.6%, 69.8%, 54.4%, 59.7%, 49.2% and 17.9% (merely 38% of that for PB-101). The biological half-life of PB-101, PB-105, PB-106, PB-111, PB-112 and PB-113 were respectively 5.5, 5.5, 21.8, 5.0, 20.3 and 5.9 hrs, and the biological half-life of PB-114 cannot be calculated due to hypoglycemic effect. The experimental results indicated that added tyrosine at position 39 of C-terminal or substitution of glycine by D-alanine at position 2 of N-terminal did not reduce the anti-hyperglycemic activity of PB-105, PEGylation (PEG20000) did not reduce the activity of PB-105 and derivatives thereof, but PEGylation (PEG40000) significantly reduce the activity of PB-105 and derivatives thereof.

Example 21

Time-Response Relationship Experiment for Hypoglycemic Effect of Equivalent Amounts of PB-105 and PB-106, PB-119 and PB-120

Figure 37:
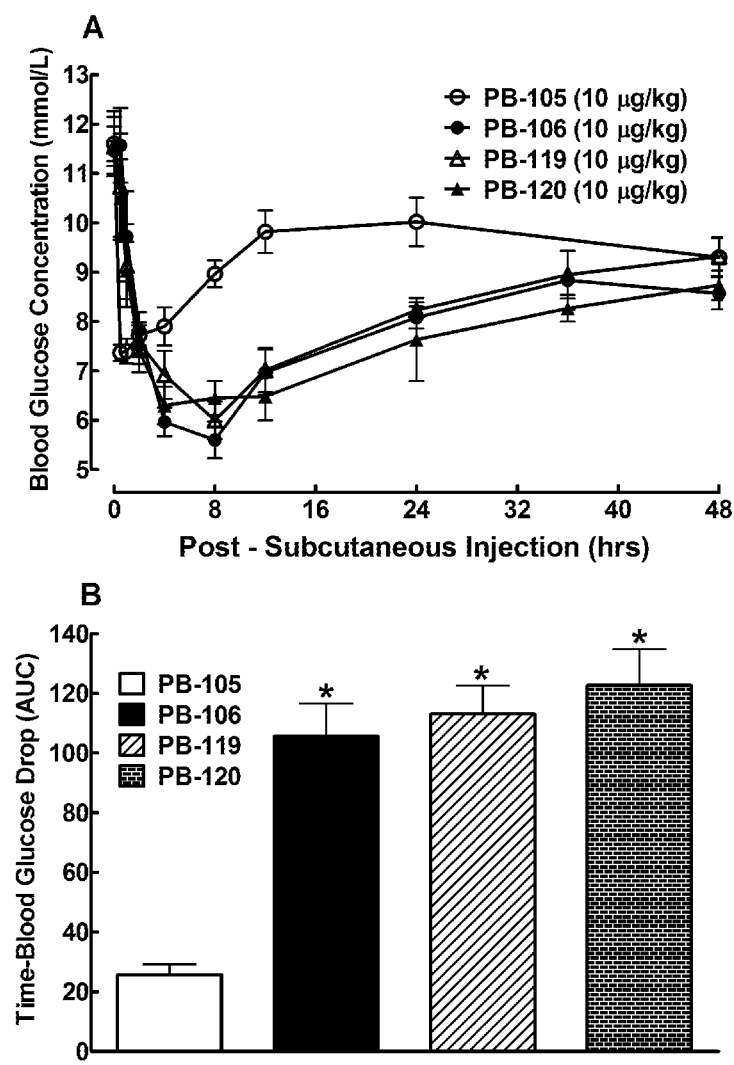
FIG. 37 shows time-response relationship of equivalent blood-glucose-reducing effect of PB-105 and its PEGylated conjugate. The experimental data is shown as means±SEM. * represents significant difference compared with PB-105 group ($p<0.05$).

Male Kunming mice (body weight was 24-30 g) were provided. The mice did not fast for food or water prior to the experiment. They were randomly distributed into four groups with six mice in each group. PB-105 (10 μg/kg), PB-105 PEGylated (PEG20000) conjugate (PB-106) (10 μg/kg), PB-105 PEGylated (PEG23000) conjugate (PB-119) (10 μg/kg) and PB-105 PEGylated (PEG27000) conjugate (PB-120) (10 μg/kg) were subcutaneously injected in bolus. At 0, 0.5, 1, 2, 4, 8, 12, 24, 48 hr after injection, blood sampling in tail tip was carried out. Blood glucose was determined using OneTouch blood glucose meter and testing strips accompanied (U.S. Johnson & Johnson). The time-response curve for hypoglycemic effect was plotted by using blood glucose value at different time points for y axis and using time points for x axis, so as to calculate biological half-life and maximum hypoglycemic effect of PB-105 and PEGylated conjugates thereof. The results are shown in FIG. 37, PB-105, PB-106, PB-119 and PB-120 reduced random blood glucose in mice in a manner of time-dependence. The biological half-life of them were respectively 6.0, 21.7, 24.1 and 26.1 hrs, and the biological half-life increased with the increase of PEG molecular weight. The peak time of hypoglycemic effect were respectively about 1 hr (PB-105) and 4 hr (PB-106, PB-119 and PB-120). The peak values of hypoglycemic effect were respectively 35.0%, 50.9%, 48.2% and 42.2% (FIG. 37A). As calculated as hypoglycemic effect-time area, PB-106, PB-119 and PB-120 all significantly increased the hypoglycemic effect of PB-105 (increase by 3-4 fold). And the accumulated effect increased with the increase of PEG molecular weight (FIG. 37B). The experimental results indicated that PEGylation did not reduce the hypoglycemic activity of PB-105, and significantly prolonged the period of hypoglycemic effect and increased the accumulated hypoglycemic effect when the molecular weight being between 20-27 kDa. As seen from this, when PEG molecular weight being 20-27 kDa, the conjugates of Exendin variants according to the present invention, PB-106, PB-119 and PB-120, provide higher peak value of hypoglycemic effect, compared with unconjugated PB-105. In addition, these conjugates have significantly longer period of hypoglycemic effect and the accumulated hypoglycemic effect increases with the increase of PEG molecular weight, so as to provide a better combined hypoglycemic effect.

Example 22

Pigeon Vomiting Test for PB-101, PB-105, PB-106 and PB-120

Figure 38:
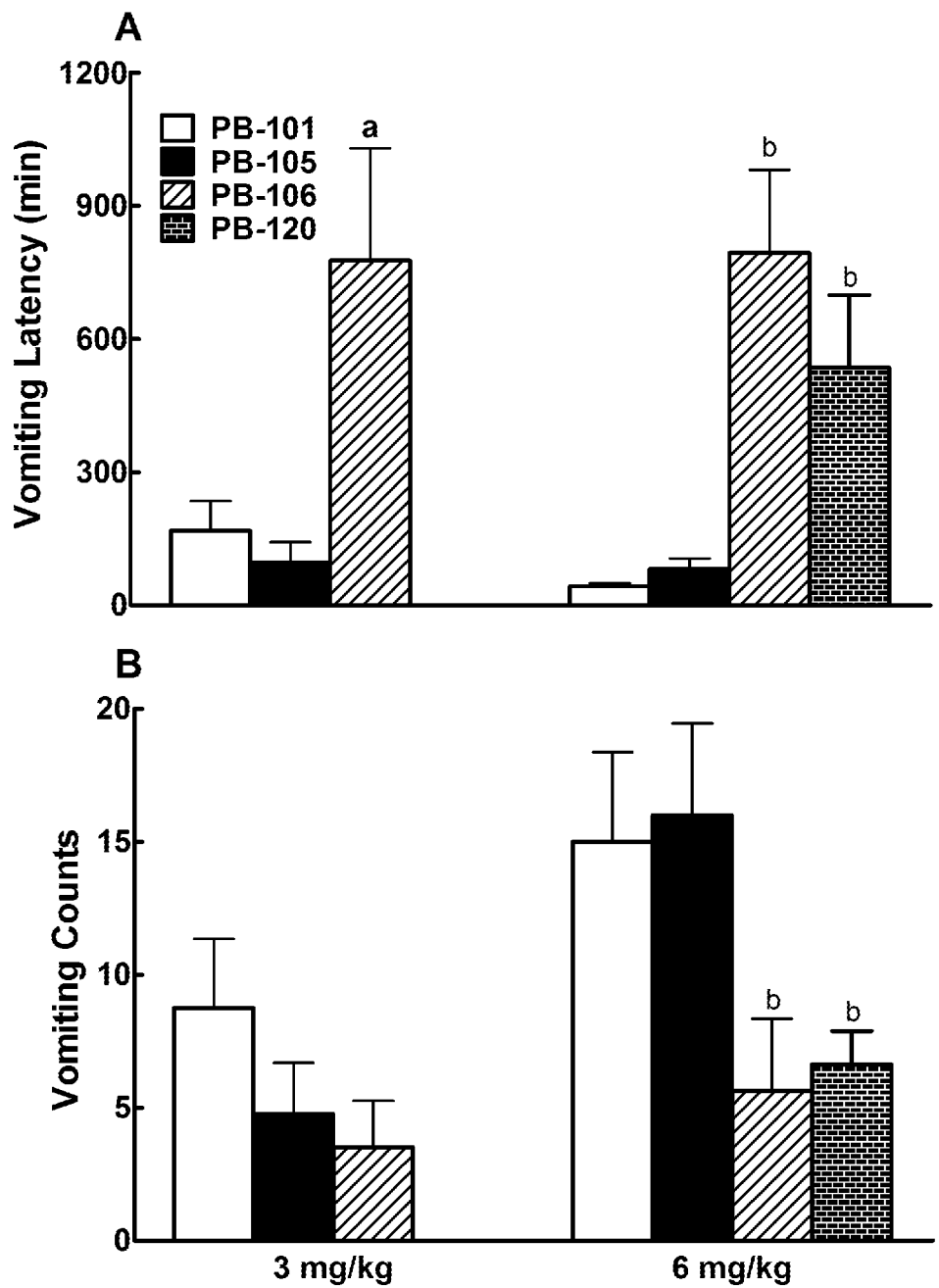
FIG. 38 shows effects of PB-101, PB-105, PB-106 and PB-120 on respective vomiting latency (A) and vomiting times (B) of pigeon. The experimental data is shown as means±SEM. a represents statistically significant difference in the dose of 3 mg/kg compared with PB-105 group ($p<0.05$); b represents statistically significant difference in the dose of 6 mg/kg compared with both PB-101 group and PB-105 group ($p<0.05$).

Healthy pigeons, male or female, were distributed into 7 groups with 4-8 pigeons in each group. PB-101 (3 mg/kg, N=4 or 6 mg/kg, N=8), PB-105 (3 mg/kg, N=4 or 6 mg/kg, N=8), PB-106 (3 mg/kg, N=4 or 6 mg/kg, N=8) and PB-120 (6 mg/kg, N=8) were separately bolus injected subcutaneously. The times of vomiting and latency for vomiting (the period from dosing to the first vomiting) were observed and recorded in 24 hrs after dosing using electronic monitor system. The times of vomiting was defined as once if neck stretching, mouth opening, shrugging, abdominal contracting, and finally calming down or the end of vomiting. The previous experiences indicated that vomiting response was not induced by normal situation such as no dosing in pigeons, and dosing of PB-101 (3 and 6 mg/kg) and PB-105 (3 and 6 mg/kg) induced significant vomiting in a manner of dose-dependence. In PB-106 (3 mg/kg and 6 mg/kg) and PB-120 (6 mg/kg) groups, the latency of vomiting was significantly prolonged (prolonged by about 5-18 fold, see FIG. 38A), and the times of vomiting were significantly reduced (reduced by about 50-70%, see FIG. 38B), compared with groups of corresponding dose of PB-101, PB-105. For the dose of 6 mg/kg, the difference was statistically significant (p<0.05). The results indicated that PEGylation significantly reduced the vomiting response to Exendin and the variants thereof.

Example 23

Systematically Allergic Reaction and Effects on Body Weight Induced by PB-101, PB-105 and PB-106 in Guinea Pigs 44 male healthy guinea pigs were provided, and the body weight of each guinea pig was about 300 g. They were distributed into 5 groups, i.e. saline (N=10), PB-101(N=10), PB-105 (N=10), PB-106 (N=10) and albumin group (N=4). Saline (1 ml/kg), PB-101 (100 μg/kg), PB-105 (100 μg/kg), PB-106 (100 μg/kg) and chicken ovalbumin (80 mg/kg) were respectively injected subcutaneously every other day for three consecutive times. At 14 day after the last injection, stimulating amount of saline (1 ml/kg), PB-101 (300 μg/kg), PB-105 (300 μg/kg), PB-106 (300 μg/kg) and albumin (240 mg/kg) were respectively injected via toe vein. Immediately after injection, the response of animals was observed for 0-3 hrs after stimulation. The symptoms for allergic reaction in animals were recorded as shown in Table 2, and assessed as shown in Table 3 (semi-quantitative).

TABLE 2

The symptoms for allergic reaction in aminals

0 Normal
1 Restless
2 hair shaft
3 trembling
4 scratch nose
5 sneezes
6 cough
7 shortness of breath TABLE 2-continued The symptoms for allergic reaction in aminals 8 urination
9 defecation
10 tears
11 breathing difficulty
12 wheezing
13 purpura
14 gait
15 jump
16 respite
17 cramps
18 rotation
19 tidal breathing
20 dead

TABLE 3

Evaluation of degrees of systematically allergic reaction in animals and semi-quantitative standard

| 0 | – | 0 | Negative allergic reaction |
| 1-4 symptoms | + | 1 | Weak negative allergic reaction |
| 5-10 symptoms | ++ | 2 | Positive allergic reaction |
| 11-19 symptoms | +++ | 3 | Strong positive allergic reaction |
| 20 | ++++ | 4 | Very strong positive allergic reaction |

Figure 39:
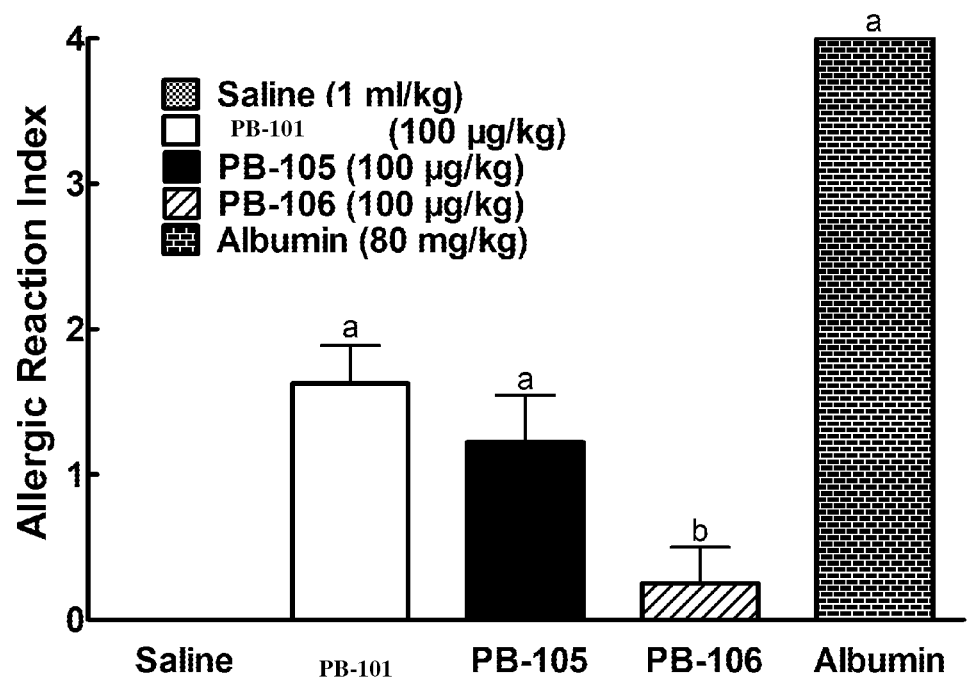
FIG. 39 shows effects of PB-101, PB-105, and PB-106 on allergic response in systematically immunized guinea pig. The experimental data is shown as means±SEM. a represents statistically significant difference compared with saline group ($p<0.05$); b represents statistically significant difference compared with PB-101 group or PB-105 group ($p<0.05$).

The curve was plotted using time points for x axis and degrees of allergic response (semi-quantitative) for y axis, as shown in FIG. 39. Any allergic reaction was not found in guinea pigs of saline control group, and that is, negative allergic reaction. The guinea pigs in albumin group died immediately after stimulation (<2 min), and that is, very strong positive allergic reaction. Guinea pigs in PB-101 and PB-105 groups had allergic response, and that is positive allergic reaction. PB-101 and PB-105 were polypeptides having 39 amino acid residues, and can induce antibody production in vivo after chronic dosing (Buse et al. Effects of exenatide (exendin-4) on glycemic control over 30 weeks in sulfonylurea-treated patients with type 2 diabetes. *Diabetes Care.* 2004; 27: 2628-2635). And, PB-105 PEGylated (PEG20000) conjugate PB-106 leaded to weak negative allergic reaction in guinea pigs. This result indicated that PEGylation (PB-106) was able to significantly reduce the immunogenity of PB-101 or PB-105 and allergic reaction.

Figure 40:
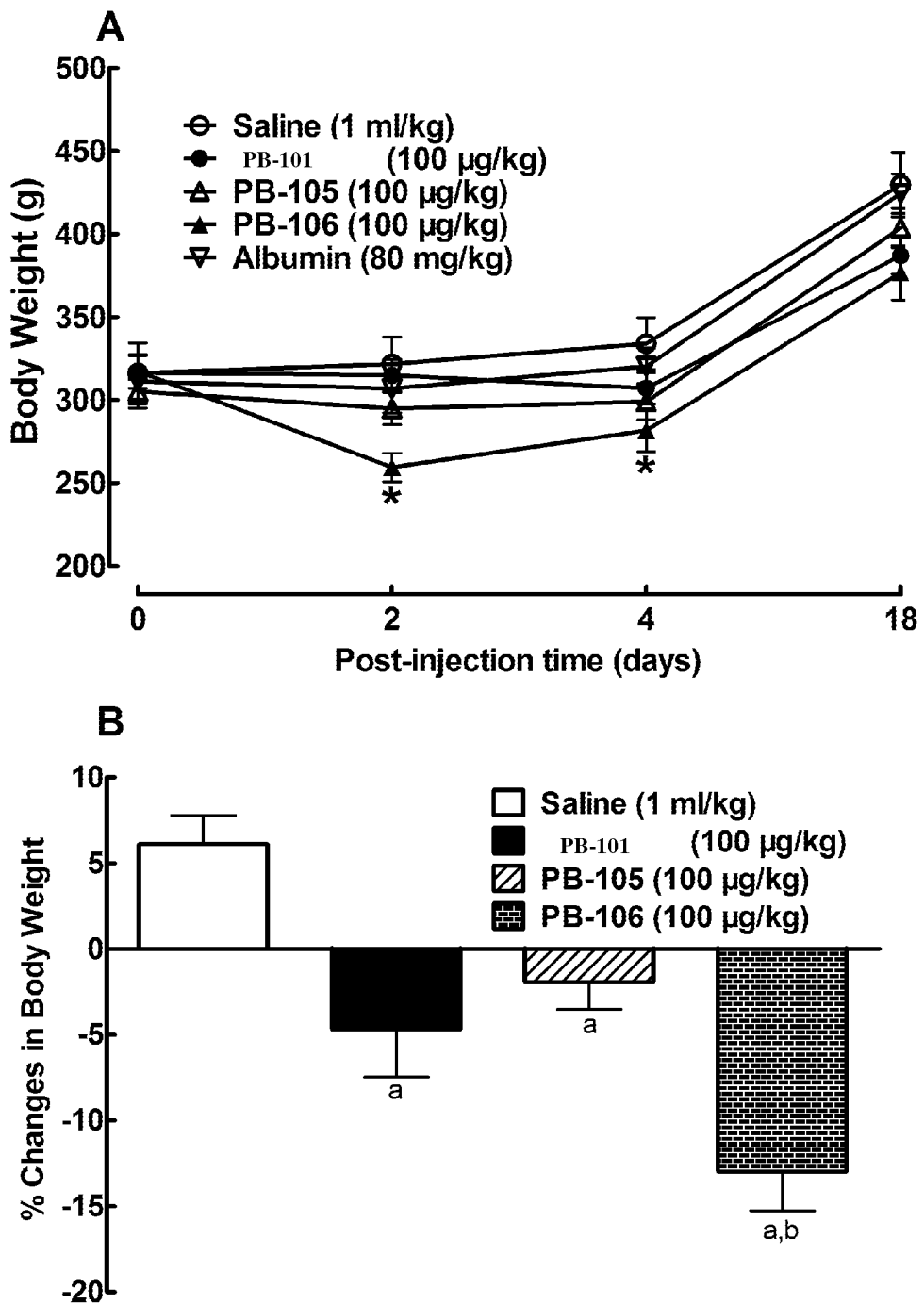
FIG. 40 shows effects on body weight increase in guinea pig (A) 0-18 days and (B) 0-4 days after dosage of PB-101, PB-105 and PB-106. The experimental data is shown as means±SEM. a represents statistically significant difference compared with saline group ($p<0.05$); b represents statistically significant difference compared with Exenatide or PB-105 group ($p<0.05$).

The curve plotted using time points for x axis and body weight of guinea pigs for y axis (FIG. 40) showed that the body weight of guinea pigs in saline group during sensitization continuously increased (the body weight increased by about 38% during 18 days of experiment). The body weight did not decrease 4 days after two successive dosing of albumin, compared with saline group. However, The body weight of guinea pigs respectively decreased by about 8% and 11% (p<0.05) 4 days after two successive dosing of PB-101 (100 μg/kg) or PB-105 (100 μg/kg). The body weight of guinea pigs decreased more after dosing of equivalent amount of PB-106, compared with PB-101 or PB-105. And dosing of PB-106 leaded to respectively about 8% and 11% of further reduction (p<0.05), compared with dosing of PB-101 and PB-105. The body weight of guinea pigs in PB-101, PB-105 and PB-106 groups recovered 12 days after ceasing dosing, which was comparable with that in saline group.

Example 24

Effect of PB-105, PB-106, PB-119 and PB-120 on Body Weight of Rat and Amount of Food Intake 24 male healthy SD rats were provided, and the body weight thereof was about 200 g. The rats were distributed into 5 groups: saline group (1 ml/kg, N=4), PB-105(100 µg/kg, N=5), PB-106 (100 µg/kg, N=5), PB-119 (100 µg/kg, N=5) and PB-120 (100 µg/kg, N=5). Saline and drugs were respectively injected subcutaneously in each other day for three successive times. The body weight and food intake change in rats were observed every day.

Figure 41:
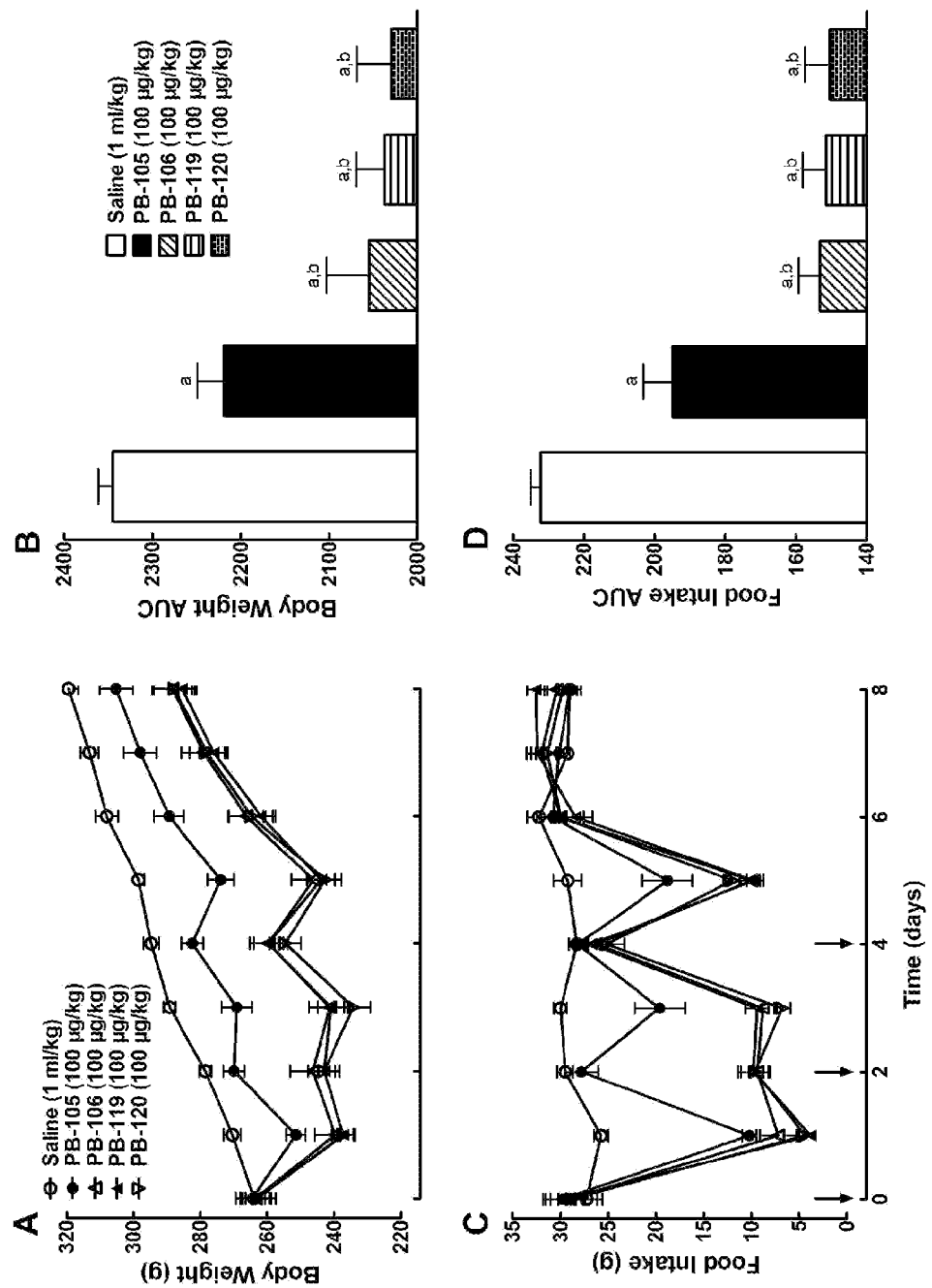
FIG. 41 shows effects on (A) body weight and on (C) food intake in rat after dosage of PB-105, PB-106, PB-119 and PB-120. B and D shows Area Under Curve for body weight-time curve and food intake-time curve of respective groups after dosing. The experimental data is shown as means±SEM. a represents statistically significant difference compared with saline group ($p<0.05$); b represents statistically significant difference compared with PB-105 group ($p<0.05$).
Figure 42:
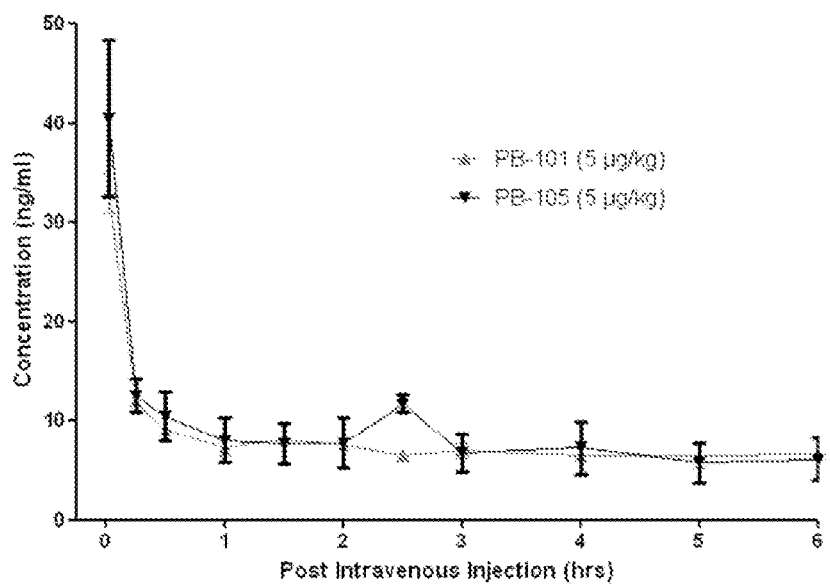
FIG. 42 shows concentration-time curve of bolus injection of Exenatide and PB-105.

The curve plotted using time points for x axis and body weight of rats for y axis (FIG. 41A) showed that the body weight of rats in saline group continuously increased during dosing (the body weight increased by 33.4% during 9 days of experiment). The body weight (by body weight-time AUC as an indicator) decreased by about 5.3% ($p<0.05$) 9 days after three successive dosing of PB-105 (100 µg/kg), compared with saline group. Dosing of equivalent amount of PB-106, PB-119 and PB-120 leaded to more body weight reduction than PB-105. The body weight (by body weight-time AUC as an indicator) respectively decreased by about 7%, 8% and 8% ($p<0.05$) in the case of dosing of PB-106, PB-119 and PB-120, compared with dosing of PB-105.

The curve plotted using time points for x axis and food intake amount of rats for y axis (FIG. 41B) showed that the food intake amount of rats in saline group substantially remained during dosing. The food intake amount (by food intake amount-time AUC as an indicator) decreased by about 16% after three successive dosing of PB-105 (100 µg/kg), compared with saline group. Dosing of equivalent amount of PB-106, PB-119 and PB-120 leaded to more reduction of food intake than PB-105. The further reduction of 18%, 19% and 19% ($p<0.05$) were obtained in the case of dosing PB-106, PB-119 and PB-120, compared with dosing of PB-105.

It is well known that Exenatide may reduce the body weight in obesity patients and induce nausea and vomiting response, in which the mechanism of its action is associated with inhibition of feeding center in center nervous system and activation of vomiting center (Larsen. Mechanisms behind GLP-1 induced weight loss, Br J Diabetes Vasc Dis 2008; 8 (Suppl 2): S34-S41; Schick et al. Glucagonlike peptide 1 (7-36)-amide acts at lateral and medial hypothalamic sites to suppress feeding in rats. Am J Physiol Regul Integr Comp Physiol 2003; 284:R1427-35). However, the conjugates of Exendin or variants thereof are difficult to pass through blood-brain barrier due to enlarged molecular weight, and thus may reduce the vomiting response induced by PB-101 (see Example 22). Accordingly, before the beginning of this study, the applicant expected that Exendin or the variants thereof would reduce the effect of Exendin in reducing food intake and body weight which was mediated by central neuro system. However, the applicant surprisingly found that the PEG conjugates of Exendin or the variant thereof had the significantly enhanced effect of reducing body weight and food intake, although wild-type Exendin and unconjugated Exendin variant both reduce body weight and food intake.

Example 25

Pharmacokinetics Experiments of PB-101 and PB-105

Male SD rats (body weight: 250-300 g, purchased from Shanghai Lab Animal Center, Chinese Science Academy) were anaesthetized by applying 30% chloral hydrate (300 mg/kg, i.p.). Femoral artery and vein catheterization was carried out by incising at upper right edge of large groin and dissecting femoral artery and vein (polyethylene PESO tube, U.S. Becton Dickinson Corporation). Right artery catheter was used for blood sampling, and right vein catheter was used for dosing. PE-50 tube was led from the neck back through dorsal subcutaneous. The catheter was filled with heparin solution (200 U/ml), and the incision was sutured. After operation, the rats were separately contained in separate cages, and recovered for more than 12 hrs. The rats with catheters were free for movements and diets in cages. The rats were distributed into PB-101 group and PB-105 group (3-6 rats in each group). 5 µg/kg of the agent was applied by polus injection in right femoral vein. Blood samples were respectively taken at 0.08, 0.25, 0.5, 1, 1.5, 2, 2.5, 3, 4, 5, 6 hrs after dosing. The blood samples were placed in Eppendorf tube and centrifuged for plasma preparation (5000 rpm, 5 min), and stored at −20° C. until use. The concentration of drugs in samples was determined by Exenatide EIA Kit (Phoenix Pharmaceuticals, Inc. USA) after complete preparation of every group of plasma samples. Drug-time curves of PB-101 and PB-105 were plotted using plasma concentration for y axis and time for x axis. The results showed that PB-105 and PB-101 had similar distribution and clearance in rats.

Parameter statistical analysis of non-compartmental method was carried out employing Kinetica 5.0 (Thermo Fisher Scientific Inc., USA) software, so as to calculate pharmacokinetical parameters of PB-101 and PB-105 ($C_{max}$, $AUC_{0-t}$, $AUC_{0\infty}$, $t_{1/2}$, MRT, CL and $V_{ss}$, etc.). The results were shown in Table 4. The plasma half-life of PB-101 and PB-105 was respectively 4.8±0.7 and 4.9±1.4 hrs (PB-105 vs. PB-101, $P>0.05$). And area under curve of drug-time curves was respectively 45.4±1.6 and 47.9±19.0 ng*hr/ml (PB-105 vs. PB-101, $P>0.05$). The experimental results showed that PB-105 and PB-101 had similar pharmacokinetical properties.

TABLE 4

| Pharmacokinetic parameters of PB-101 and PB-105 (3-6 rats in each group) | | | | |
| --- | --- | --- | --- | --- |
| | N | $C_{max}$ (ng/ml) | $AUC_{0-t}$ (ng*h/ml) | $AUC_{0-\infty}$ (ng*h/ml) |
| PB-101 | 3 | 33.0 ± 2.0 | 45.4 ± 1.6 | 85.2 ± 4.4 |
| PB-105 | 6 | 36.8 ± 10.6 | 47.9 ± 19.0 | 103.8 ± 51.1 |

| | $T_{1/2}$ (h) | MRT (h) | CL (ml/(h*kg)) | $V_{ss}$ (ml/kg) |
| --- | --- | --- | --- | --- |
| PB-101 | 4.8 ± 0.7 | 6.9 ± 0.7 | 59.0 ± 3.1 | 403.2 ± 21.3 |
| PB-105 | 4.9 ± 1.4 | 7.2 ± 2.2 | 117.7 ± 58.5 | 563.8 ± 186.1 |

Example 26

Pharmacokinetics Experiments of Pb-105 and PEGylated Conjugate Thereof

Figure 43:
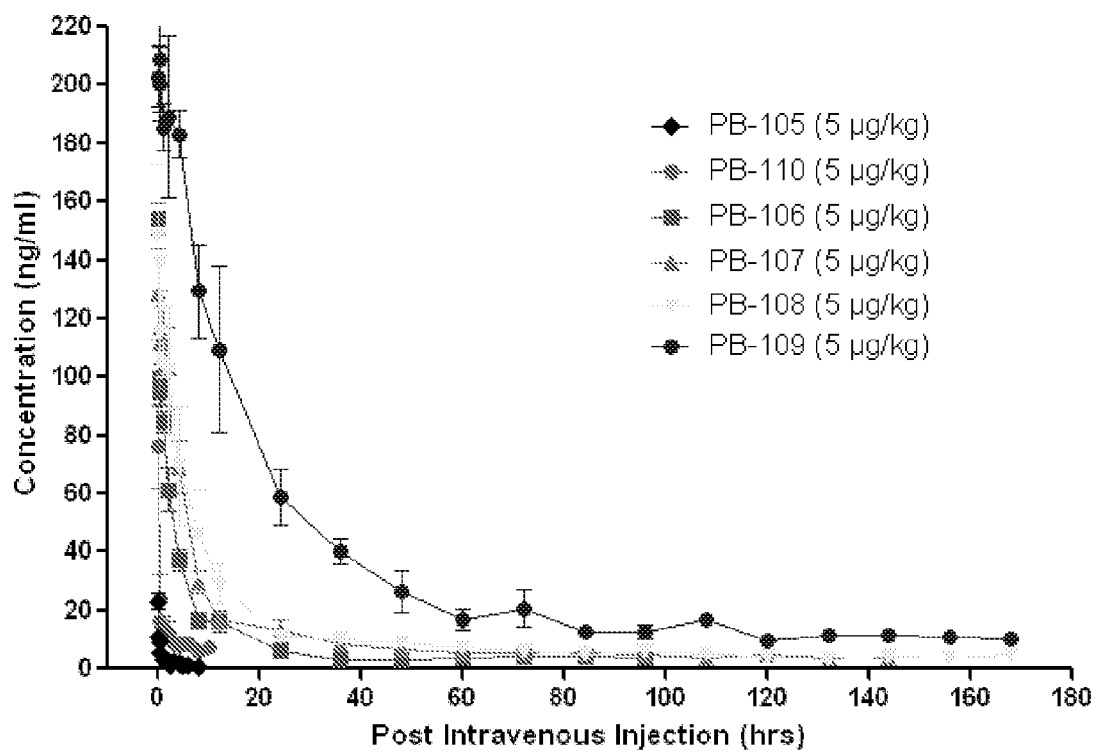
FIG. 43 shows concentration-time curve of bolus injection of PB-105 and its PEGylated Exendin conjugate.

Male SD rats (body weight: 250-300 g, purchased from Shanghai Lab Animal Center, Chinese Science Academy) were anaesthetized by applying 30% chloral hydrate (300 mg/kg, i.p.). Femoral artery and vein catheterization was carried out by incising at upper right edge of large groin and dissecting femoral artery and vein (polyethylene PESO tube, U.S. Becton Dickinson Corporation). Right artery catheter was used for blood sampling, and right vein catheter was used for dosing. PE-50 tube was led from the neck back through dorsal subcutaneous. The catheter was filled with heparin solution (200 U/ml), and the incision was sutured. After operation, the rats were separately contained in separate cages, and recovered for more than 12 hrs. The rats with catheters were free for movements and diets in cages. The rats were distributed into 6 groups (3 rats in each group): PB-105, PB-110, PB-106, PB-107, PB-108 and PB-109. 5 μg/kg of the agent was applied by polus injection in right femoral vein, and 0.2 ml blood was sampled at different time points. For the first 48 hrs after dosing, blood sampling was carried out using PESO tube, and after 48 hrs, blood sampling was carried out by tail vein bleeding. Specifically, PB-105 group 0.08, 0.25, 0.5, 1, 1.5, 2, 2.5, 3, 4, 5, 6 hrs after dosing), PB-110 group (0.08, 0.25, 0.5, 1, 2, 3, 4, 5, 6, 8, 10 hrs after dosing), PB-106 group (0.08, 0.25, 0.5, 1, 2, 4, 8, 12, 24, 36, 48, 60, 72, 84, 96 hrs after dosing), PB-107 group (0.08, 0.25, 0.5, 1, 2, 4, 8, 12, 24, 36, 48, 60, 72, 84, 96, 108, 120, 132, 144 hrs after dosing), PB-108 and PB-109 group (0.08, 0.25, 0.5, 1, 2, 4, 8, 12, 24, 36, 48, 60, 72, 84, 96, 108, 120, 132, 144, 156, 168 hrs after dosing). The blood samples were placed in Eppendorf tube and centrifuged for plasma preparation (5000 rpm, 5 min), and stored at −20° C. until use. The concentration of drugs in samples was determined by Exenatide EIA Kit (Phoenix Pharmaceuticals, Inc. USA) after complete preparation of every group of plasma samples. Drug-time curves of PEGylated conjugates were plotted using plasma concentration for y axis and time for x axis. The results showed that PB-105 and PEGylated conjugates exhibited rapid distribution and slow clearance (see FIG. 43).

Figure 44:
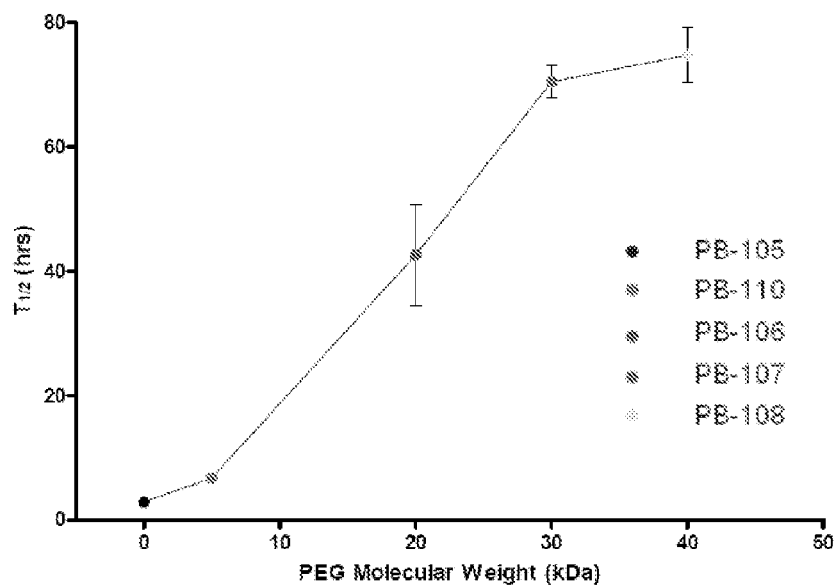
FIG. 44A shows relationship between MW of PEG in PEGylated Exendin variant conjugate and plasma half-life.
FIG. 44B shows relationship between MW of PEG in PEGylated Exendin variant conjugate and Area Under Curve (AUC) of concentration-time curve.
Figure 44:
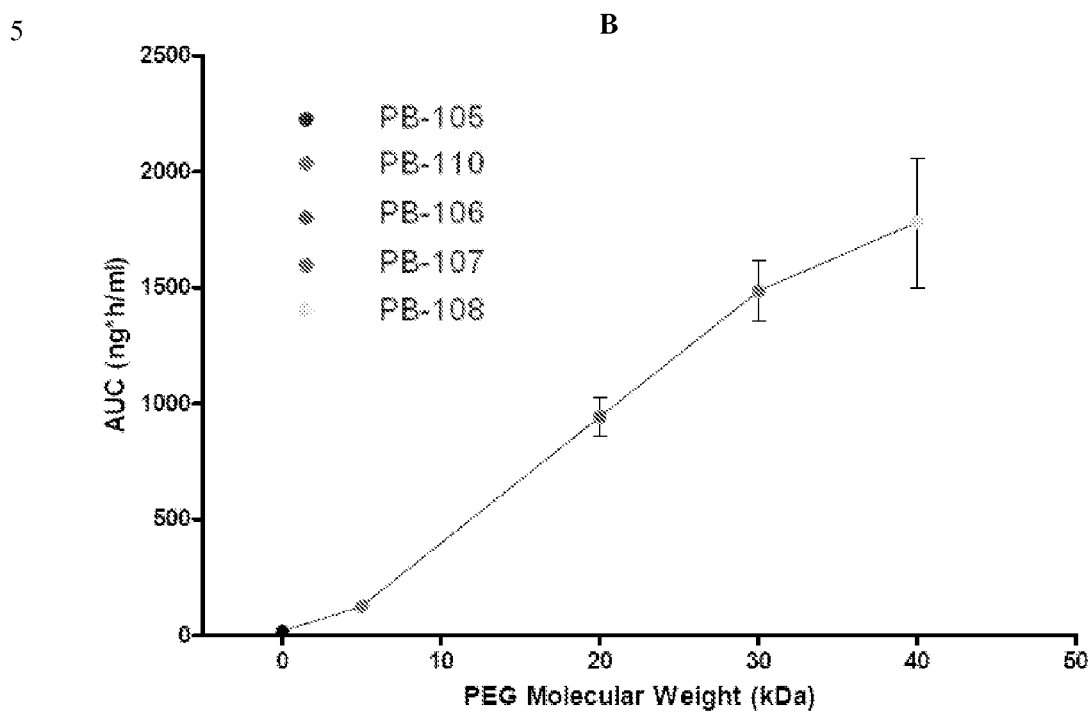

Parameter statistical analysis of non-compartmental method was carried out employing Kinetica 5.0 (Thermo Fisher Scientific Inc., USA) software, so as to calculate pharmacokinetical parameters of PB-105 and PEGylated conjugates thereof ($C_m$, $AUC_{0-t}$, $AUC_{0-\infty}$, $t_{1/2}$, MRT, CL and $V_{ss}$, etc.). The results were shown in Table 5. The plasma half-life of PB-105 was 2.9±0.1 hrs, and the plasma half-life of the PEGylated conjugate was increased with the increase of PEG molecular weight. Area under curve of drug-time curve of PB-105 was 18.2±1.9 ng*hr/ml, and area under curve of drug-time curve of PEGylated conjugate was increased with the increase of PEG molecular weight. FIGS. 44A and 44B respectively showed that the relationship between PEG molecular weight in PEGylated conjugates and plasma half-life, area under curve of drug-time curve.

TABLE 5

Pharmacokinetic parameters of PB-105 and PEGylated conjugates thereof (3 rats in each group)

| | $C_{max}$ (ng/ml) | $AUC_{0-t}$ (ng*hr/ml) | $AUC_{0-\infty}$ (ng*hr/ml) |
|---|---|---|---|
| PB-105 | 23.0 ± 2.8 | 18.2 ± 1.9 | 24.5 ± 2.2 |
| PB-110 | 76.1 ± 14.5 | 101.0 ± 25.8 | 165.5 ± 45.3 |
| PB-106 | 149.2 ± 5.7 | 942.5 ± 84.6 | 1146.0 ± 65.2 |
| PB-107 | 128.2 ± 15.5 | 1485.2 ± 123.0 | 1879.3 ± 82.1 |
| PB-108 | 148.1 ± 24.5 | 1780.7 ± 279.9 | 2202.5 ± 318.8 |
| PB-109 | 240.1 ± 20.9 | 5478.8 ± 654.3 | 7033.4 ± 861.6 |

| | $T_{1/2}$ (hr) | MRT (hr) | CL (ml/hr*kg) | $V_{ss}$ (ml/kg) |
|---|---|---|---|---|
| PB-105 | 2.9 ± 0.1 | 4.1 ± 0.2 | 207.8 ± 20.9 | 846.3 ± 79.0 |
| PB-110 | 6.1 ± 0.8 | 9.6 ± 1.0 | 37.5 ± 13.5 | 340.1 ± 92.9 |
| PB-106 | 42.6 ± 8.1 | 47.3 ± 11.6 | 4.4 ± 0.3 | 209.0 ± 57.3 |
| PB-107 | 70.5 ± 2.6 | 75.3 ± 9.5 | 2.7 ± 0.1 | 201.6 ± 27.3 |
| PB-108 | 74.8 ± 4.5 | 90.2 ± 10.2 | 2.3 ± 0.3 | 193.6 ± 50.0 |
| PB-109 | 103.6 ± 2.4 | 102.0 ± 6.8 | 0.7 ± 0.1 | 74.8 ± 10.4 |

The Exendin variants according to the present invention have improved pharmacokinetical properties, significantly reduce blood glucose, and have comparable or better biological activities. The conjugates of Exendin variants which are site-specifically coupled to polymers through thiol in cysteines significantly prolong the half-life of Exendin variants and remain high biological activity.

The present invention has been illustrated by specific examples. However, the skilled person can understand that the present invention is not limited to the specific examples, and the skilled person may make some variation or modification in the scope of the present invention without deviating out of the spirit and scope of the present invention. These variation and modification are in the scope of the present invention.

The invention claimed is:

1. An Exendin variant conjugate having the activity of GLP-1 receptor agonist, wherein one or more polymer moieties are conjugated to cysteine residue of the Exendin variant, wherein the one or more polymer moieties have a molecular weight of from 21 kDa to 29 kDa, and wherein the one or more polymer moieties are each independently polyethylene glycol.

2. The conjugate according to claim 1, wherein the Exendin variant comprises an amino acid sequence in which one or more amino acid residues are substituted by cysteine, in comparison with wild-type Exendin sequence.

3. The conjugate according to claim 2, wherein the wild-type Exendin sequence is selected from the group consisting of: Exendin-4 (SEQ ID NO: 1) and Exendin-3 (SEQ ID NO: 2).

4. The conjugate according to claim 1, wherein the Exendin variant comprises a cysteine substitution at C-terminal of the Exendin variant.

5. The conjugate according to claim 4, wherein the Exendin variant has a cysteine substitution at the position corresponding to Ser at position 39 of SEQ ID NO:1 or SEQ ID NO: 2.

6. The conjugate according to claim 1, wherein the Exendin variant comprises a sequence selected from the group consisting of SEQ ID NOs: 4-8.

7. A method of preparing the conjugate according to claim 1, comprising contacting an Exendin variant with a polymer.

8. A pharmaceutical composition, comprising an effective amount of the conjugate according to claim 1, and optionally a pharmaceutically acceptable carrier.

9. A method of reducing blood glucose, comprising administrating to a subject in need thereof the conjugate according to claim 1.

10. The method according to claim 9, which is useful in treating diabetes.

11. The method according to claim 10, which is useful in treating Type 1 diabetes or Type 2 diabetes.

12. The method according to claim 10, which is useful in treating Type 2 diabetes.

13. A kit comprising the conjugate according to claim 1 and instructions for using the kit.

14. A method of reducing body weight, comprising administrating to a subject in need thereof the Exendin variant conjugate according to claim 1, in which the one or more polymer moieties are preferably polyethylene glycol moieties.

15. The conjugate according to claim 1, wherein the one or more polymer moieties have a molecular weight of from 23 kDa to 27 kDa.

* * * * *

SEQUENCE LISTING

<160> NUMBER OF SEQ ID NOS: 8

<210> SEQ ID NO 1
<211> LENGTH: 39
<212> TYPE: PRT
<213> ORGANISM: unknown
<220> FEATURE:
<223> OTHER INFORMATION: Exendin-4 peptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: unknown
<220> FEATURE:
<223> OTHER INFORMATION: Exendin-3 peptide -continued

```
<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
        35

<210> SEQ ID NO 3
<211> LENGTH: 39
<212> TYPE: PRT
<213> ORGANISM: artificial sequence
<220> FEATURE:
<223> OTHER INFORMATION: derivative from Exendin-4

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Cys Pro Pro Ser
        35

<210> SEQ ID NO 4
<211> LENGTH: 39
<212> TYPE: PRT
<213> ORGANISM: artificial sequence
<220> FEATURE:
<223> OTHER INFORMATION: derivative from Exendin-4

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Cys
        35

<210> SEQ ID NO 5
<211> LENGTH: 39
<212> TYPE: PRT
<213> ORGANISM: artificial sequence
<220> FEATURE:
<223> OTHER INFORMATION: derivative from Exendin-4

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Cys Pro Ser
                20                  25                  30

Ser Gly Ala Pro Pro Ser
        35

<210> SEQ ID NO 6
<211> LENGTH: 39
<212> TYPE: PRT
<213> ORGANISM: artificial sequence
<220> FEATURE:
<223> OTHER INFORMATION: derivative from Exendin-4

<400> SEQUENCE: 6

His Gly Glu Gly Thr Phe Thr Ser Asp Leu Ser Lys Gln Met Glu Glu
```

```
                                  1               5                  10                  15
                    Glu Ala Val Arg Leu Phe Ile Glu Cys Leu Lys Asn Gly Gly Pro Ser
                                        20                  25                  30

Ser Gly Ala Pro Pro Ser
                                35

<210> SEQ ID NO 7
<211> LENGTH: 40
<212> TYPE: PRT
<213> ORGANISM: artificial sequence
<220> FEATURE:
<223> OTHER INFORMATION: derivative from Exendin-4

<400> SEQUENCE: 7

His Gly Glu Gly Thr Phe Thr Ser Asp Leu Ser Lys Gln Met Glu Glu
                    1               5                  10                  15

Glu Ala Val Arg Leu Phe Ile Glu Trp Leu Lys Asn Gly Gly Pro Ser
                                        20                  25                  30

Ser Gly Ala Pro Pro Pro Cys Tyr
                                35                  40

<210> SEQ ID NO 8
<211> LENGTH: 39
<212> TYPE: PRT
<213> ORGANISM: artificial sequence
<220> FEATURE:
<223> OTHER INFORMATION: derivative from Exendin-4

<400> SEQUENCE: 8

His Ala Glu Gly Thr Phe Thr Ser Asp Leu Ser Lys Gln Met Glu Glu
                    1               5                  10                  15

Glu Ala Val Arg Leu Phe Ile Glu Trp Leu Lys Asn Gly Gly Pro Ser
                                        20                  25                  30

Ser Gly Ala Pro Pro Pro Cys
                                35
```